US011712483B2

(12) United States Patent
Page et al.

(10) Patent No.: US 11,712,483 B2
(45) Date of Patent: *Aug. 1, 2023

(54) ACTIVATABLE MEMBRANE-INTERACTING PEPTIDES AND METHODS OF USE

(71) Applicant: THE REGENTS OF THE UNIVERSITY OF CALIFORNIA, Oakland, CA (US)

(72) Inventors: Michael Page, Oakland, CA (US); Charles S. Craik, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 100 days.

This patent is subject to a terminal disclaimer.

(21) Appl. No.: 16/838,348

(22) Filed: Apr. 2, 2020

(65) Prior Publication Data

US 2020/0289677 A1   Sep. 17, 2020

Related U.S. Application Data

(63) Continuation of application No. 15/700,880, filed on Sep. 11, 2017, now Pat. No. 10,646,593, which is a
(Continued)

(51) Int. Cl.
*A61K 49/00* (2006.01)
*C08L 89/00* (2006.01)
(Continued)

(52) U.S. Cl.
CPC .......... *A61K 49/0056* (2013.01); *A61K 47/64* (2017.08); *A61K 47/65* (2017.08);
(Continued)

(58) Field of Classification Search
CPC .... A61K 47/60; A61K 47/65; A61K 47/6889; A61K 51/0497; A61K 38/00;
(Continued)

(56) References Cited

U.S. PATENT DOCUMENTS 4,296,105 A   10/1981   Baurain et al.
5,739,273 A   4/1998   Engelman et al.
(Continued)

FOREIGN PATENT DOCUMENTS

| GR | 20100100658 | * | 5/2012 | ............... C07K 7/08 |
| WO | WO2010118435 A2 | * | 10/2010 | ............. A61K 38/16 |
| WO | WO2013109927 A2 | * | 7/2013 | ........... C07D 501/28 |

OTHER PUBLICATIONS

Brendan F. Proteases as Selective Activators of Triggered Drug Release: A Potential Answer to the Problem of Biomaterial-Associated Infections? Glimore J Biotechnol Biomater 2012; 2(5): e111. (Year: 2012).*

(Continued)

*Primary Examiner* — Aradhana Sasan
*Assistant Examiner* — Jia-Hai Lee
(74) *Attorney, Agent, or Firm* — Brian E. Davy; Bozicevic, Field & Francis LLP

(57) ABSTRACT

The present disclosure provides activatable and detectable membrane-interacting peptides that, following activation, can interact with phospholipid bilayers, such as cell membranes. The present disclosure also provides methods of use of such compounds. The compounds of the present disclosure are of the general structure $X^{1a}$-A-$X^2$—Z—$X^{1b}$, where A is a membrane-interacting peptide region having a plurality of nonpolar hydrophobic amino acid residues that, following separation from portions Z, is capable of interaction with a phospholipid bilayer; Z is an inhibitory peptide region that can inhibit the activity of portion A; $X^2$ is a cleavable linker that can be cleaved to release cleavage products from the compound; and $X^{1a}$ and $X^{1b}$ are optionally-present chemical handles that facilitate conjugation of various cargo moieties to the compound. Prior to cleavage of the composition at $X^2$, the composition acts as a promolecule that does not associate with cellular membranes to a (Continued)

significant or detectable level. Following cleavage at cleavable linker $X^2$, the cleavage product including portion A is free to interact with a phospholipid bilayer (e.g., a cell membrane), and thus accumulate at a site associated with a cleavage-promoting environment. Detection of the membrane-associated cleavage product can be accomplished by detection of a moiety attached through $X^{1a}$ and/or $X^{1b}$. Such compositions can be used in a variety of methods, including, for example, use in directly imaging active clotting within a subject.

30 Claims, 25 Drawing Sheets

Specification includes a Sequence Listing.

Related U.S. Application Data continuation of application No. 14/773,240, filed as application No. PCT/US2014/025683 on Mar. 13, 2014, now Pat. No. 9,789,209.

(60) Provisional application No. 61/785,450, filed on Mar. 14, 2013.

(51) Int. Cl.
  C07K 7/08 (2006.01)
  A61K 47/65 (2017.01)
  A61K 47/64 (2017.01)

(52) U.S. Cl.
  CPC ...... A61K 49/0032 (2013.01); A61K 49/0054 (2013.01); C07K 7/08 (2013.01); C08L 89/00 (2013.01); C07K 2319/00 (2013.01); C07K 2319/50 (2013.01); C12N 2501/385 (2013.01)

(58) Field of Classification Search
  CPC .. A61K 38/164; A61K 47/64; A61K 39/3955; A61K 39/39558; A61K 47/6855; A61K 47/6811; A61K 47/555; A61K 47/6425; A61K 51/088; A61K 2800/57; A61K 38/04; A61P 35/00; A61P 35/04; A61P 31/04; A61P 31/00; A61P 31/12; A61P 17/04; A61P 17/10; A61P 7/04; C07K 2319/50; C07K 16/2863; C07K 16/30; C07K 2317/77; C07K 16/40
  See application file for complete search history.

(56) References Cited

U.S. PATENT DOCUMENTS

| | | | |
|---|---|---|---|
| 5,777,078 A | 7/1998 | Bayley et al. | |
| 5,817,771 A | 10/1998 | Bayley et al. | |
| 5,824,776 A | 10/1998 | Bayley et al. | |
| 6,028,066 A | 2/2000 | Unger | |
| 6,083,486 A | 4/2000 | Weissleder et al. | |
| 6,197,541 B1 | 3/2001 | Coughlin | |
| 6,214,345 B1 | 4/2001 | Firestone et al. | |
| 6,258,360 B1 | 7/2001 | von Borstel et al. | |
| 6,310,176 B1 | 10/2001 | Barra et al. | |
| 6,545,131 B1 | 4/2003 | Isaacs et al. | |
| 6,592,847 B1 | 7/2003 | Weissleder et al. | |
| 6,615,063 B1 | 9/2003 | Ntziachristos et al. | |
| 7,053,042 B1 | 5/2006 | Denmeade et al. | |
| 7,214,663 B2 | 5/2007 | Bebbington et al. | |
| 7,282,476 B2 | 10/2007 | Denmeade et al. | |
| 7,383,076 B2 | 6/2008 | Ntziachristos et al. | |
| 7,402,556 B2 | 7/2008 | Trouet et al. | |
| 7,425,541 B2 | 9/2008 | Dubois et al. | |
| 7,431,915 B2 | 10/2008 | Jiang et al. | |
| 7,544,477 B2 | 7/2009 | Balint et al. | |
| 7,589,178 B2 | 9/2009 | Le Bonniec et al. | |
| 7,635,682 B2 | 12/2009 | Denmeade et al. | |
| 7,745,395 B2 | 6/2010 | Denmeade et al. | |
| 7,820,623 B2 | 10/2010 | Sullivan et al. | |
| 7,829,350 B2 | 11/2010 | Josephson et al. | |
| 7,833,967 B2 | 11/2010 | Hogenhaug | |
| 7,833,979 B2 | 11/2010 | Sullivan et al. | |
| 9,789,209 B2 * | 10/2017 | Page ................ | A61K 49/0032 |
| 10,646,593 B2 * | 5/2020 | Page ................ | A61K 47/65 |
| 2007/0041904 A1 | 2/2007 | Jiang et al. | |
| 2010/0316643 A1 | 12/2010 | Eckert et al. | |
| 2012/0251445 A1 | 10/2012 | Jiang et al. | |

OTHER PUBLICATIONS

Minn et al. Genes that mediate breast cancer metastasis to lung. Nature 2005; 436(7050): 518-524. (Year: 2005).*

Notni et al. TRAP, a Powerful and Versatile Framework for Gallium-68 Radiopharmaceuticals. Chem. Eur. J. 2011, 17, 14718-14722. (Year: 2001).*

STN. CAS Registrysm: Exact and pattern searching of protein sequences. 2008. (Year: 2008).*

Amara et al. (2008) "Interaction between the coagulation and complement system" Adv Exp Med Biol. 632:71-79.

Ansell (2007) "Factor Xa or thrombin: is factor Xa a better target?" J Thromb Haemost. 5 Suppl 1:60-64.

Antalis et al. (2010) "The cutting edge: .membrane-anchored serine protease activities in the pericellular microenvironment" Biochem J. 428(3):325-346.

Antonini et al. (1983) "Interaction between serine (pro)enzymes and Kazal and Kunitz inhibitors" J Mol Biol. 165(3):543-558.

Bah et al. (2006) "Rapid kinetics of Na+ binding to thrombin" J Biol Chem. 281(52):40049-40056.

Belokoneva et al. (2003) "The hemolytic activity of six arachnid cationic peptides is affected by the phosphatidylcholine-to-sphingomyelin ratio in lipid bilayers." Biochim Biophys Acta., 1617(1-2):22-30.

Berger et al. (2001) "Filter extrusion of liposomes using different devices: comparison of liposome size encapsulation efficiency and process characteristics" Int J Pharm. 223(1-2):55-68.

Bernard et al. (2001) "Efficacy and safety of recombinant human activated protein C for severe sepsis" N Engl J Med. 344(10):699-709.

Blatt et al. (1985) "Depth-dependent fluorescent quenching in micelles and membranes" Biochim Biophys Acta. 822(1):43-62.

Blatt et al. (1986) "The association of acrylamide with proteins. The interpretation of fluorescence quenching experiments" Biochim Biophys Acta. 871(1):6-13.

Bock et al. (2007) "Exosites in the substrate specificity of blood coagulation reactions" J Thromb Haemost. 5 Suppl 1:81-94.

Boskovic et al. (2000) "Exosite binding tethers the macromolecular substrate to the prothrombinase complex and directs cleavage at two spatially distinct sites" J Biol Chem. 275(49):38561-38570.

Brandstetter et al. (1995) "X-ray structure of clotting factor IXa: active site and module structure related to Xase activity and hemophilia B" Proc Natl Acad Sci U S A. 92(21):9796-9800.

Butenas et al. (2000) "Models of blood coagulation" Blood Coagul Fibrinolysis. 11 Suppl 1: S9-13.

Claeson et al. (1981) "Small synthetic peptides with affinity for proteases in coagulation and fibrinolysis: an overview" Ann N Y Acad Sci. 370:798-811.

Coughlin (2000) "Thrombin signalling and protease-activated receptors" Nature. 407(6801):258-264.

D'Abramo et al. (2006) "Conformational behavior of temporin A and temporin L in aqueous solution: a computational/experimental study" Biopolymers. 81(3):215-224.

Dahlback et al. (2005) "The anticoagulant protein C pathway" FEBS Lett. 579(15):3310-3316.

Dang et al. (1995) "An allosteric switch controls the procoagulant and anticoagulant activities of thrombin" Proc Natl Acad Sci U S A. 92(13):5977-5981.

Davidson et al. (2003) "Molecular evolution of the vertebrate blood coagulation network" Thromb Haemost. 89(3):420-428.

(56) References Cited

OTHER PUBLICATIONS

Davie et al. (2006) "An overview of the structure and function of thrombin" Semin Thromb Hemost. 32 Suppl 1:3-15.
Di Cera (2008) "Thrombin" Mol Aspects Med. 29(4):203-254.
Eisenmesser et al. (2005) "Intrinsic dynamics of an enzyme underlies catalysis" Nature. 438(7064):117-121.
Epand et al. (1999) "Diversity of antimicrobiol peptides and their mechanisms of action" Biochim Biophys Acta. 1462(1-2):11-28.
Esmon (2003) "Inflammation and thrombosis" J Thromb Haemost. 1(7):1343-1348.
Fadeel et al. (2009) "The ins and outs of phospholipid asymmetry in the plasma membrane: roles in health and disease" Critical Reviews in Biochemistry and Molecular Biology, 44(5):264-277.
Furie et al. (2008) "Mechanisms of thrombus formation" N Engl J Med. 359(9):938-949.
Gandhi et al. (2008) "Structural identification of the pathway of long-range communication in an allosteric enzyme" Proc Natl Acad Sci U S A. 105(6):1832-1837.
Ganz (2003) "Defensins: antimicrobial peptides of innate immunity" Nat Rev Immunol. 3(9):710-720.
GenBank AAB47871.1 proteinase-activated receptor-2 [*Homo sapiens*]. Feb. 21, 1997 [Retrieved from the Internet Aug. 13, 2014: <http://www.ncbi.nlm.nih.gov/protein/1041729?report=genbank&log$=protalign&last_rank=3&RID=YPK05C2S01R>];amino acids 41-50.
Giannt et al. (2007) "Mechanism of Na(+) binding to thrombin resolved by ultra-rapid kinetics" Biophys Chem. 131(1-3):111-114.
Goodey et al. (2008) "Allosteric regulation and catalysis emerge via a common route" Nat Chem Biol. 4(8):474-482.
Hancock et al. (1998) "Cationic peptides: a new source of antibiotics" Trends Biotechnol. 16(2):82-88.
Hansen et al. (2008) "Predicting cell-penetrating peptides.", Advanced drug delivery reviews, 60(4-5):572-579.
Hedstrom (1996) "Trypsin: a case study in the structural determinants of enzyme specificity" Biol Chem. 377(7-8):465-470.
Hedstrom (2002) "Serine protease mechanism and specificity" Chem Rev. 102(12):4501-4524.
Hedstrom et al. (1992) "Converting trypsin to chymotrypsin: the role of surface loops" Science. 255(5049):1249-1253.
Hedstrom et al. (1994) "Converting trypsin to chymotrypsin: ground-state binding does not determine substrate specificity" Biochemistry. 33(29):8764-8769.
Hedstrom et al. (1994) "Converting trypsin to chymotrypsin: residue 172 is a substrate specificity determinant" Biochemistry. 33(29):8757-8763.
Hopfner et al. (1998) "New enzyme lineages by subdomain shuffling" Proc Natl Acad Sci U S A. 95(17):9813-9818.
Huntington and Li (2009) "Structural insights into the multiple functions of protein C inhibitor" Cell Mol Life Sci. 66:113-121.
Jabaiah et al. (2012) "Identification of protease exosite-interacting peptides that enhance substrate cleavage kinetics" Biol Chem. 393(9):933-941.
Jackel et al. (2008) "Protein design by directed evolution" Annu Rev Biophys. 37:153-173.
Jesty et al. (2005) "Positive feedbacks of coagulation: their role in threshold regulation" Arterioscler Thromb Vasc Biol. 25(12):2463-2469.
Kane et al. (1988) "Blood coagulation factors V and VIII: structural and functional similarities and their relationship to hemorrhagic and thrombotic disorders" Blood. 71(3):539-555.
Katzen et al. (2005) "The past present and future of cell-free protein synthesis" Trends Biotechnol. 23(3):150-156.
Khanin et al. (1989) "A mathematical model of the kinetics of blood coagulation" J Theor Biol. 136(2):127-134.
Kraut et al. (2003) "Challenges in enzyme mechanism and energetics" Annu Rev Biochem. 72:517-571.
Krem et al. (2001) "Molecular markers of serine protease evolution" Embo J. 20(12):3036-3045.

Lebel et al. (2008) "Novel solubility-switchable MRI agent allows the noninvasive detection of matrix metalloproteinase-2 activity in vivo in a mouse model" Magnetic Resonance Med. 60(5):1056-1065.
Lopez-Otin et al. (2002) "Protease degradomics: a new challenge for proteomics" Nat Rev Mol Cell Biol. 3(7):509-519.
Lottenberg et al. (1981) "Assay of coagulation proteases using peptide chromogenic and fluorogenic substrates" Methods Enzymol. 80 Pt C:341-361.
Lusher et al. (1993) "Recombinant factor VIII for the treatment of previously untreated patients with hemophilia A. Safety efficacy and development of inhibitors. Kogenate Previously Untreated Patient Study Group" N Engl J Med.
Mangoni (2006) "Temporins anti-infective peptides with expanding properties" Cell Mol Life Sci. 63(9):1060-1069.
Mangoni et al. (2004) "Effects of the antimicrobial peptide temporin L on cell morphology, membrane permeability and viability of *Escherichia coli*" Biochem J. 380(3):859-865.
Martinowitz et al. (2001) "Recombinant activated factor VII for adjunctive hemorrhage control in trauma" J Trauma. 51(3):431-438; discussion 438-439.
Mendes et al. (2004) "Structural and biological characterization of two novel peptides from the venom of the neotropical social wasp *Agelaia pallipes pallipes*" Toxicon. 44(1):67-74.
Mizukami et al. (2010) "Photocontrolled compound release system using caged antimicrobial peptide" J Am Chem Soc. 132(28):9524-9525.
Neiman et al. (2007) "Interaction of thrombin with PAR 1 and PAR4 at the thrombin cleavage site.", Biochemistry, 46(29): 8603-8610.
Olson et al. (1993) "Kinetic characterization of heparin-catalyzed and uncatalyzed inhibition of blood coagulation proteinases by antithrombin" Methods Enzymol. 222:525-559.
Page and Di Cera (2008) "Evolution of peptidase diversity" J Biol Chem. 283:30010-30014.
Page et al. (2003) "Engineering the primary substrate specificity of Streptomyces griseus trypsin" Biochemistry. 42(30):9060-9066.
Page et al. (2005) "Determinants of specificity in coagulation proteases" J Thromb Haemost. 3(11):2401-2408.
Page et al. (2006) "Conversion of trypsin into a Na(+)-activated enzyme" Biochemistry. 45(9):2987-2993.
Page et al. (2006) "Role of Na+ and K+ in enzyme function" Physiol Rev. 86(4):1049-1092.
Page et al. (2008) "Engineering protein allostery: 1.05 A resolution structure and enzymatic properties of a Na+-activated trypsin" J Mol Biol. 378(3):666-672.
Perona et al. (1995) "Structural basis of substrate specificity in the serine proteases" Protein Sci. 4(3):337-360.
Perona et al. (1995) "Structural origins of substrate discrimination in trypsin and chymotrypsin" Biochemistry. 34(5):1489-1499.
Perona et al. (1997) "Evolutionary divergence of substrate specificity within the chymotrypsin-like serine protease fold" J Biol Chem. 272(48):29987-29990.
Rauh et al. (2002) "Trypsin mutants for structure-based drug design: expression refolding and crystallization" Biol Chem. 383(7-8):1309-1314.
Rauh et al. (2003) "ZZ made EZ: influence of inhibitor configuration on enzyme selectivity" J Mol Biol. 330(4):761-770.
Rauh et al. (2004) "Understanding protein-ligand interactions: the price of protein flexibility" J Mol Biol. 335(5):1325-1341.
Reyda et al. (2003) "Reconstructing the binding site of factor Xa in trypsin reveals ligand-induced structural plasticity" J Mol Biol. 325(5):963-977.
Rezaie (2003) "Exosite-dependent regulation of the protein C anticoagulant pathway" Trends Cardiovasc Med. 13(1):8-15.
Riewald et al. (2002) "Orchestration of coagulation protease signaling by tissue factor" Trends Cardiovasc Med. 12(4):149-154.
Rinaldi et al. (2002) "Temporin L: antimicrobial haemolytic and cytotoxic activities and effects on membrane permeabilization in lipid vesicles" Biochem J. 368(Pt 1):91-100.
Sadler et al. (2000) "Impact diagnosis and treatment of von Willebrand disease" Thromb Haemost. 84(2):160-174.
Schmidt (2004) "Recombinant expression systems in the pharmaceutical industry" Appl Microbiol Biotechnol. 65(4):363-372.

(56) References Cited

OTHER PUBLICATIONS

Schmidt et al. (2002) Thermodynamic linkage between the S1 site the Na+ site and the Ca2+ site in the protease domain of human activated protein C (APC). J Biol CHem.277(32): 28987-28995.
Schmidt et al. (2005) "Na+ site in blood coagulation factor IXa: effect on catalysis and factor VIIIa binding" J Mol Biol. 350(1):78-91.
Schumann (2007) "Production of recombinant proteins in Bacillus subtilis" Adv Appl Microbiol. 62:137-189.
Shai (1999) "Mechanism of the binding, insertion and destabilization of phospholipid bilayer membranes by α-helical antimicrobial and cell non-selective membrane-lytic peptides" Biochimica et Biophysica Acta. 1462:55-70.
Spizizen (1958) "Transformation of Biochemically Deficient Strains of Bacillus Subtilis by Deoxyribonucleate" Proc Natl Acad Sci U S A. 44(10):1072-1078.
Steiner et al. (1980) "Stimulation of the amidase and esterase activity of activated bovine plasma protein C by monovalent cations" Biochem Biophys Res Commun. 94(1):340-347.
Tijburg et al. (1991) "Formation of meizothrombin as intermediate in factor Xa catalyzed prothrombin activation on endothelial cells. The influence of thrombin on the reaction mechanism" J Biol Chem. 266(6):4017-4022.
Underwood et al. (2000) "Thermodynamic linkage between the S1 site the Na+ site and the Ca2+ site in the protease domain of human coagulation factor xa. Studies on catalytic efficiency and inhibitor binding" J Biol Chem.266(6):4017-4022.
Veiseh et al. (2007) "Tumor Paint: A Chlorotoxin:Cy5.5 Bioconjugate for Intraoperative Visualization of Cancer Foci" Cancer Res. 67(14):6882-6888.
Vindigni et al. (1996) "Release of fibrinopeptides by the slow and fast forms of thrombin" Biochemistry. 35(14):4417-4426.
Vindigni et al. (1997) "Site-specific dissection of substrate recognition by thrombin" Nat Biotechnol. 15(9):891-895.
Weinmann and Moretti (2000) "$^{99m}$Tc-Apcitide Scintigraphy and the Detection of Acute Deep Vein Thrombosis" J. of Nuclear Med. 41(10):1768-1769.
Weiss et al. (2002) "Protection against thrombosis in mice 15 lacking PAR3" Blood. 100(9):3240-3244.
Wells et al. (1988) "Subtilisin—an enzyme designed to be engineered" Trends Biochem Sci. 13(8):291-297.
Wu et al. (1999) "Development of improved pUB110-based vectors for expression and secretion studies in Bacillus subtilis" J Biotechnol. 72(1-2):185-195.
Yasuda et al. (1981) "A simple method to measure anti-glycolipid antibody by using complement-mediated immune lysis of fluorescent dye-trapped liposomes" J Immunol Methods. 44(2):153-158.
Zasloff et al. (2002) "Antimicrobial peptides of multicellular organisms" Nature. 415(6870):389-395.
Zhong et al. (2008) "Antitumor activity of a membrane lytic peptide cyclized with a linker sensitive to membrane type 1-matrix metalloproteinase.", Mol Cancer Ther., 7(9):2933-40.

\* cited by examiner

ACTIVATABLE MEMBRANE-INTERACTING PEPTIDES AND METHODS OF USE

CROSS REFERENCE TO RELATED APPLICATIONS

This application is a continuation of U.S. application Ser. No. 15/700,880, filed Sep. 11, 2017, now pending, which application is a continuation of U.S. application Ser. No. 14/773,240, filed Sep. 4, 2015, now issued as U.S. Pat. No. 9,789,209, on Oct. 17, 2017, which application claims priority benefit of the filing date of U.S. Provisional Patent Application Ser. No. 61/785,450, filed on Mar. 14, 2013, the disclosure of which application is herein incorporated by reference in its entirety.

INTRODUCTION

Detection and diagnosis of disease is generally an important first step in selection of an appropriate therapy. However, many diseases and conditions involve biological processes that are difficult to detect with sufficient sensitivity and specificity to enable a correct diagnosis. Proteolytic events are an example of such a biological process and are directly or indirectly associated with a wide variety of diseases and conditions.

For example, despite gains in prevention and therapy, coronary heart disease remains a leading cause of mortality. The event that causes death is most often a blood clot in the coronary artery initiated by rupture of an atherosclerotic plaque. Such clots can directly occlude this major vessel or break off and migrate to smaller arteries causing myocardial ischemia and cellular damage. Current diagnostic tools include assays that provide for indirect assessment of cardiac damage using protein biomarkers. Such indirect assessment methods often are time consuming, as they frequently require obtaining multiple samples from a patient to monitor a change in biomarker levels over a period of time. In addition, biomarker assays provide little or no information as to a location and/or size of an active blood clot. More direct procedures can be used to identify an area of and extent of cardiac damage, but such direct procedures tend to be invasive, and are often not appropriate for all patients. Conventional imaging approaches available to facilitate assessment of cardiac damage are generally not used as a first line screening at least in part due to their relatively high cost, low sensitivity, and toxicity associated with the amount of radiation or imaging agent required to facilitate visualization. Such limitations apply to the diagnosis of other thrombotic problems either directly (i.e. heart attack and stroke) or indirectly (i.e., cancer and diabetes).

There is a need for tools to facilitate diagnosis of conditions associated with proteolytic activity.

SUMMARY

The present disclosure generally provides activatable and detectable membrane-interacting peptides that, following activation, can interact with phospholipid bilayers, such as cell membranes. The present disclosure also provides methods of use of such compounds.

The compounds of the present disclosure are of the general structure $X^{1a}$-A-$X^2$—Z—$X^{1b}$, where A is a membrane-interacting peptide region having a plurality of non-polar hydrophobic amino acid residues that, following separation from portion Z, is capable of interacting with a phospholipid bilayer; Z is an inhibitory peptide region that can inhibit the activity of portion A; $X^2$ is a cleavable linker that can be cleaved to release cleavage products from the compound; and $X^{1a}$ and $X^{1b}$ are optionally-present chemical handles that facilitate conjugation of various moieties to the compound. Prior to cleavage of the composition at $X^2$, the composition acts as a promolecule that does not associate with phospholipid bilayers to a significant or detectable level. Following cleavage at cleavable linker $X^2$, the cleavage product including portion A is free to interact with a phospholipid bilayer (e.g., a cell membrane), and thus accumulate at a site associated with a cleavage-promoting environment. Detection of the membrane-associated cleavage product can be accomplished by detection of a moiety attached through $X^{1a}$ and/or $X^{1b}$. Such compositions can be used in a variety of methods, including, for example, use in directly imaging active clotting within a subject.

In some embodiments, the present disclosure provides molecules that include the structure, from N-terminal to C-terminal or C-terminal to N-terminal: $X^{1a}$-A-$X^2$—Z—$X^{1b}$. wherein $X^{1a}$ and/or $X^{1b}$ may be present or absent, and when present comprise a nucleophilic moiety; A is a membrane-interacting polypeptide portion that, when separated from portion Z, comprises an alpha-helical structure capable of inserting into a phospholipid bilayer; Z is a polypeptide that, when linked to portion A through portion $X^2$, is effective to inhibit interaction of portion A with a phospholipid bilayer; and $X^2$ is a cleavable linker, wherein $X^2$ joins portion A to portion Z, and wherein $X^2$ can be cleaved under physiological conditions. In some embodiments, portion A includes about 5 to about 30 amino acid residues. In some embodiments, portion A includes the amino acid sequence $X^a X^b X^c X^d X^e X^f Y^a X^g X^h Y^b Y^* X^i X^j$ where $X^a$, $X^b$, $X^c$, $X^d$, $X^e$, $X^f$, $X^g$, $X^h$, $X^i$, and $X^j$ are hydrophobic amino acid residues, $Y^a$ and $Y^b$ are hydrophilic amino acid residues, and $Y^*$ is a charged amino acid residue. In some embodiments, portion A includes the amino acid sequence FVQWFSKFL-GRIL (SEQ ID NO: 2), or a conservative amino acid substitution thereof. In some embodiments, portion A includes the amino acid sequence FVQWFSKFLGKLL (SEQ ID NO: 3), or a conservative amino acid substitution thereof. In some embodiments, portion A includes the amino acid sequence ILGTILGLLKGL (SEQ ID NO: 4). In some embodiments, portion A includes the amino acid sequence of Japonicin-1 (SEQ ID NO: 5). In some embodiments, portion A includes the amino acid sequence FFWLSKIF (SEQ ID NO: 11). In some embodiments, portion A includes fewer than 5 basic amino acid residues.

In some embodiments, portion Z includes a covalently linked water soluble polymer. In some embodiments, $X^2$ is enzymatically cleavable. In some embodiments, $X^2$ is cleavable by thrombin. In some embodiments, $X^2$ is an enzymatically cleavable linker and Z includes an exosite recognition sequence for an enzyme that is capable of cleaving $X^2$. In some embodiments, $X^2$ is cleavable by thrombin and the exosite recognition sequence is derived from the thrombin exosite recognition sequence of a protease-activated receptor-1 (PAR-1) (SEQ ID NO: 18). In some embodiments, $X^2$ is cleavable by TMPRSS2 and the exosite recognition sequence is derived from the TMPRSS2 exosite recognition sequence of a protease-activated receptor-2 (PAR-2) (SEQ ID NO: 20). In some embodiments, Z includes the amino acid sequence SFLL($X^a$)NPNDKYEPFW, wherein $X^a$ is R or Q (SEQ ID NO: 23). In some embodiments, Z includes the amino acid sequence KVDGTSHVTGDDD (SEQ ID NO: 20). In some embodiments, one or more of $X^{1a}$, $X^{1b}$, A, or Z includes a D-amino acid. In some embodiments, $X^{1a}$ is present and includes a nucleophilic moiety. In some embodiments, $X^{1b}$ is present and includes a nucleophilic moiety. In some embodiments, the nucleophilic moiety of $X^{1a}$ or $X^{1b}$ includes a thiol functional group. In some embodiments, $X^{1a}$ or $X^{1b}$ includes an amino acid residue that includes the nucleophilic moiety. In some embodiments, the amino acid residue is a cysteine residue. In some embodiments, the amino acid residue is a lysine residue.

In some embodiments, $X^{1a}$ or $X^{1b}$ includes a cargo moiety covalently attached to the nucleophilic moiety. In some embodiments, the cargo moiety is a detectable moiety. In some embodiments, the detectable moiety includes a fluorescent moiety. In some embodiments, the detectable moiety comprises a radioisotope. In some embodiments, the present disclosure provides nucleic acids encoding the molecule described above. In some embodiments, the present disclosure provides compositions that include the molecules described above and a pharmaceutically acceptable carrier.

In some embodiments, the present disclosure provides methods of detectably labeling a cell, the methods including contacting a cell with a molecule as described above, wherein when the contacting is under conditions suitable for cleavage of the cleavable linker, the molecule is cleaved to release the membrane interacting polypeptide portion for interaction with a phospholipid bilayer of the cell and detectably labels the cell. In some embodiments, the cell is in vivo. In some embodiments, the subject is a human.

In some embodiments, the present disclosure provides methods for detection of a blood clot in a subject, the methods including administering to the subject a molecule as described above, wherein $X^2$ is cleavable by thrombin, wherein in the presence of thrombin the molecule is cleaved to release a cleavage product comprising the detectable moiety and the membrane interacting polypeptide portion and wherein the cleavage product interacts with a phospholipid bilayer of a cell in an area of thrombin enzyme activity, and detecting the presence or absence of the detectable label of the cleavage product, wherein the presence of the detectable label indicates an area of thrombin enzyme activity associated with active clotting.

In some embodiments, Z comprises an amino acid sequence of an exosite recognition sequence for thrombin. In some embodiments, Z comprises an amino acid sequence of an exosite recognition sequence for TMPRSS2. In some embodiments, Z comprises the exosite recognition sequence of protease-activated receptor-1 (PAR-1) (SEQ ID NO: 18). In some embodiments, Z comprises the exosite recognition sequence of protease-activated receptor-2 (PAR-2) (SEQ ID NO: 20).

In some embodiments, the present disclosure provides methods of making a molecule useful in delivery of a cargo moiety to a phospholipid bilayer, the methods including synthesizing the molecule as described above, wherein $X^{1a}$ is present, and attaching a cargo moiety to the nucleophilic moiety of $X^{1a}$, wherein a molecule useful in delivery of a cargo moiety to a phospholipid bilayer is produced. In some embodiments, the synthesizing involves culturing a recombinant host cell comprising an expression construct encoding the molecule. In some embodiments, the synthesizing is by chemical synthesis.

μM in 100 μL volume for 2 hours, and were then assessed for trypan blue dye exclusion as a measurement of cell viability and membrane integrity. High concentrations of the membrane-interacting peptide-containing cleavage product led to cell death, while high concentrations of the promolecule did not. Co-incubation of the promolecule (50 μM) with the proteases thrombin (5 nM) or plasmin (200 nM) or coagulation factor Xa (200 nM) demonstrates that thrombin selectively activates the promolecule.

Figure 10:
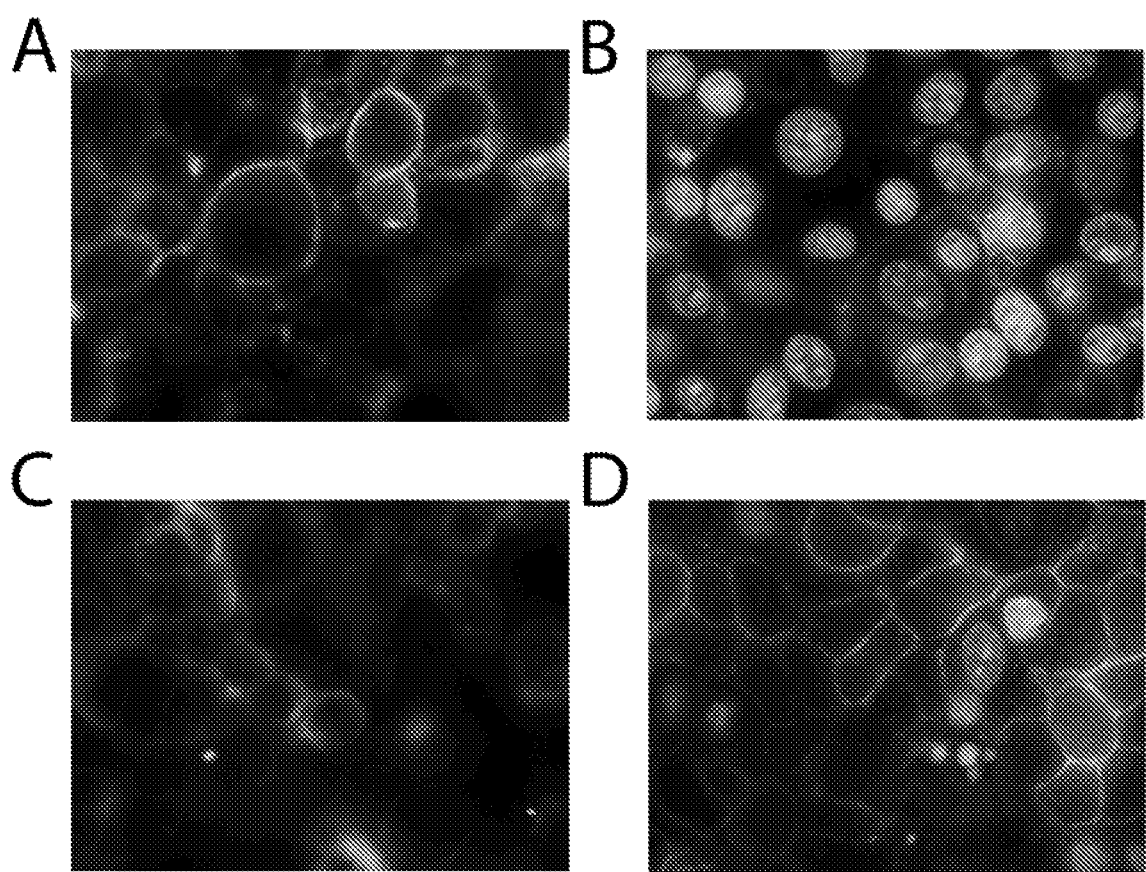

FIG. 10 shows exclusion of the fluorescent cell viability dye DRAQ7 by mouse pancreatic duct carcinoma cells under various conditions. DRAQ7 is more sensitive to membrane disruption than trypan blue dye and provides secondary validation. Images were obtained with an epifluorescent microscope. (Panel A) Cells were stained with wheat germ agglutinin conjugated to Oregon Green 488 to visualize their surfaces. (Panel B) Cells incubated with 100 μM of the membrane-interacting peptide-containing cleavage product were sufficiently permeabilized to enable uptake of DRAQ7, which becomes fluorescent upon interaction with deoxyribonucleic acid inside the cell. (Panel C) Cells were incubated with the promolecule for one hour. Without activation, the promolecule does not lead to significant uptake of DRAQ7 dye by cells. (Panel D) Cells were incubated with both a promolecule and thrombin for 30 minutes. Addition of thrombin (10 nM) with incubation for 30 minutes causes activation of the promolecule, resulting in permeabilization of the membrane and uptake of DRAQ7 dye by the cells.

Figure 11:
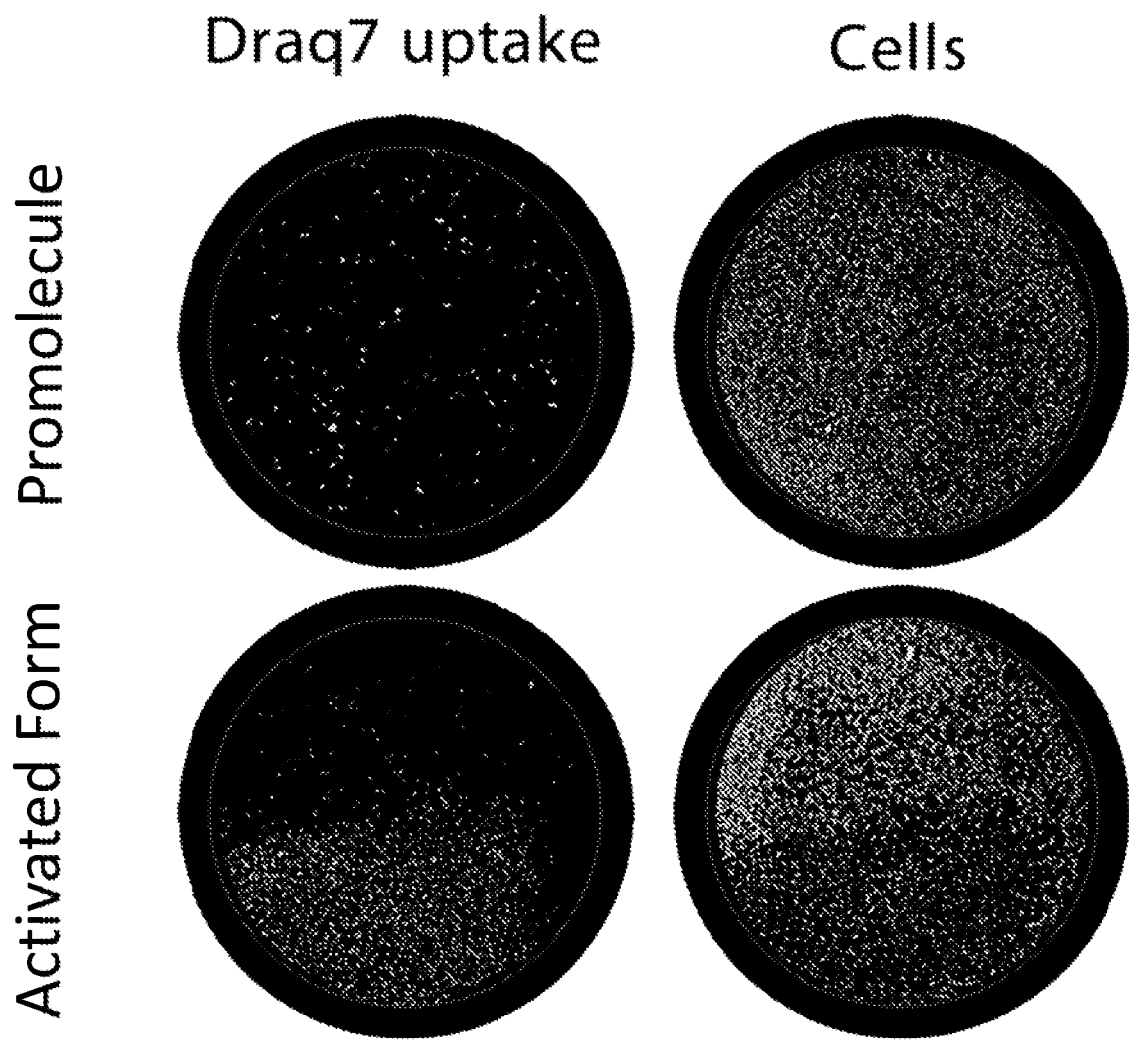

FIG. 11 shows exclusion of the fluorescent cell viability dye DRAQ7 by mouse X3 fibroblast cells under various conditions. Cells were incubated with a solution containing the promolecule (100 μM), or a solution containing the membrane-interacting peptide-containing cleavage product (100 μM). Incubation with the promolecule did not lead to extensive uptake of the DRAQ7 dye. Incubation with the membrane-interacting peptide-containing cleavage product resulted in permeabilization of the membrane and uptake of DRAQ7 dye, which becomes fluorescent upon the interaction with deoxyribonucleic acid inside the cell.

Figure 12:
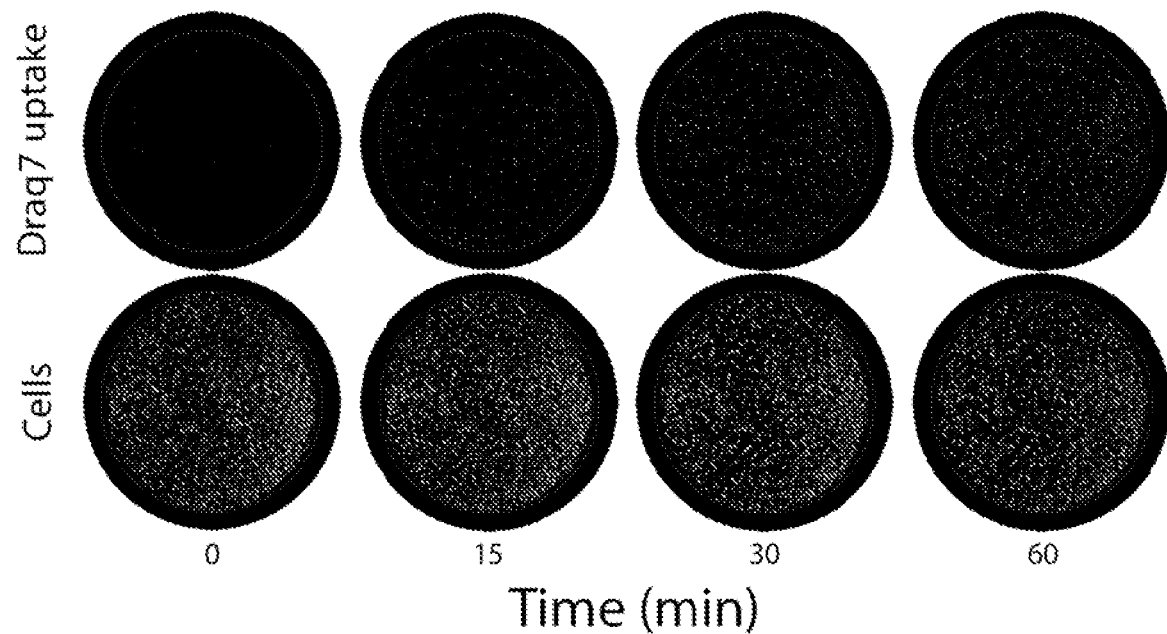

FIG. 12 shows exclusion of the fluorescent cell viability dye DRAQ7 by mouse X3 fibroblast cells under various conditions. The cell line was genetically altered to contain a variant of histone 2A conjugated to green fluorescent protein (GFP), which enabled cell counting. Addition of thrombin (5 nM) and the promolecule (100 μM) caused the number of permeabilized cells to increase as a function of time. In the absence of thrombin, permeabilization did not occur at a significant rate over the time frame of the experiment.

Figure 13:
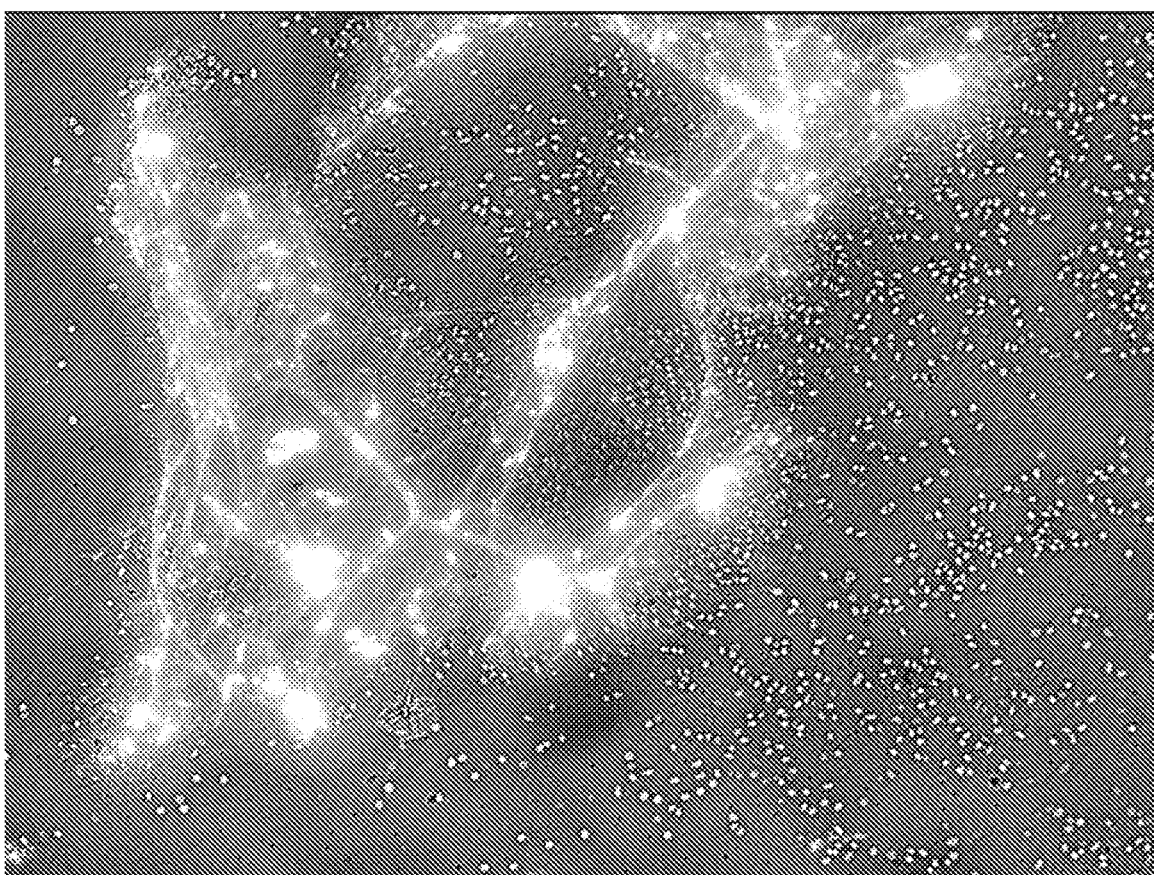

FIG. 13 shows localization of the membrane-interacting peptide-containing cleavage product to blood clots formed in vitro. Red blood cells appear as small, spherical cells and do not accumulate a fluorescent signal, as they are not sites of clot formation.

Figure 14:
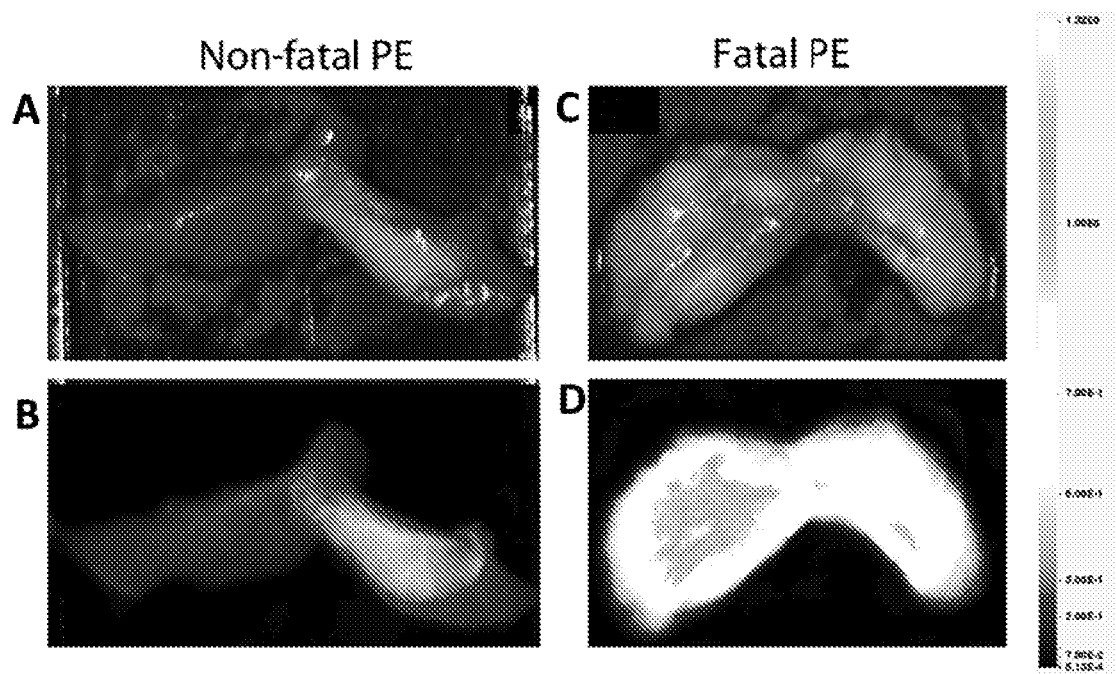

FIG. 14 shows images of the lungs of a mouse injected with various doses of thromboplastin to induce formation of emboli in the lungs. Panels A and B show lungs from a mouse receiving a non-lethal dose of thromboplastin. Panels C and D show lungs from a mouse receiving a fatal dose of thromboplastin. Panel A shows a visual light image of the lungs of a mouse receiving a non-fatal dose, with areas of emboli formation visible as white regions. Panel B shows a fluorescent microscope image of the same lungs, with regions of membrane-interacting peptide-containing cleavage product accumulation visible in areas of emboli formation. Panel C shows a visual light image of the lungs of a mouse receiving a fatal dose, with areas of emboli formation visible as white regions. Panel D shows a fluorescent microscope image of the same lungs, with regions of membrane-interacting peptide-containing cleavage product accumulation visible in areas of emboli formation.

Figure 15:

FIG. 15 shows an image obtained using a small animal fluorescence and near-infrared fluorescence imaging system. A puncture wound to the hind leg of an animal was visualized by detecting accumulation of the membrane-interacting peptide-containing cleavage product at the wound site.

Figure 16:
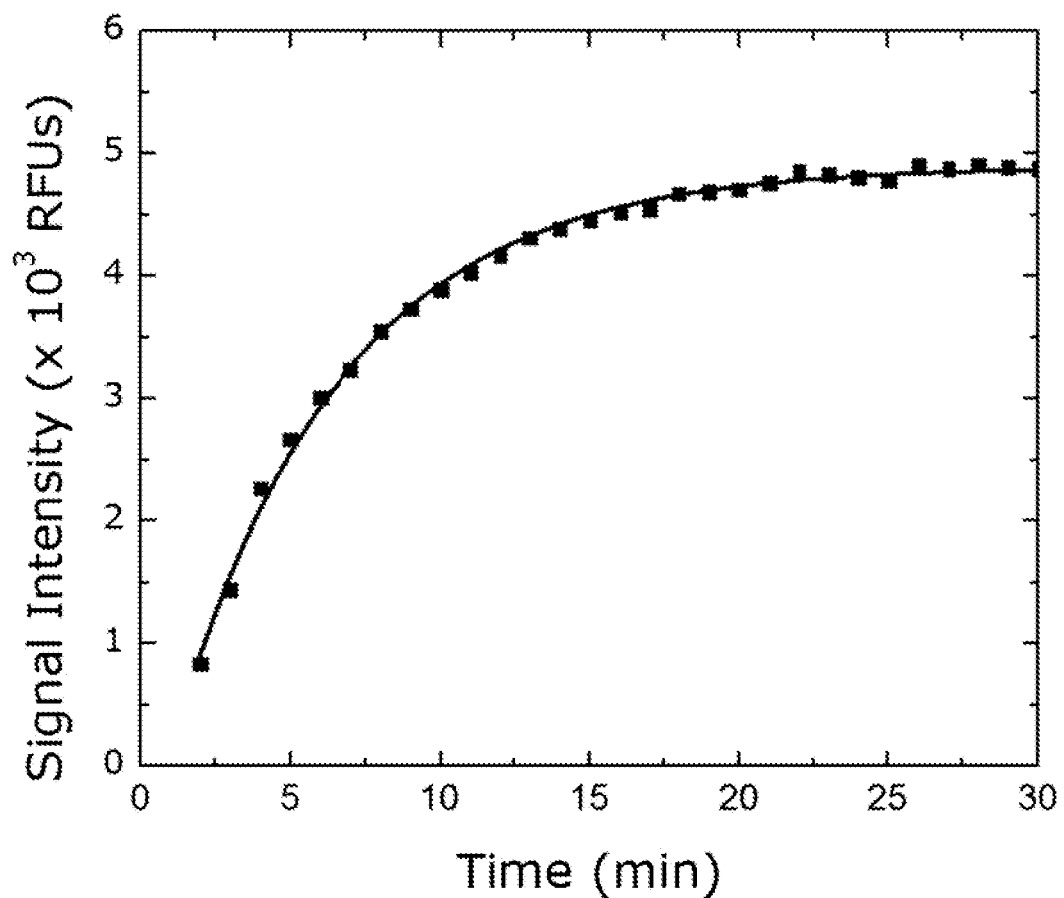

FIG. 16 is a graph showing the intensity of a fluorescent dye signal as a function of time. A puncture wound was inflicted to the hind leg of an animal, and a region of interest was drawn at the site of wounding. The intensity of the fluorescent signal coming from the region was plotted as a function of time. The resulting curve was used to quantify the rate of clot formation.

Figure 17:
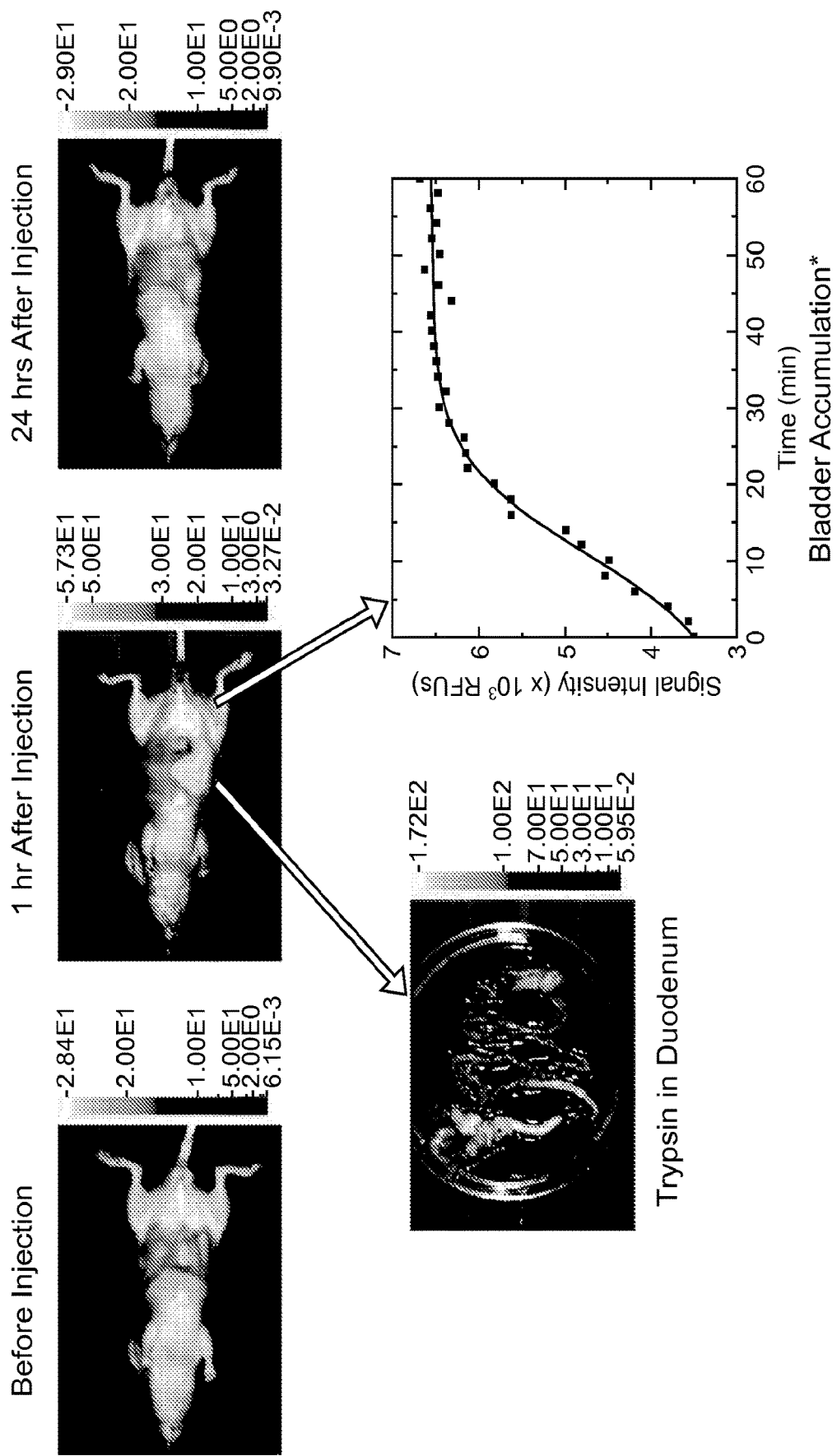

FIG. 17 shows images and data collected from an animal that was administered promolecules of the present disclosure. The upper left panel shows a fluorescent microscope image taken before administration of the promolecule. The upper middle panel shows a fluorescent microscope image taken one hour after administration of the promolecule. The upper right panel shows a fluorescent microscope image taken 24 hours after administration of the promolecule. The lower left panel shows a fluorescent microscope image of the duodenum of the animal. The lower right panel shows a graph of signal intensity of the fluorescent dye emanating from the bladder of the animal as a function of time.

Figure 18:
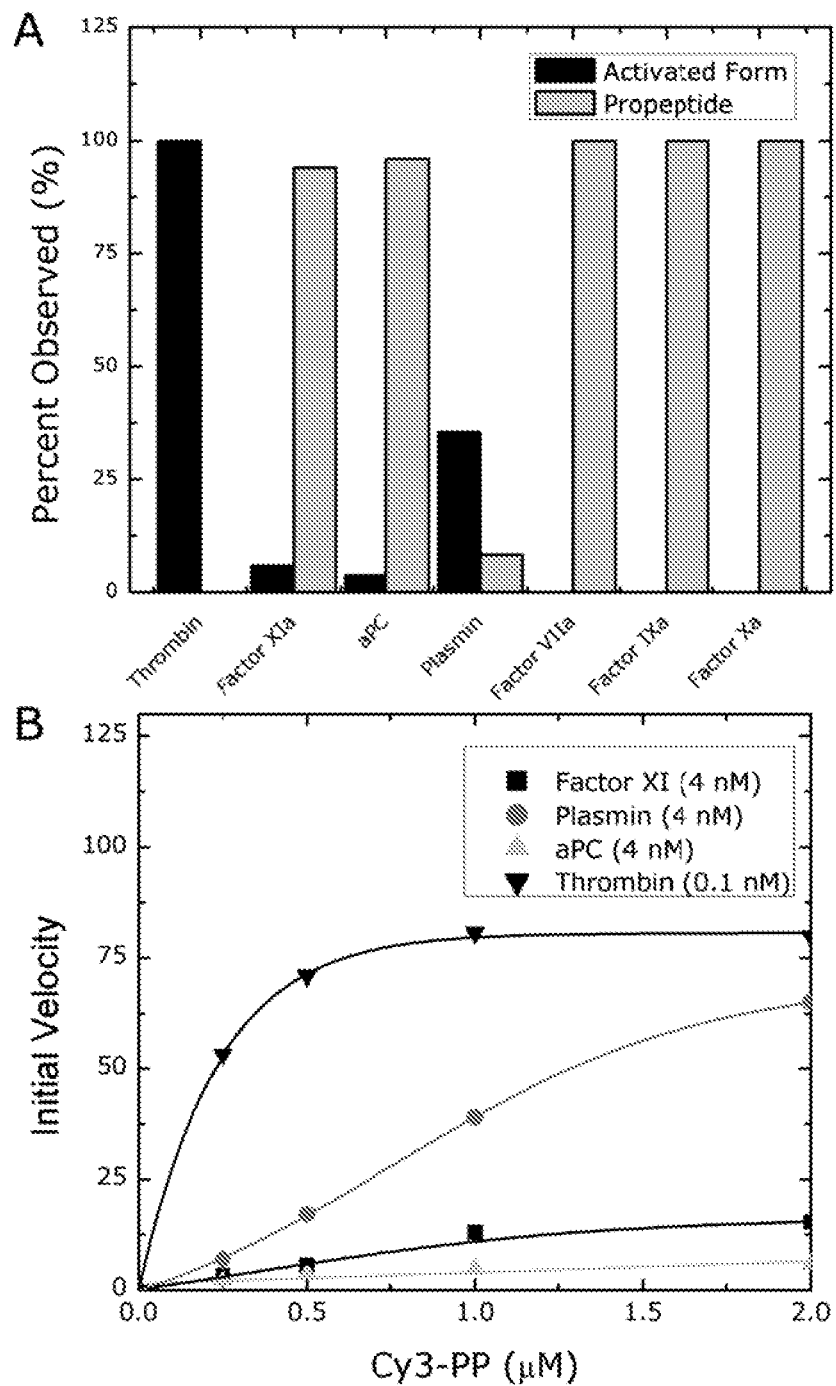

FIG. 18 shows data obtained by reverse phase high pressure liquid chromatography (HPLC). Panel A shows data obtained from solutions of the promolecule incubated with different proteases at the same concentration (2 nM) for 30 minutes at 37° C. Panel B shows a graph plotting the activation kinetics of the promolecule when incubated with various proteases.

Figure 19:
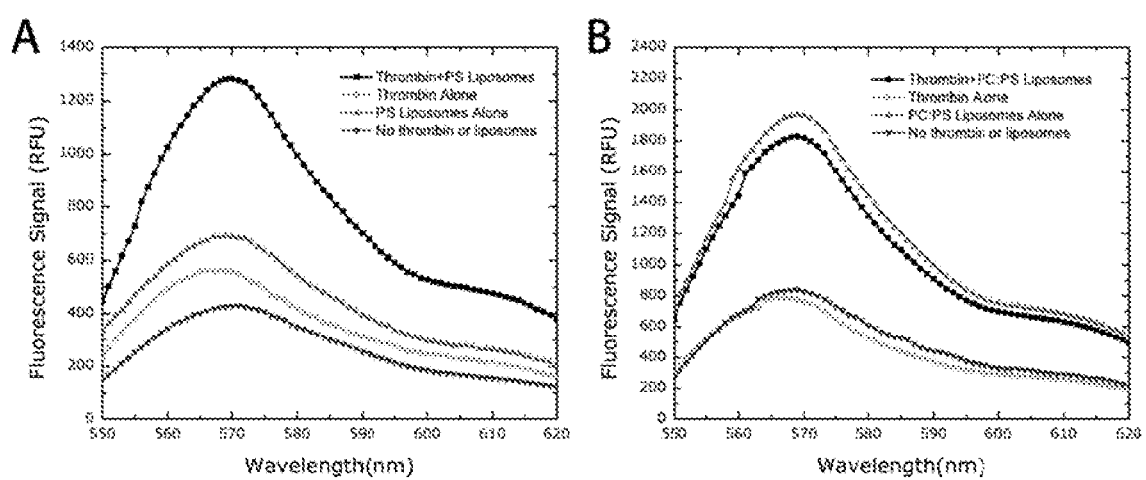

FIG. 19 shows data obtained using fluorescence resonance energy transfer (FRET). Promolecules and membrane-interacting peptide-containing cleavage products where incubated with liposomes having a 100 nm diameter and composed phosphatidylcholine and phosphatidylserine in a 3:1 molar ratio (PC:PS) or entirely of phosphatidylserine (PS) and 3,3'-dioctadecyloxacarbocyanine perchlorate (DiO). Panel A shows that prior to activation, the promolecules do not associate closely enough with the PS liposomes to enable FRET from the DiO. In contrast, the activated form exhibits a significant FRET signal indicating intimate association with DiO and phospholipid membranes containing PS. Panel B shows that if the liposomes are formulated to have less phosphatidylserine, the membrane-interacting peptide-containing cleavage product does not appear to interact with sufficient intimacy to enable FRET after activation by thrombin.

Figure 20:
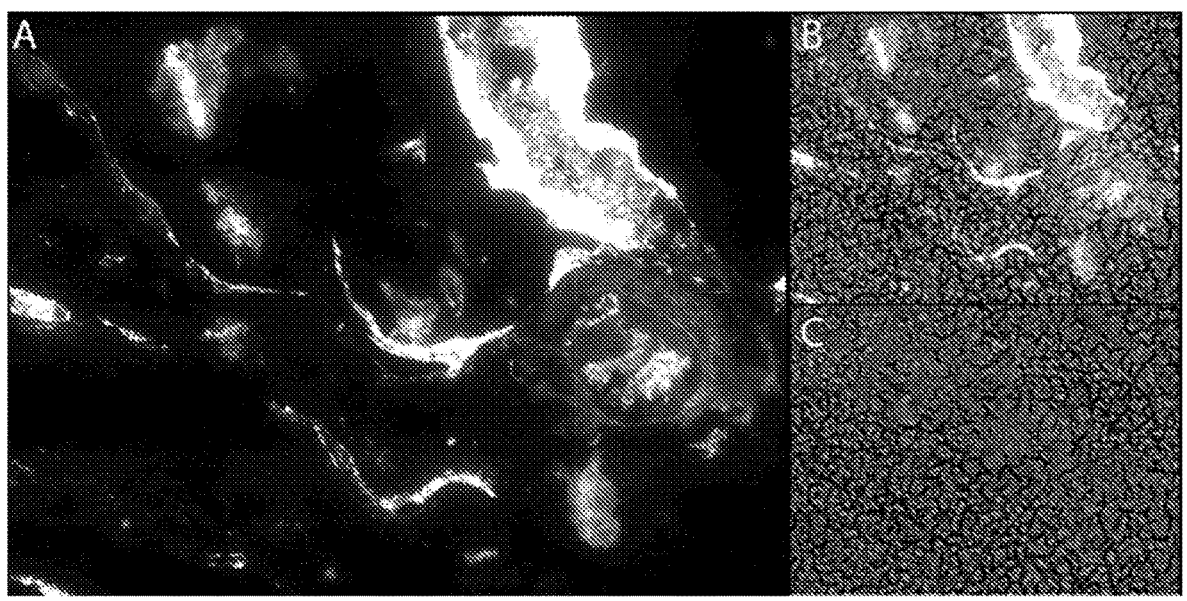

FIG. 20 shows the localization of membrane-interacting peptide-containing cleavage products in blood clots formed in vitro. Red blood cells appear as small, spherical cells on the periphery of the slide and do not accumulate a fluorescent signal, as they are not sites of clot formation. Panel A shows an image visualizing Cy3 fluorescent dye alone. Panel B shows a composite image of Cy3 fluorescent dye and brightfield signals. Panel C is an image showing brightfield signal alone.

Figure 21:
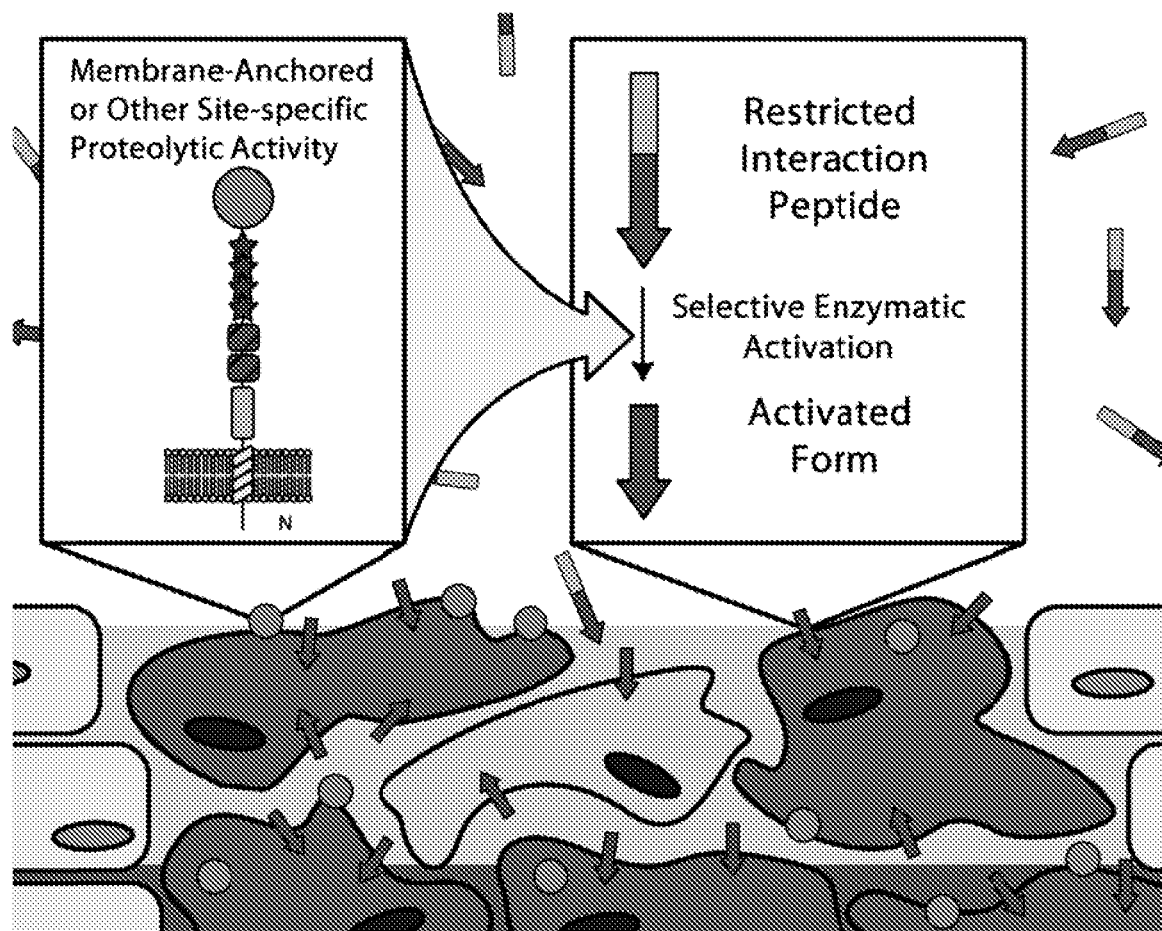

FIG. 21 shows a schematic representation of a promolecule of the present disclosure used for detection of proteolysis by a target enzyme. Upon activation by an enzyme, a promolecule is converted into a membrane-interacting form, and accumulates in the vicinity of a cleavage-promoting environment, enabling detection of a particular disease or condition.

Figure 22:
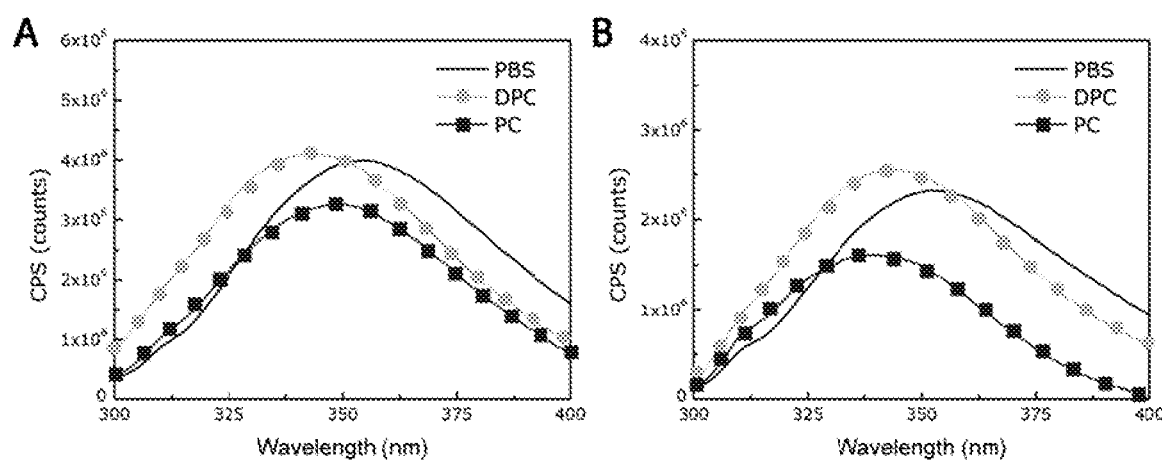

FIG. 22 shows data obtained from intrinsic fluorescence analysis. Panel A shows that, prior to activation, the spectral properties of the promolecule undergo a limited change in the presence of liposomes composed of phosphatidylcholine (PC) or phosphatidylserine (PS) compared to buffer alone (PBS). Panel B shows that the membrane-interacting peptide-containing cleavage product presents a marked blue shift in maximum wavelength, indicating that it inserts into membranes.

Figure 23:
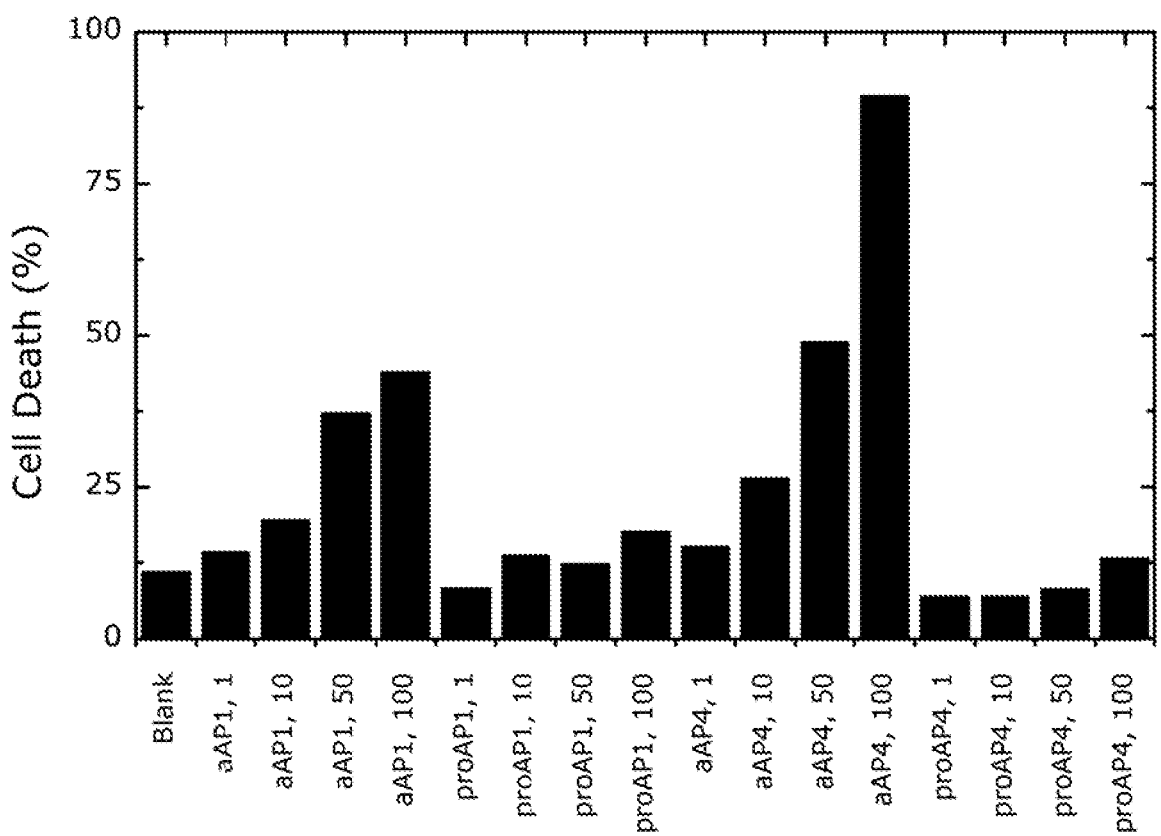

FIG. 23 is a graph showing the uptake of trypan blue dye by MDA-MB-231 cells under various conditions. High concentrations of the membrane-interacting peptide-containing cleavage product led to cell death, while high concentrations of the promolecule did not.

Figure 24:
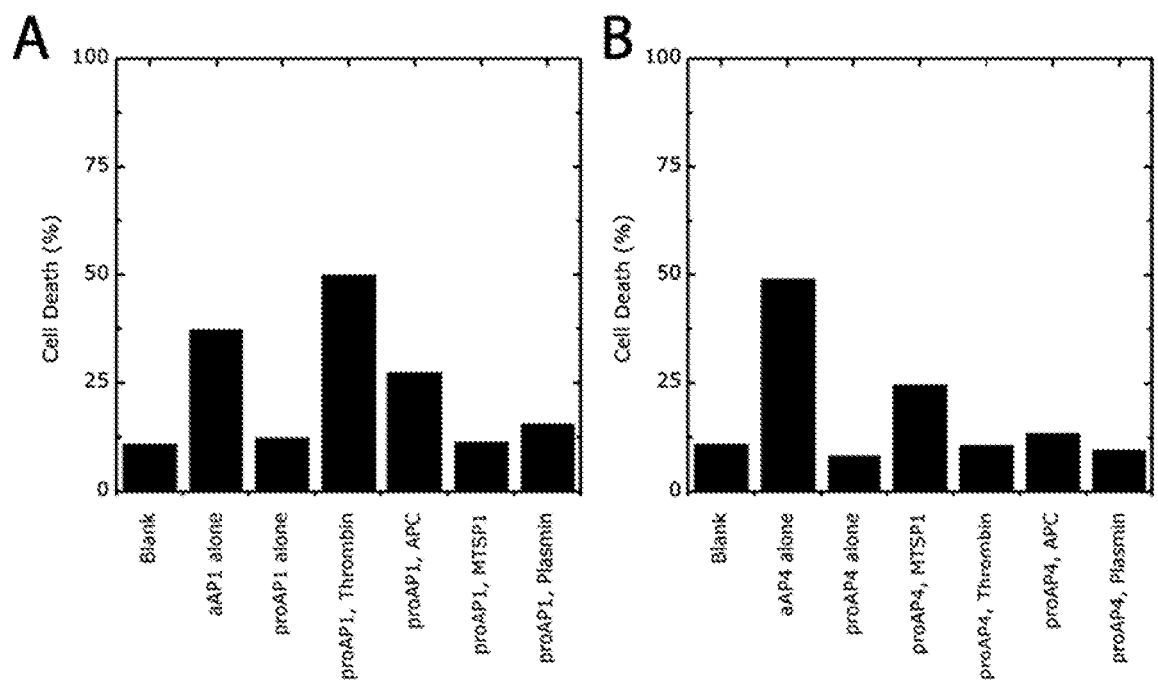

FIG. 24 is a graph showing the uptake of trypan blue dye by MDA-MB-231 cells under various conditions. Panel A shows that a promolecule cleaved by thrombin is selectively activated by thrombin. Panel B shows that a promolecule cleaved by matriptase is selectively activated by matriptase.

Figure 25:
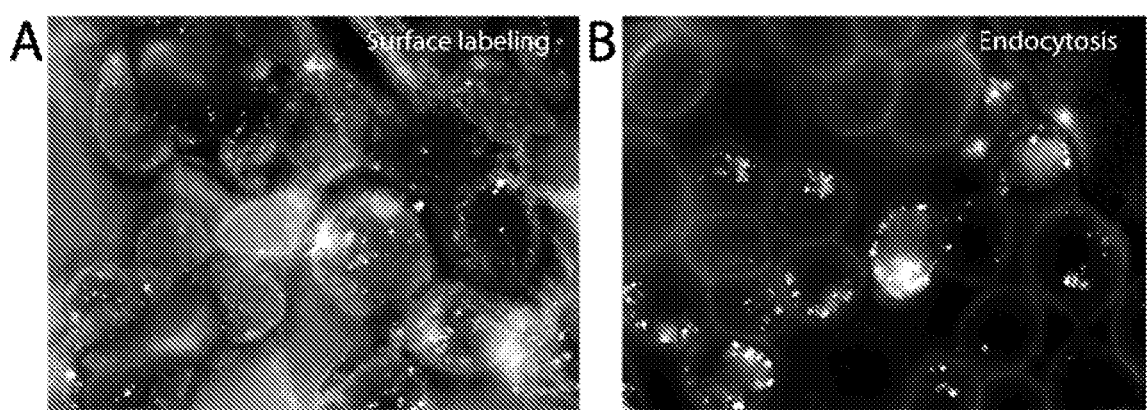

FIG. 25 shows microscopic images of HT29 cells incubated with promolecules of the present disclosure. The surfaces of HT29 cells were labeled with wheat germ agglutinin conjugated to Oregon Green 488. After co-incubation of a promolecule (10 nM) with HT29 cells for 20 minutes, a fluorescent signal from the promolecule was detectable on the surface of cells (Panel A). Subsequent washing and imaging 24 hours later revealed that the fluorescent signal from the promolecule was localized in punctate spheres inside the cells (Panel B).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "the molecule" includes reference to one or more proteins, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "polypeptide," "oligopeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusion proteins with heterologous and homologous leader sequences, with or without N-terminal methionine residues; immunologically tagged proteins; and the like.

The term "membrane-interacting peptide" refers to a peptide molecule having a plurality of nonpolar hydrophobic amino acid residues, and, when unconstrained by a portion Z as described herein, comprises an alpha-helical structure capable of interaction with phospholipid bilayers such as a cell membrane. Such secondary structure may appear before, during or after insertion of the membrane-interacting peptide into the phospholipid bilayer. The composition of membrane-interacting peptides as described herein is not strictly limited to nonpolar hydrophobic amino acid residues, as such peptides may include different types of amino acid residues, for example, polar uncharged, polar basic, or polar acidic amino acid residues as well.

The term "antimicrobial polypeptide" refers to a type of membrane-interacting peptide that is derived from a naturally-occurring peptide that exhibits antimicrobial activity in its natural form based on its ability to interact with cell membranes. It is understood that the term "antimicrobial polypeptide" as used herein does not require or imply that the polypeptides so described have antimicrobial activity. Any peptide shown to spontaneously interact with and potentially insert into phospholipid membranes are included in this category. For example, spontaneously inserting membrane interaction peptides from naturally occurring transmembrane proteins may be applied. Antimicrobial polypeptides are well known in the art, and include, for example, polypeptides in the temporin family of proteins.

The term "promolecule" as used herein refers to a molecule whose activity is restricted because the individual portions of the molecule are linked together, therefore limiting or restricting the activity that the individual portions may have when not linked to one another. The activity of the individual portions of a promolecule is unleashed upon cleavage or disruption of the bonds that hold the individual portions together.

The term "enzyme-activated" refers to a molecule whose behavior is modified by an enzyme. Many activating enzymes fall under the class of hydrolases EC 3.1 to EC 3.13 or peptidases EC 3.4 to 3.99 in the Nomenclature Committee of the International Union of Biochemistry and Molecular Biology (NC-IUBMB). Example enzyme activities include those that act upon bonds of the type ether, peptide, carbon-nitrogen, acid anhydrides, carbon-carbon, halide, phosphorus-nitrogen, sulfur-nitrogen, carbon-phosphorus, sulfur-sulfur, carbon-sulfur.

The term "non-standard amino acid" means any molecule other than a naturally-occurring amino acid molecule that can be incorporated into a peptide backbone of a polypeptide in lieu of a naturally-occurring amino acid residue in a polypeptide. Non-limiting examples of such non-standard amino acids include: hydroxylysine, desmosine, isodesmosine, or others.

The term "modified amino acid" means any naturally-occurring amino acid that has undergone a chemical or biochemical modification, such as a post-translational modification. Non-limiting examples of modified amino acids include: methylated amino acids, (e.g. methyl histidine, methylated lysine) acetylated amino acids, amidated amino acids, formylated amino acids, hydroxylated amino acids, phosphorylated amino acids, or others.

As used herein, "homologues" or "variants" refers to protein sequences that are similar based on their amino acid sequences. Homologues and variants include proteins that differ from naturally-occurring sequences by one or more conservative amino acid substitutions.

As used herein, the term "conservative amino acid substitution" means a substitution of an amino acid residue for another amino acid residue having similar chemical properties.

The term "treatment" as used herein means that at least an amelioration of the symptoms associated with a disease or condition afflicting the subject is achieved, where amelioration refers to at least a reduction in the magnitude of a parameter, e.g., a symptom, associated with the disease or condition being treated. As such, treatment includes situations where the condition, or at least symptoms associated therewith, are reduced or avoided.

It will be appreciated that throughout the present disclosure reference is made to amino acids according to the single letter or three letter codes. For the reader's convenience, the single and three letter amino acid codes are provided below. In addition, the amino acid residues provided below are divided into categories based on their chemical properties. The headings provided in the table below (Nonpolar, Hydrophobic; Polar, Uncharged; Polar, Acidic; and Polar, Basic) are used to refer generally to amino acid residues having the identified chemical properties.

| Nonpolar, Hydrophobic Residues | | |
|---|---|---|
| Alanine | Ala | A |
| Valine | Val | V |
| Leucine | Leu | L |
| Isoleucine | Ile | I |
| Phenylalanine | Phe | F |
| Tryptophan | Trp | W |
| Methionine | Met | M |
| Proline | Pro | P |
| Polar, Acidic | | |
| Aspartic Acid | Asp | D |
| Glutamic Acid | Glu | E |
| Polar, Uncharged Residues | | |
| Glycine | Gly | G |
| Serine | Ser | S |
| Threonine | Thr | T |
| Cysteine | Cys | C |
| Tyrosine | Tyr | Y |
| Asparagine | Asn | N |
| Glutamine | Gln | Q |
| Polar, Basic | | |
| Lysine | Lys | K |
| Arginine | Arg | R |
| Histidine | His | H |

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "heterologous" refers to two components that are defined by structures that can be derived from different sources. For example, where "heterologous" is used in the context of a polypeptide, the polypeptide includes operably linked amino acid sequences that can be derived from polypeptides having different amino acid sequences (e.g., a first amino acid sequence from a first polypeptide and a second amino acid sequence from a second polypeptide). Similarly, "heterologous" in the context of a polynucleotide encoding a chimeric polypeptide includes operably linked nucleic acid sequences that can be derived from different genes (e.g., a first component from a nucleic acid encoding a first portion of a peptide according to an embodiment disclosed herein and a second component from a nucleic acid encoding a second portion of a peptide disclosed herein).

"Derived from" in the context of an amino acid sequence or polynucleotide sequence (e.g., a polypeptide derived from an antimicrobial peptide) is meant to indicate that the polypeptide or nucleic acid has a sequence that is based on that of a reference polypeptide or nucleic acid, and is not meant to be limiting as to the source or method in which the protein or nucleic acid is made.

The term "operably linked" refers to functional linkage between molecules to provide a desired function. For example, "operably linked" in the context of a polypeptide refers to a functional linkage between amino acid sequences (e.g., of different domains) to provide for a described activity of the polypeptide. "Operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide.

As used herein in the context of the structure of a polypeptide, "N-terminus" and "C-terminus" refer to the extreme amino and carboxyl ends of the polypeptide, respectively, while "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Isolated" refers to a protein of interest (e.g., a membrane-interacting peptide) that, if naturally occurring, is in an environment different from that in which it may naturally occur. "Isolated" is meant to include proteins that are within samples that are substantially enriched for the protein of interest and/or in which the protein of interest is partially or substantially purified. Where the protein is not naturally occurring, "isolated" indicates the protein has been separated from an environment in which it was made by either synthetic or recombinant means.

"Enriched" means that a sample is non-naturally manipulated (e.g., by an experimentalist or a clinician) so that a protein of interest is present in a greater concentration than the concentration of the protein in the starting sample, such as a biological sample (e.g., a sample in which the protein naturally occurs or in which it is present after administration), or in which the protein was made (e.g., as in a bacterial protein and the like).

"Substantially pure" indicates that an entity makes up greater than about 50% of the total content of the composition (e.g., total protein of the composition), or greater than about 60% of the total protein content. For example, a "substantially pure" peptide refers to compositions in which at least 75%, at least 85%, at least 90% or more of the total composition is the entity of interest (e.g. 95%, 98%, 99%, greater than 99%), of the total protein. The protein can make up greater than about 90%, or greater than about 95% of the total protein in the composition.

The term "binding" refers to a direct association between two molecules, due to, for example, covalent, electrostatic, hydrophobic, and ionic and/or hydrogen-bond interactions, including interactions such as salt bridges and water bridges.

The term "nucleophilic moiety" as used herein refers to a functional group, which comprises a nucleophilic reactive group. A nucleophilic reactive group comprises at least one pair of free electrons that is able to react with an electrophile. Examples of nucleophilic moieties include sulfur nucleophiles, such as thiols, thiolate anions, anions of thiolcarboxylate, anions of dithiocarbonates, and anions of dithiocarbamates; oxygen nucleophiles, such as hydroxide anion, alcohols, alkoxide anions, and carboxylate anions; nitrogen nucleophiles, such as amines, azides, and nitrates; and carbon nucleophiles, such as alkyl metal halides and enols.

The terms "patient" or "subject" as used interchangeably herein can refer to a human or to a non-human animal, e.g. a mammal, including humans, primates, domestic and farm animals, and zoo, sport, laboratory, or pet animals, such as horses, cows, dogs, cats, rodents, and the like.

DETAILED DESCRIPTION

Overview

The present disclosure generally provides activatable and detectable membrane-interacting peptides that can be used to identify areas of a subject that are associated with a particular biological activity, e.g., proteolysis. Following activation, the promolecules of the present disclosure are capable of forming alpha-helical structures that interact with and insert into phospholipid bilayers, such as cell membranes. The present disclosure also provides methods of use of such compounds.

The compounds of the present disclosure find use in, for example, methods relating to the diagnosis of disease. For example, an activatable membrane-interacting peptide having a portion $X^2$ that is cleavable by the enzyme thrombin can be administered to a subject suspected of having a condition associated with thrombin activity, such as active blood clotting. In this example, exposure of the molecule to an area of thrombin activity in the subject results in cleavage at $X^2$ to generate a cleavage product containing portion A, which cleavage product is capable of inserting into cell membranes in the area of thrombin activity and thus in the area of active clotting. Detection of this cleavage product in cell membranes can be accomplished by imaging of the tissue(s) suspected of being associated with active clotting to image a detectable moiety attached to portion A through portion $X^{1a}$. The presence of thrombin activity in a subject can also be assessed by detection of the cleavage product containing portion Z, which may be facilitated by moieties attached as portion $X^{1b}$.

The compositions of the present disclosure can be used in a variety of methods, including, e.g., use in directly imaging active clotting, infection, or malignancy within a subject.

Activatable Membrane-Interacting Peptides

The promolecules of the present disclosure are of the general structure, from N-terminus to C-terminus or from C-terminus to N-terminus:

where

Figure 1:
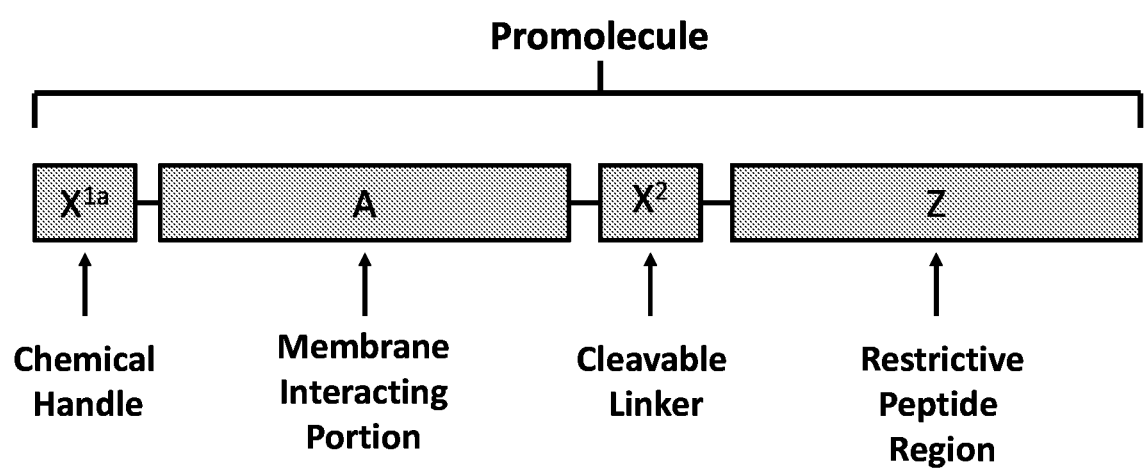
FIG. 1 shows a schematic diagram of an example of a promolecule of the present disclosure. The promolecule is of the general structure $X^{1a}$-A-$X^2$—Z. The membrane-interacting portion A can be conjugated to an imaging modality via portion $X^{1a}$. Region A is linked to a cleavable linker $X^2$, which is linked to a membrane-interacting inhibiting portion Z. After cleavage of $X^2$ by, e.g., an enzyme, portion A is separated from portion Z.
Figure 1:

A is a membrane-interacting peptide region having a plurality of nonpolar hydrophobic amino acid residues that, following cleavage from the composition, comprises an alpha-helical structure capable of interacting with a phospholipid bilayer (FIG. 1);

Z is an inhibitory peptide region that can inhibit the activity of portion A and, in some embodiments, can facilitate targeted interaction of a promolecule with a specific enzyme; and $X^2$ is a cleavable linker that can be cleaved to release cleavage products from the compound.

Figure 2:
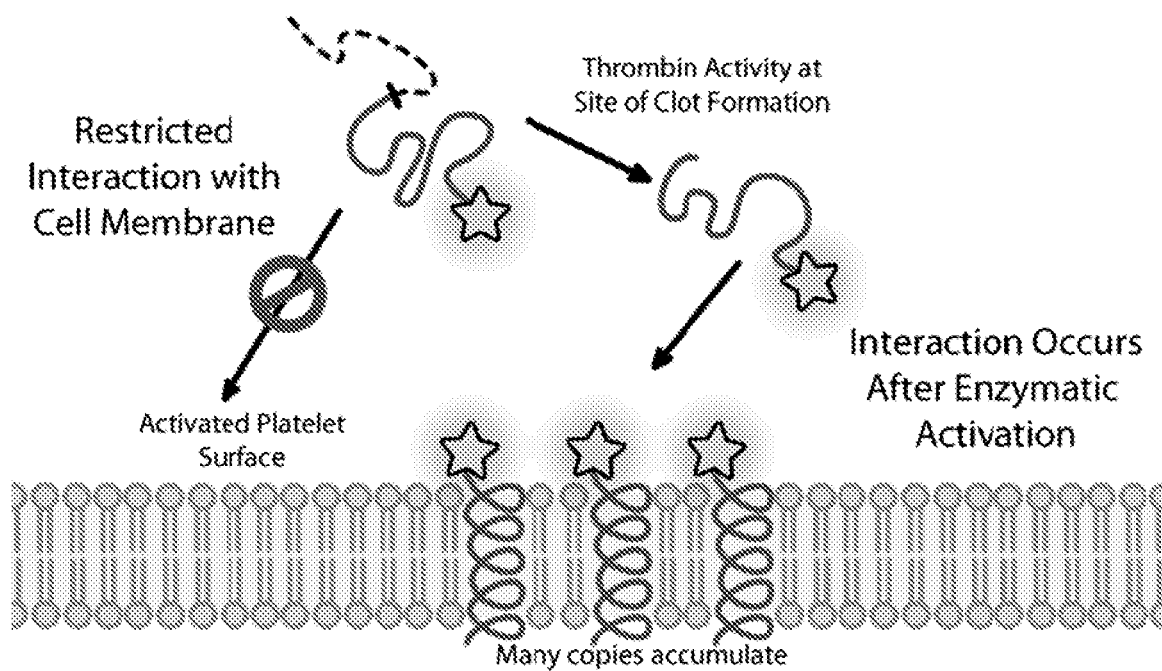
FIG. 2 is a schematic diagram that shows promolecules of the present disclosure undergoing a conformational change and inserting into cell membranes. The schematic diagram shows that the process is dependent upon separation of portion Z from portion A following cleavage at $X^2$ by, e.g., a protease.
Figure 3:
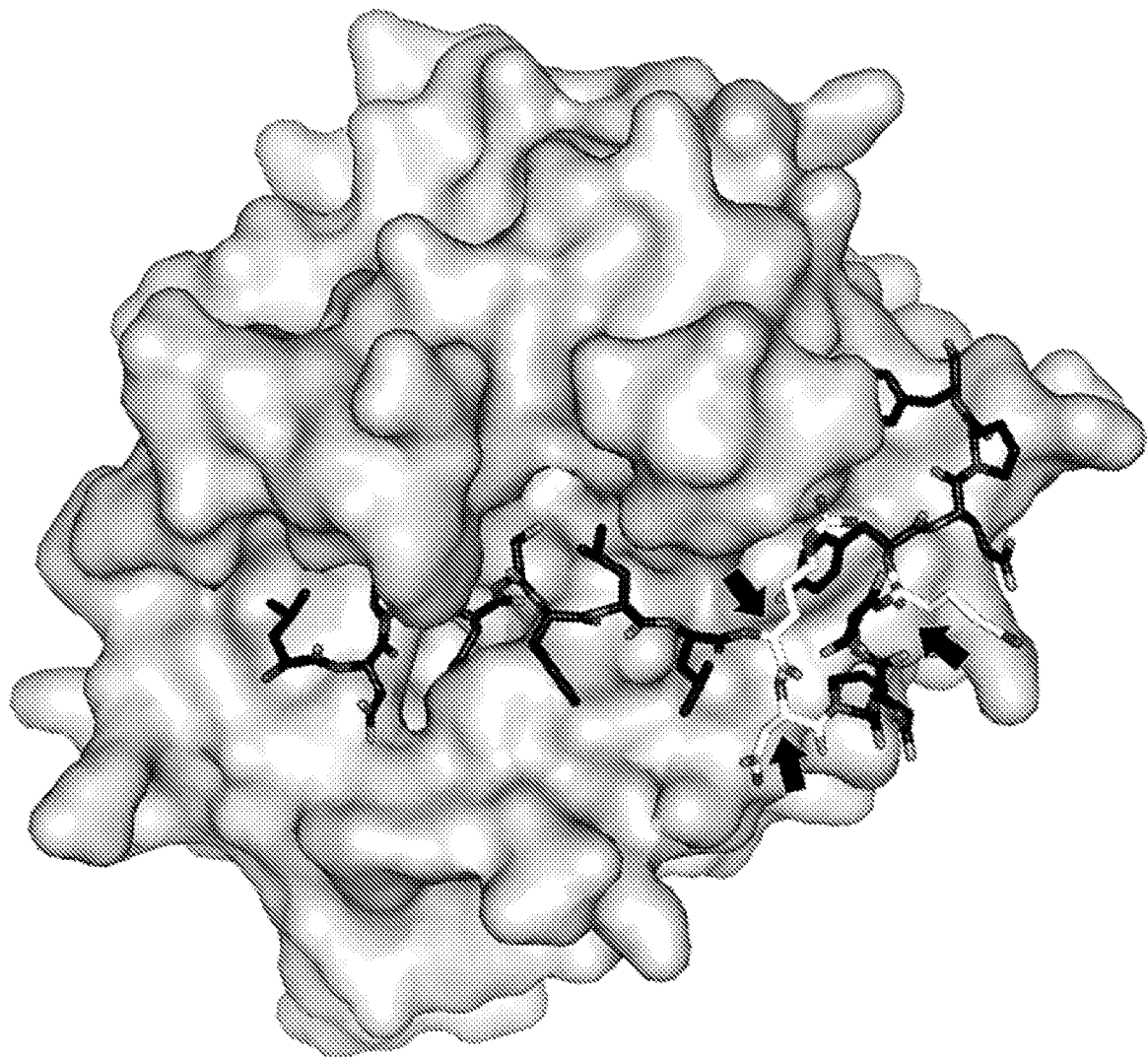
FIG. 3 shows the crystal structure of the protease thrombin bound to its natural substrate protease activated receptor-1 (PAR-1) (PDB ID 3LU9). The substrate (black sticks) has extensive interactions with the enzyme, and this sequence of amino acids is useful for targeting. At positions where the substrate has fewer interactions with the enzyme, and at positions where the amino acid side chains of the substrate interact with solvent (indicated by arrows), modifications to the amino acid sequence of the substrate can be made with little impact on targeting specificity.
Figure 4:
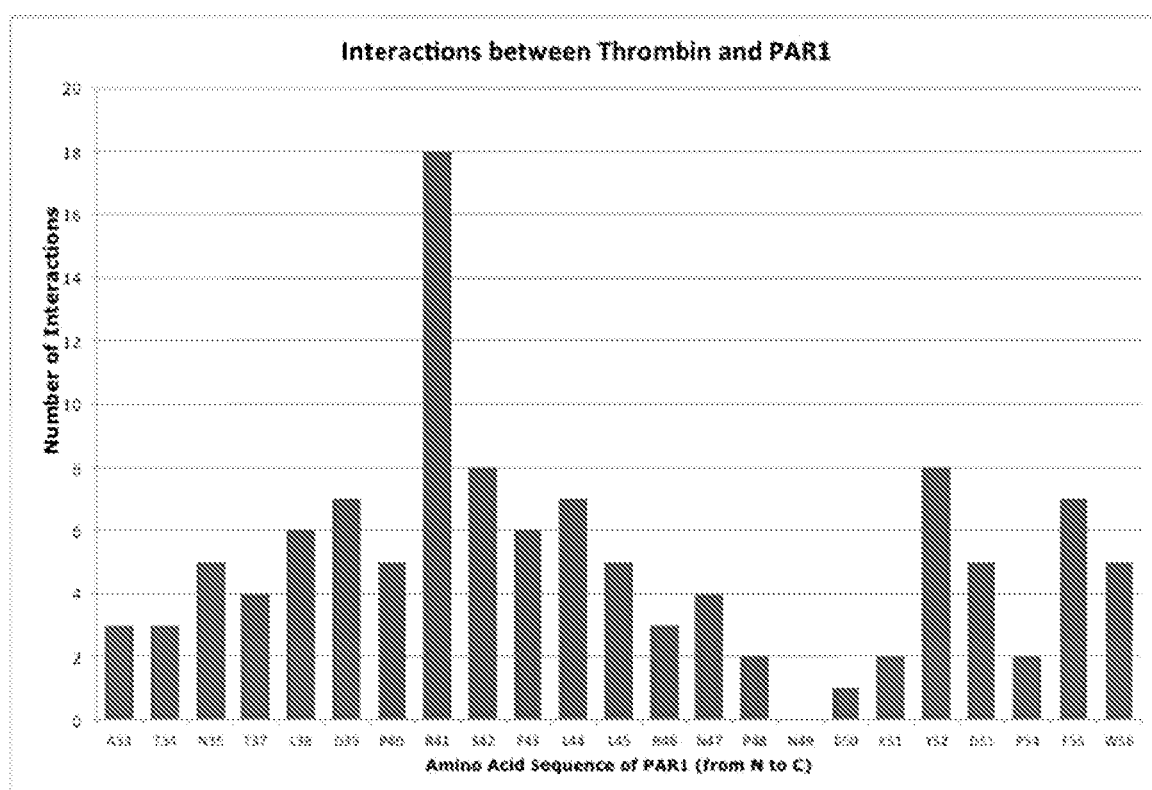
FIG. 4 is a graph showing the estimated number of interactions of the protease thrombin with each of the amino acid residues in its substrate PAR-1 (PDB ID 3LU9). Residues with more than five estimated interactions are likely to play an important role in substrate binding. Residues with fewer than five estimated interactions, e.g., R46, N47, and N49 (indicated in FIG. 3), may be altered to modulate the activity of the promolecule without adversely impacting substrate binding.
Figure 5:
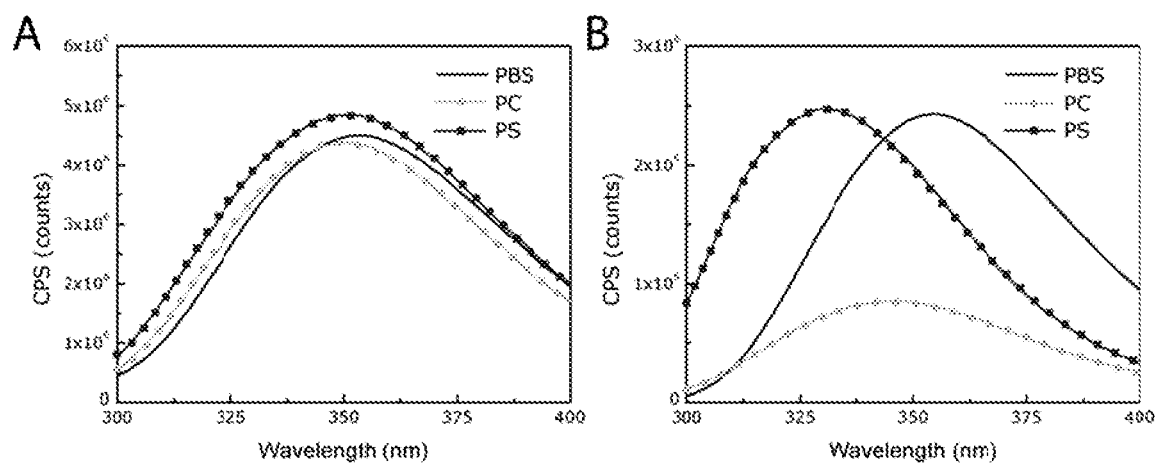
FIG. 5 is a series of graphs showing the intrinsic fluorescence of a single tryptophan residue in various promolecules of the present disclosure under different conditions. Panel A shows that prior to activation, the spectral properties of the promolecule do not change in the presence of liposomes composed of phosphatidylcholine (PC) or phosphatidylserine (PS) compared to buffer alone (PBS). Panel B shows that the activated form of the promolecule presents a marked blue shift in maximum wavelength, indicating that the cleavage product inserts into these membranes.
Figure 6:
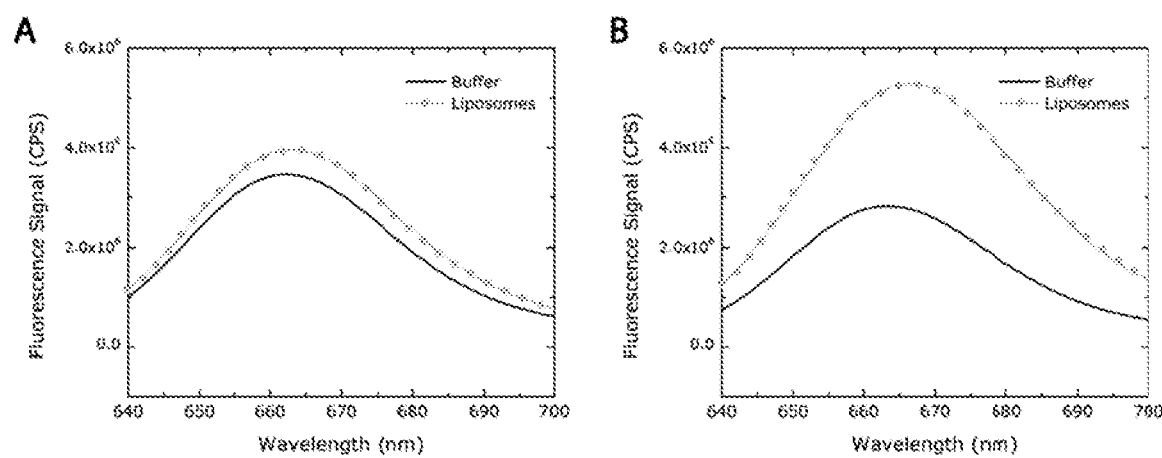
FIG. 6 shows the differential behavior of a promolecule of the present disclosure as evidenced by förster resonance energy transfer (FRET). Panel A shows that prior to activation, the promolecules do not associate closely enough with the liposomes to enable FRET from the 1,1'-dioctadecyl-3,3,3',3'-tetra-methylindo-carbocyanine perchlorate (DiL). Panel B shows that the activated form exhibits a significant FRET signal, indicating intimate association with DiL and the phospholipid membrane.
Figure 7:
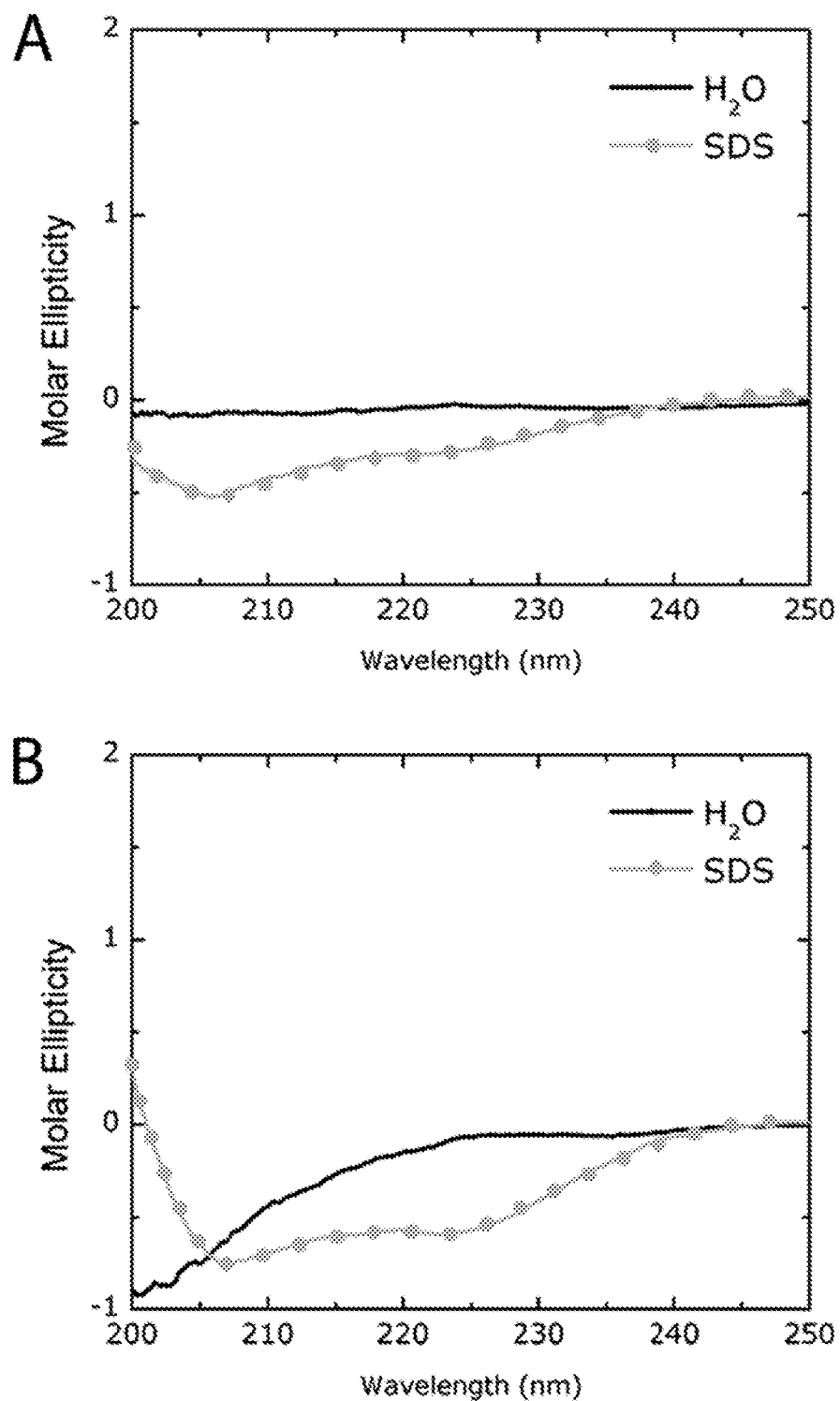
FIG. 7 shows the differential behavior of a promolecule of the present disclosure as evidenced by circular dichroism spectroscopy. Panel A shows that, when incubated with detergent micelles, the promolecule displays a weaker signature of alpha-helicity. Panel B shows that the activated form displays a stronger signature of alpha-helicity.
Figure 8:
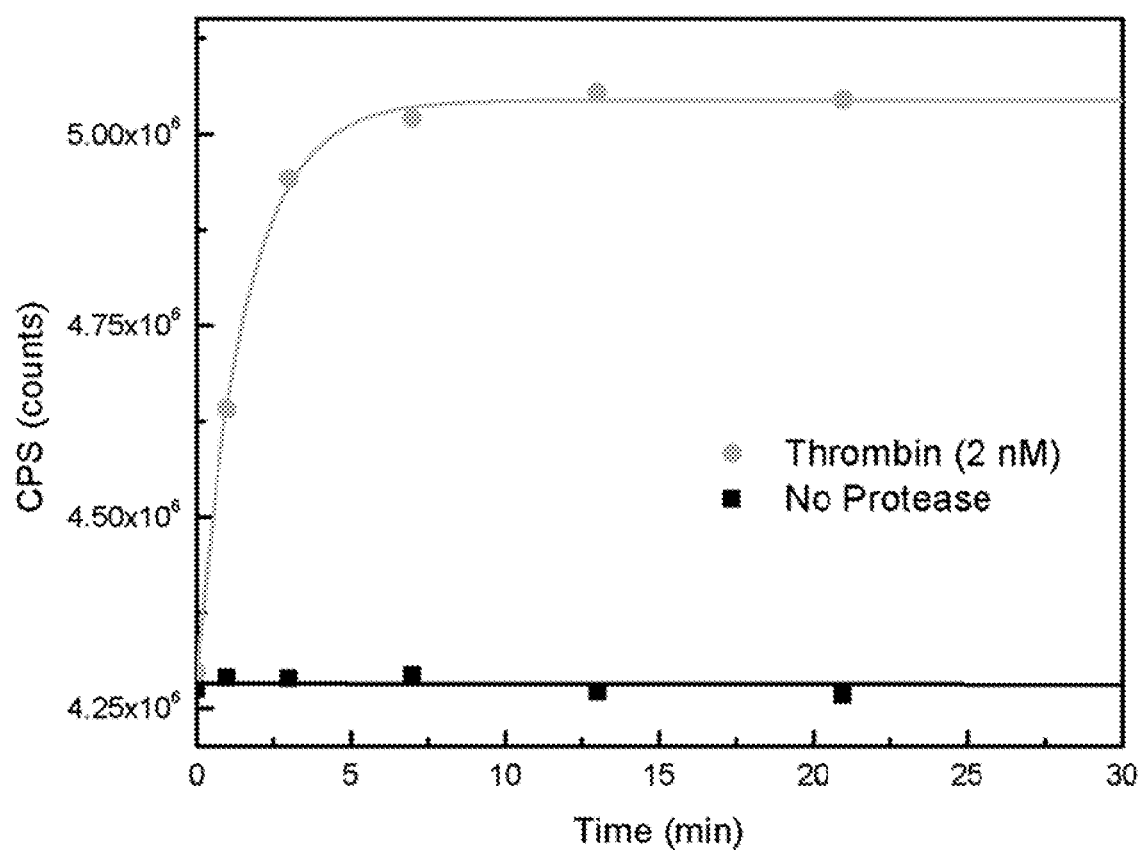
FIG. 8 is a graph showing the intrinsic fluorescence of a promolecule as a function of time in the presence or absence of the enzyme thrombin. Incubation of the promolecule with thrombin (2 nM) leads to efficient activation of the promolecule and a concomitant increase in interaction with liposomes. In the absence of enzyme, there are no changes in the spectral signature of the promolecule, indicating an absence of interaction with the liposomes.
Figure 9:
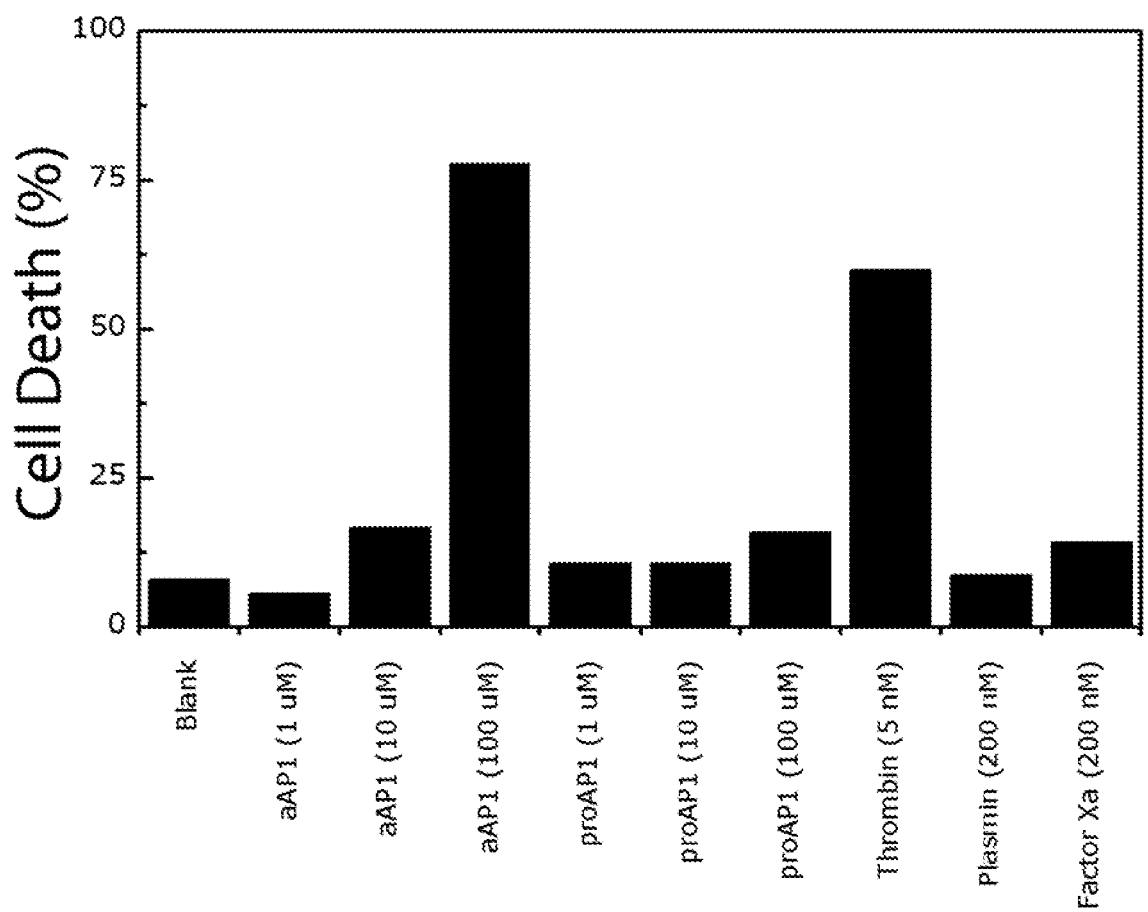
FIG. 9 shows the selective activation of a promolecule of the present disclosure as evidenced by the ability of Jurkat cells to exclude trypan blue dye. Cells (100,000) were incubated with the membrane-interacting peptide-containing cleavage product (aAP1) or the promolecule form (proAP1) of the compound at concentrations of 1, 10 or 100

Prior to cleavage of the composition at $X^2$, the composition acts as a promolecule that does not significantly or detectably associate with phospholipid bilayers. Cleavage of $X^2$ results in the formation of a cleavage product comprising portion A and a cleavage product comprising portion Z. Following cleavage of $X^2$, the cleavage product comprising portion A, now unconstrained by portion Z, is free to interact with a phospholipid bilayer (e.g., a cell membrane), and thus accumulate at a site associated with a cleavage-promoting environment (FIG. 2).

In some embodiments, the promolecules of the present disclosure are of the general structure, from N-terminus to C-terminus or from C-terminus to N-terminus:

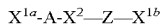

where

A, $X^2$, and Z are as described above; and $X^{1a}$ and $X^{1b}$ are optionally-present chemical handles that facilitate conjugation of various moieties to the compound.

Detection of cleavage products comprising portion A or portion Z can be accomplished by detection of a detectable moiety attached through chemical handle $X^{1a}$ or $X^{1b}$, or by other methods, e.g., detection using an antibody that specifically binds to an amino acid sequence of the cleavage product.

The various features of the compounds and methods of the present disclosure are described in more detail below.

The overall length of the intact structure $X^{1a}$-A-$X^2$—Z—$X^{1b}$ may vary based on the sizes of the individual portions that are used to assemble a given molecule. In some embodiments, the overall size of the intact structure is up to about 15 amino acids in length. In some embodiments, the overall length of the intact structure is up to about 20, up to about 30, up to about 40, up to about 50, up to about 60, up to about 70, up to about 80, up to about 90, up to about 100, or up to about 110 amino acids in length. In some embodiments, the overall length of the intact structure may be from about 15 to about 20, about 20 to about 30, about 30 to about 40, about 40 to about 50, about 50 to about 60, about 60 to about 70, about 70 to about 80, about 80 to about 90, about 90 to about 100, or about 100 to about 110 amino acids in length. The overall length of the intact structure is no more than about 115 amino acids in length.

The intact structure $X^{1a}$-A-$X^2$—Z—$X^{1b}$ may be referred to herein as a "promolecule." Portion A of the promolecule does not significantly interact with phospholipid bilayers due to the presence of portion Z in the promolecule. Without being held to theory, portion Z inhibits the phospholipid bilayer interacting properties of portion A by preventing portion A from forming an alpha-helical structure when portion A and portion Z are linked together by portion $X^2$. Following cleavage of $X^2$, portion Z is separated from portion A, allowing the cleavage product comprising portion A to undergo a conformational change such that at least portion A can form a regular structure such as that of an alpha-helical structure. In the alpha-helical conformation, portion A spontaneously interacts with phospholipid bilayers, e.g., by inserting into the phospholipid bilayer.

One of ordinary skill in the art will appreciate that the promolecules of the present disclosure can be adapted for use in a variety of settings, e.g., by providing for cleavable linkers that differ in conditions that provide for cleavage. In some embodiments, a promolecule has the structure, from N-terminus to C-terminus or from C-terminus to N-terminus, A-$X^2$—Z. In some embodiments, a promolecule has the structure, from N-terminus to C-terminus or from C-terminus to N-terminus, $X^{1a}$-A-$X^2$—Z. In some embodiments, a promolecule has the structure, from N-terminus to C-terminus or from C-terminus to N-terminus, A-$X^2$—Z—$X^{1b}$. In some embodiments, a promolecule has the structure, from N-terminus to C-terminus or from C-terminus to N-terminus, $X^{1a}$-A-$X^2$—Z—$X^{1b}$. As disclosed herein, the various embodiments of portions $X^{1a}$, A, $X^2$, Z, and $X^{1b}$ may be freely interchanged to form a molecule having any of the above-described features. In some embodiments, multiple copies of $X^{1a}$ or $X^{1b}$ may be incorporated to enhance detection sensitivity or pharmacological properties.

Promolecules of the present disclosure may be optionally modified to generally provide, e.g., a longer circulating half-life, focused activity within the cardiovascular system, protection from non-specific degradation, and/or greater sensitivity to certain imaging modalities. Such optional modifications include, e.g., conjugation of two or more promolecules to a central polyethylene glycol molecule to a form a dendrimer or amidation of the N- and/or C-termini of the promolecule to mitigate unwanted proteolysis.

Properties of Activatable Membrane-Interacting Peptides

As described above, the promolecules of the present disclosure have the general structure $X^{1a}$-A-$X^2$—Z—$X^{1b}$. In order to prevent the membrane-interacting portion (portion A) from interacting with cell membranes prior to activation, the promolecules are designed to have an isoelectric point (pI) of 7 or lower. The isoelectric point is the pH at which the net charge on a peptide molecule is zero. The pI of the full-length promolecules of the present disclosure can be modulated by adjusting the pI of one or more of the individual portions $X^{1a}$, A, $X^2$, Z, or $X^{1b}$ that make up the promolecule, or by chemically modifying any or all portions of the compound (e.g., by phosphorylation or sulfation to impart additional negative charge).

The pI of a peptide can be modulated by substituting, eliminating, or introducing amino acid residues in order to change the overall net charge of the peptide. Decreasing the net charge of a peptide reduces its pI value. For example, eliminating one or more positively charged amino acid residues (e.g. K, R, or H) or replacing such residues with uncharged or negatively charged residues reduces the pI value of the peptide.

The pI of a given peptide can be readily determined by using a computer algorithm for pI estimation (e.g., Protein Calculator, Scripps Institute). Such computer algorithms are readily available to the public via the internet and can determine a theoretical pI value for a peptide based on its amino acid sequence. Promolecules of the present disclosure are designed to have a theoretical pI value less than or equal to 7.

The promolecules of the present disclosure are generally designed to have an overall net charge preferably less than or equal to about zero. This can be accomplished, for example, by substituting, eliminating, or introducing various amino acid residues in the polypeptide sequences of portion A or portion Z, or by introducing charged moieties to portion Z, to neutralize the overall charge of the promolecule. Charged amino acid residues or moieties that are introduced to neutralize the charge of other amino acid residues or chemical moieties are placed as close as possible to one another in order to maximize charge-cancelling effects, e.g., a distance of no more than about 40 Angstroms. In some embodiments, promolecules of the present disclosure need not have an overall charge of less than or equal to about zero if, for example, the propensity of the membrane interaction segment to spontaneously insert into phospholipid membranes is limited.

Cargo moieties that are optionally conjugated to the promolecules of the present disclosure may be charged, and therefore may impact the pI value and the overall net charge of a promolecule, thus impacting the restriction in membrane-interacting activity. The charge on a particular cargo moiety added to a promolecule will generally cancel or neutralize the overall net charge of the promolecule that it is conjugated to and reduce the overall pI to a value of seven or lower. For example, a promolecule having an overall net charge of +1 could be conjugated to a detectable moiety having a charge of −1 to produce a molecule having an overall net charge of zero. Water soluble fluorescent dyes, such as those in the cyanine dye family, including Cy3, Cy5, and Cy7, are particularly useful in this regard due to their zwitterionic nature from two negatively-charged sulphate groups and a tertiary amine group. Metal chelating moieties, such as 1,4,7,10-tetraazacyclododecane-1,4,7,10-tetraacetic acid (DOTA) or diethylene triamine pentaacetic acid (DTPA) capable of binding radioisotopes Gallium-68 or Technetium-99m are zwitterionic as well, bearing multiple positively- and negatively-charged moieties. Metal binding to DOTA or DTPA occurs through the amine groups, thus allowing these entities to impart a charge of up to −4.

Portion Z's ability to inhibit or prevent portion A from interacting with phospholipid bilayers can also be modulated by changing the overall length of portion Z. This can be done, for example, by adding amino acid residues to portion Z, or by conjugating a molecule, such as a water-soluble polymer, to portion Z. In some embodiments, negatively charged amino acids or similar chemical modifications, such as phosphates or sulphate moieties, are added to portion Z.

In some embodiments, polyethylene glycol is conjugated to portion Z in order to increase the length of portion Z and enhance its ability to inhibit portion A from interacting with cell membranes prior to activation. In some embodiments, whole proteins (e.g. albumin) may be conjugated to portion Z. In certain embodiments, a polymer or protein that is conjugated to portion Z may also increase the circulating half-life of the promolecule. In some embodiments, the promolecules of the present disclosure may be conjugated to polymers having branched, dendrimeric, or otherwise polyvalent architecture.

Portion A—Membrane-Interacting Peptides

The membrane-interacting peptides of the present disclosure comprise amino acid sequences that are capable of forming alpha-helical structures, e.g., upon contacting an environment with a lower dielectric constant than water. Following cleavage of $X^2$, the cleavage product comprising portion A comprises an alpha-helical structure that is capable of inserting into a phospholipid bilayer in the vicinity of the cleavage-promoting environment. Without being held to theory, the alpha-helical structure of portion A may be present in the molecule prior to cleavage but, due to constraint by portion Z, is unable to insert into a phospholipid bilayer. The presence of portion A and/or portion Z constrains portion A such that portion A does not form an alpha-helical structure sufficient to allow for significant or detectable insertion into a phospholipid bilayer.

An alpha helix is a common motif in the secondary structure of proteins, and generally comprises a right-handed coiled or spiral conformation that is stabilized by hydrogen bonds in which the N—H group of a first amino acid residue forms a hydrogen bond with the C=O group of an amino acid residue located four residues away in the polypeptide chain. A typical alpha helix comprises approximately 3.6 amino acid residues per turn of the helix, and is a tightly-packed structure. The side chains of the amino acid residues that make up an alpha helix face the outside of the helix. Different amino acid sequences have different propensities for forming alpha helices due, in part, to the differing chemical properties of the amino acid side chains.

As described above, promolecules of the present disclosure generally comprise a membrane-interacting peptide portion A. Portion A may be derived from a naturally-occurring polypeptide, or may be a variant of a naturally-occurring polypeptide. The overall length of portion A can be, for example, about 5 up to about 10 amino acids, or can be up to about 15, up to about 20, up to about 25, or up to about 30 amino acids. Portion A may range in size from about 5 to about 10 amino acids in length, or may be about 10 to about 15, about 15 to about 20, about 20 to about 25, or about 25 to about 30 amino acids in length. Portion A is no longer than about 35 amino acid residues in length.

Membrane-interacting peptides generally comprise a plurality of nonpolar, hydrophobic amino acid residues (e.g., alanines, valines, leucines, isoleucines, phenylalanines, tryptophans, methionines, or prolines), but may comprise other types of amino acids as well, such as polar uncharged, polar acidic, and/or polar basic amino acid residues. In general, the membrane-interacting peptides of the present disclosure comprise fewer than 5 polar basic amino acid residues. In some embodiments, the amino acid sequence of portion A comprises multiple regions of two to three contiguous nonpolar hydrophobic amino acid residues interspersed with regions of one to two contiguous polar uncharged, polar acidic, or polar basic residues. After cleavage of $X^2$, portion A undergoes a conformational change, typically forming an alpha-helical structure that readily interacts with cell membranes (e.g., membranes present in the cells of eukaryotic, prokaryotic or archael organisms, or artificial membranes of detergent micelles or liposomes of varying compositions, including synthetic polymers).

Antimicrobial Peptides

Antimicrobial peptides that elicit their effects through membrane interaction are well known in the art, and include examples such as the temporin family of proteins, which can be naturally obtained from the skin of frogs belonging to the *Rana temporaria* species. Antimicrobial peptides generally comprise fewer than about 30 amino acid residues and, under physiological conditions, contain alpha-helical structures having nonpolar hydrophobic amino acid residues that facilitate their interaction with the phospholipid bilayers of cell membranes. Such interactions may generally include types ranging from structured barrel-stave pores to broadly-defined detergent-like behavior. In some embodiments of the present disclosure, an amino acid sequence of a naturally-occurring antimicrobial peptide is utilized as a membrane-interacting peptide. In other embodiments, a membrane-interacting peptide that comprises modifications relative to a naturally-occurring antimicrobial peptide, e.g., elimination, introduction, or substitution of one or more amino acid residues, addition of chemical modifications such as disulfide bonds, or other chemical modifications (e.g., amidation), is utilized as a membrane-interacting peptide. In other embodiments, the peptide sequence is capable of spontaneous membrane interaction and/or insertion, but is not associated with membrane disrupting activity.

Examples of antimicrobial peptides are provided below.

Modifications to Membrane-Interacting Peptides

Antimicrobial peptides or portions thereof may be incorporated into the compounds of the present disclosure in their naturally-occurring form, or may be modified to alter their chemical properties and adapt such for a desired use. For example, the membrane-interaction potential of antimicrobial peptides may be strengthened or weakened by, e.g., adding, eliminating or substituting certain amino acid residues in the protein sequence. Such additions, eliminations, or substitutions can be made, e.g., to introduce charged amino acid residues, to eliminate charged amino acid residues, to introduce hydrophobic amino acid residues, to eliminate hydrophobic amino acid residues, etc.

In some embodiments, an antimicrobial peptide sequence may be altered by chemically modifying the peptide with disulfide bonds or other chemical modifications (e.g. amidation). Many antimicrobial peptides are naturally produced with such modifications to improve the potency of their interactions with phospholipid membranes and resistance to proteolysis.

Temporins

In some embodiments, portion A comprises a protein from the Temporin family. Proteins in the Temporin family generally range from about 10 up to about 14 amino acids in length. The consensus sequence for the Temporin family of proteins showing the most abundant amino acid found at each position is: FLP(I/L)IASLL(S/G)KLL (SEQ ID NO: 1). The consensus sequence for the Temporin family of proteins showing the general amino acid type found at each position is: $X^aX^bX^cX^dX^eX^fY^aX^gX^hY^bY*X^iX^j$, where $X^a$, $X^b$, $X^c$, $X^d$, $X^e$, $X^f$, $X^g$, $X^h$, $X^i$, and $X^j$ are hydrophobic amino acid residues, $Y^a$ and $Y^b$ are hydrophilic amino acid residues, and $Y*$ is a charged amino acid residue. The table below shows the amino acid sequences of several Temporin and Temporin-like peptides that are useful in the promolecules and methods of the present disclosure.

As described above, antimicrobial peptide sequences may be altered by eliminating or substituting one or more of the amino acid residues. For example, in some embodiments, a membrane-interacting peptide comprises Temporin-L, whose amino acid sequence is FVQWFSKFLGRIL (SEQ ID NO: 2). In other embodiments, a membrane-interacting peptide comprises a derivative of Temporin-L having the amino acid sequence FVQWFSKFLGKLL (SEQ ID NO: 3), wherein amino acid residues R and I at positions 11 and 12 of the Temporin-L sequence have been replaced with amino acid residues K and L, respectively.

TABLE 1

Amino acid sequences of Temporin and Temporin-like peptides thirteen amino acids in length. Longer and shorter members of the family have also been described but are not included in this table.

| Peptide Name | Amino Acid Sequence |
|---|---|
| Temporin-A (SEQ ID NO: 61) | — F L P L I G R V L S G I L — |
| Temporin-B (SEQ ID NO: 62) | — L L P I V G N L L K S L L — |
| Temporin-C (SEQ ID NO: 63) | — L L P I L G N L L N G L L — |
| Temporin-D (SEQ ID NO: 64) | — L L P I V G N L L N S L L — |
| Temporin-E (SEQ ID NO: 65) | — V L P I I G N L L N S L L — |
| Temporin-F (SEQ ID NO: 66) | — F L P L I G K V L S G I L — |
| Temporin-G (SEQ ID NO: 67) | — F F P V I G R I L N G I L — |
| Temporin-H (SEQ ID NO: 68) | — L S P — — — N L L K S L L — |
| Temporin-K (SEQ ID NO: 69) | — L L P — — — N L L K S L L — |
| Temporin-L (SEQ ID NO: 70) | — F V Q W F S K F L G R I L — |
| Temporin-1 Ca (SEQ ID NO: 71) | — F L P F L A K I L T G V L — |
| Temporin-1 Cb (SEQ ID NO: 72) | — F L P L F A S L I G K L L — |
| Temporin-1 Cc (SEQ ID NO: 73) | — F L P F L A S L L T K V L — |
| Temporin-1 Cd (SEQ ID NO: 74) | — F L P F L A S L L S K V L — |
| Temporin-1 Ce (SEQ ID NO: 75) | — F L P F L A T L L S K V L — |
| Temporin-1 Ga (SEQ ID NO: 76) | S I L P T I V S F L S K V F — |
| Temporin-1 Gb (SEQ ID NO: 77) | S I L P T I V S F L S K F L — |
| Temporin-1 Gc (SEQ ID NO: 78) | S I L P T I V S F L T K F L — |
| Temporin-1 Gd (SEQ ID NO: 79) | F I L P L I A S F L S K F L — |

TABLE 1-continued

Amino acid sequences of Temporin and Temporin-like peptides thirteen amino acids in length. Longer and shorter members of the family have also been described but are not included in this table.

| Peptide Name | Amino Acid Sequence |
|---|---|
| Temporin-1 La (SEQ ID NO: 80) | — V L P L I S M A L G K L L — |
| Temporin-1 Lb (SEQ ID NO: 81) | N F L G T L I N L A K K I M — |
| Temporin-1 Lc (SEQ ID NO: 82) | — F L P I L I N L I H K G L L |
| Temporin-1 P (SEQ ID NO: 83) | — F L P I V G K L L S G L L — |
| Ranatuerin-5 (SEQ ID NO: 84) | — F L P I / A S L L G K Y L — |
| Ranatuerin-6 (SEQ ID NO: 85) | — F I S A I A S M L G K F L — |
| Ranatuerin-7 (SEQ ID NO: 86) | — F L S A I A S M L G K F L — |
| Ranatuerin-8 (SEQ ID NO: 87) | — F I S A I A S F L G K F L — |
| Ranatuerin-9 (SEQ ID NO: 88) | F L F P L I T S F L S K V L — |
| Peptide A1 (SEQ ID NO: 89) | — F L P A I A G I L S Q L F — |
| Peptide B9 (SEQ ID NO: 90) | — F L P L I A G L L G K L F — |

In some embodiments of the present disclosure, a membrane-interacting peptide comprises a Temporin or a Temporin-like peptide listed in Table 1, or a conservative amino acid substitution thereof. In some embodiments of the present disclosure, a membrane-interacting peptide comprises the sequence of Temporin-L (FVQWFSKFLGRIL) (SEQ ID NO: 2), or a conservative amino acid substitution thereof.

Protonectin

In some embodiments of the present disclosure, a membrane-interacting peptide comprises Protonectin, having the amino acid sequence ILGTILGLLKGL (SEQ ID NO: 4), or a conservative amino acid substitution thereof.

Japonicins

In some embodiments, a membrane-interacting peptide may comprise a Japonicin or a Japonicin-like peptide listed in Table 2, or a conservative amino acid substitution thereof. In some embodiments of the present disclosure, a membrane-interacting peptide comprises the sequence of Japonicin-1 (FFPIGVFCKIFKTC) (SEQ ID NO: 5), or a conservative amino acid substitution thereof. Japonicins are naturally obtainable from the skin of the Japanese brown frog *Rana japonica* and range in length from about 14 up to about 21 amino acid residues. The table below shows the amino acid sequences of several Japonicin and Japonicin-like peptides that are useful in the promolecules and methods of the present disclosure.

TABLE 2

Amino acid sequences of Japonicin and Japonicin-like peptides.

| Peptide Name | Amino Acid Sequence |
|---|---|
| Japonicin-1 (SEQ ID NO: 5) | F — — — — — F P I G V F C K I F K — T C |
| Japonicin-1CDYa (SEQ ID NO: 92) | F — — — — — F P L A L L C K V F K — K C |
| Japonicin-1Npa (SEQ ID NO: 93) | F — — — — — L L F P L M C K I Q G — K C |
| Japonicin-1Npb (SEQ ID NO: 94) | F — — — — — V L P L V M C K I L R — K C |
| Japonicin-2 (SEQ ID NO: 95) | F G L P M L S I L P K A L C I L L K R K C |

In some embodiments of the present disclosure, a membrane-interacting peptide comprises a Japonicin or a Japonicin-like peptide listed in Table 2, or a conservative amino acid substitution thereof.

Additional Peptides

In addition to the peptides described above, promolecules of the present disclosure may comprise a membrane-interacting peptide listed in the following table, or a conservative amino acid substitution thereof. In some embodiments, the peptides listed in the table below comprise N- and/or C-terminal modifications that may modulate their activity.

TABLE 3

Peptides suitable for use in portion A.

| Peptide Name | Amino Acid Sequence | SEQ ID NO: |
|---|---|---|
| Combi-1 | RRWWRF | SEQ ID NO: 6 |
| Combi-2 | FRWWHR | SEQ ID NO: 7 |
| Jelleine-1 | PFKLSLHL | SEQ ID NO: 8 |
| Jelleine-2 | TPFKLSLHL | SEQ ID NO: 9 |
| Temporin-SHf | FFFLSRIF | SEQ ID NO: 10 |
| Modified Temporin-SHF | FFWLSKIF | SEQ ID NO: 11 |
| Jcpep7 | KVFLGLK | SEQ ID NO: 12 |
| Myxinidin | GIHDILKYGKPS | SEQ ID NO: 13 |
| 1T51 | ILGKIWEGIKSLF | SEQ ID NO: 14 |
| Mastoparan B | LKLKSIVSWAKKVL | SEQ ID NO: 15 |
| K4 | KKKKPLFGLFFGLF | SEQ ID NO: 16 |
| Agelaia-MP | INWLKLGKAIIDAL | SEQ ID NO: 17 |

Portion Z—Membrane-Interaction Inhibitory Peptide

Compounds of the present disclosure generally comprise portion Z, which inhibits or prevents portion A from interacting with phospholipid bilayers when linked to portion A through portion $X^2$. In some embodiments, portion Z also facilitates the interaction of the promolecule with a target enzyme.

Portion Z is generally a polypeptide comprising about 2 up to about 15 amino acid residues in length. In some embodiments, portion Z is up to about 5, up to about 10, up to about 15, up to about 20, up to about 25, up to about 30, up to about 35, up to about 40, up to about 45, or up to about 50 amino acids in length. In some embodiments, portion Z ranges from about 2 to about 5, about 5 to about 10, about 10 to about 15, about 15 to about 20, about 20 to about 25, about 25 to about 30, about 30 to about 35, about 35 to about 40, about 40 to about 45, or about 45 to about 50 amino acids in length. Portion Z is no more than about 55 amino acids in length.

Portion Z may comprise any type of amino acid residue. In some embodiments, portion Z may optionally comprise a detectable moiety to facilitate detection of portion Z following cleavage of $X^2$.

Recognition Domains

Portion Z may be designed to aid in modulating the cleavage of $X^2$ and subsequent activation of portion A. In some embodiments, portion Z comprises an amino acid sequence that can be bound by an enzyme that cleaves $X^2$. In certain embodiments, recognition of a specific amino acid sequence in portion Z may be required before an enzyme is able to cleave $X^2$ and activate the promolecule. Some of the amino acid residues in portion Z may be adjusted to modulate the activity of the promolecule without changing the specificity of interaction between portion Z and the target enzyme. The crystal structure of the enzyme thrombin bound to portion Z of a promolecule is shown in FIG. 3. As shown in FIG. 4, the number of interactions between certain amino acid residues in portion Z and a target enzyme may be used to determine which amino acid residues can altered without impacting binding of the enzyme to portion Z.

In some embodiments, portion Z comprises an amino acid sequence derived from naturally occurring physiologic substrates of the enzymatic activator. In some embodiments, portion Z comprises an amino acid sequence derived from the analysis of screening of combinatorial peptide libraries that may or may not share similarity to physiologic substrates of the enzymatic activator.

In some embodiments, portion Z comprises the exosite recognition sequence of protease-activated receptor-1 (PAR-1), which is specifically recognized by the enzyme thrombin.

In some embodiments, portion Z comprises the PAR-1 exosite recognition sequence SFLLRNPNDKYEPFW (SEQ ID NO: 18).

In some embodiments, portion Z comprises the exosite recognition sequence of protease-activated receptor-2 (PAR-2), which is specifically recognized by the enzyme TMPRSS2. In some embodiments, portion Z comprises the PAR-2 exosite recognition sequence KVDGTSHVTGDDD (SEQ ID NO: 20).

$X^2$—Cleavable Linkers

In the promolecules of the present disclosure, portion A is linked to portion Z through cleavable linker $X^2$. In some embodiments, $X^2$ comprises a linker that links portion A to portion Z with a single chemical bond. In other embodiments, $X^2$ comprises a chimeric linker that links portion A to portion Z through two or more different chemical bonds.

Cleavage of $X^2$ produces two cleavage products: a first cleavage product containing portion A and a second cleavage product containing portion Z. In general, $X^2$ is cleavable under a pre-selected physiological condition. $X^2$ can be selected so that the promolecule is selectively cleaved when exposed to an environment associated with a condition to be diagnosed or detected.

For example, $X^2$ may comprise a chemical bond that is susceptible to cleavage under conditions found in an extracellular environment, such as acidic conditions, which may be found near cancerous cells and tissues, or reducing environments, as may be found near hypoxic or ischemic cells and tissues. $X^2$ may comprise a chemical bond that is subject to cleavage by proteases or other enzymes found on the surface of cells or released near cells having a condition to be diagnosed or detected, such as diseased, apoptotic or necrotic cells and tissues, or by other conditions or factors. An acid-labile linker may be, for example, a cis-aconitic acid linker. Other examples of pH-sensitive linkages include acetals, ketals, activated amides such as amides of 2,3-dimethylmaleamic acid, vinyl ether, other activated ethers and esters such as enol or silyl ethers or esters, imines, iminiums, enamines, carbamates, hydrazones, and other linkages.

$X^2$ may comprise an amino acid or a peptide. When $X^2$ comprises a peptide, the peptide may be of any suitable length, such as, for example, about 2 up to about 5, up to about 10, up to about 15, up to about 20, up to about 25, or up to about 30 amino acid residues in length. In some embodiments, $X^2$ is about 2 to about 5, about 5 to about 10, about 10 to about 15, about 15 to about 20, about 20 to about 25, or about 25 to about 30 amino acids in length. $X^2$ is no longer than about 35 amino acids in length. A cleavable peptide may include an amino acid sequence recognized and cleaved by a protease, so that proteolytic action of the protease cleaves $X^2$.

Enzymatically-Cleavable Linkers

The design of $X^2$ for cleavage by specific conditions, such as by a specific enzyme, allows targeting of activation to a specific location where such conditions are found. Thus, one way that compounds of the present disclosure provide specific targeting to desired cells, tissues, or regions is by the design of the linker portion $X^2$ to be cleaved by conditions near such targeted cells, tissues, or regions. After cleavage of $X^2$, cleavage products A and Z are formed, and portion A is free to interact with phospholipid bilayers, such as cell membranes, in the vicinity of activation.

In some embodiments, $X^2$ is an enzymatically-cleavable peptide having the amino acid sequence PR. This amino acid sequence is specifically cleaved by the enzyme thrombin. In some embodiments, $X^2$ is an enzymatically-cleavable peptide having the amino acid sequence PLGLAG (SEQ ID NO: 24). This amino acid sequence is specifically cleaved by the enzyme matrix metalloproteinase-2 (MMP-2). In some embodiments, $X^2$ is an enzymatically-cleavable peptide having the amino acid sequence PLFAEP (SEQ ID NO: 25), which is cleaved by the enzyme calpain-1. In some embodiments, $X^2$ is an enzymatically-cleavable peptide having the amino acid sequence GLGSEP (SEQ ID NO: 26), which is cleaved by the enzyme calpain-2. In some embodiments, $X^2$ is an enzymatically-cleavable peptide having the amino acid sequence KSRAEDE (SEQ ID NO: 28), which is cleaved by the enzyme matriptase. In some embodiments, $X^2$ is an enzymatically-cleavable peptide having the amino acid sequence LQRALE (SEQ ID NO: 29), which is cleaved by the enzyme MASP-2. In some embodiments, $X^2$ is an enzymatically-cleavable peptide having the amino acid sequence LLRSLIG (SEQ ID NO: 30), which is cleaved by the enzyme TMPRSS2. In some embodiments, $X^2$ is an enzymatically-cleavable peptide having the amino acid sequence VELLYLV (SEQ ID NO: 31), which is cleaved by the secreted aspartyl proteases from a variety of species of Candida and Aspergillus.

Linkers Cleavable by Thrombin or Other Clotting-Related Enzymes

In some embodiments, $X^2$ linkers are susceptible to cleavage by the enzyme thrombin, which is an enzyme involved with the process of blood clot formation. Thrombin is present on the surface of cells in areas of active clotting, and may therefore be used to cleave $X^2$ linkers and target detection of active clotting using the promolecules of the present disclosure. Thrombin cleaves $X^2$ linkers that contain the amino acid sequence PR, and also binds to the PAR-1 recognition sequence, which may be used to further control cleavage of $X^2$ linkers by this enzyme. Promolecules of the present disclosure are cleaved by thrombin when an $X^2$ linker comprises the amino acid sequence PR, and when portion Z comprises the PAR-1 recognition sequence.

In some embodiments, $X^2$ linkers may be cleaved by other agents associated with the clotting process. For example, Factor Xa cleaves linkers with the amino acid sequence LEGR (SEQ ID NO: 32). Factor IXa cleaves linkers with the amino acid sequence LVVR (SEQ ID NO: 33). Activated protein C cleaves linkers with the amino acid sequence LVKR (SEQ ID NO: 36). Factor VIIa cleaves linkers with the amino acid sequence QLTR (SEQ ID NO: 37).

Matriptase-Cleavable Linkers

In some embodiments, $X^2$ linkers are susceptible to cleavage by the enzyme matriptase, which is an enzyme that may be over-expressed in infiltrating breast carcinomas. Matriptase may therefore be used to cleave $X^2$ linkers and target detection of cancer, e.g. breast cancer, using the promolecules of the present disclosure. Matriptase cleaves $X^2$ linkers that contain the amino acid sequence KSR.

MMP-Cleavable Linkers

In some embodiments, $X^2$ linkers are susceptible to cleavage by matrix metalloproteinases (MMPs). Thus, molecules having features of the present disclosure are able to direct membrane interaction of portion A with specific cells, tissues, or regions having active MMPs in the extracellular environment.

For example, an $X^2$ linker that includes the amino acid sequence PLGLAG (SEQ ID NO: 24) may be cleaved by the metalloproteinase enzyme MMP-2 (a major MMP in cancer and inflammation). Cleavage of such an $X^2$ linker occurs between the central G and L residues, resulting in separation of portions A and Z, which in turn allows portion A to interact with phospholipid bilayers in the vicinity. Other examples of such $X^2$ linkers include the amino acid sequence AAA, which is cleavable by the enzyme MMP-11, the amino acid sequence GPSG (SEQ ID NO: 38), which is cleavable by the enzyme MMP-8, and the amino acid sequence GPAG (SEQ ID NO: 39), which is cleavable by the enzyme MMP-9.

$X^2$ linkers of the present disclosure may be designed to be preferentially sensitive to particular subclasses of MMPs, or to individual members of the large MMP family of proteinases. For example, in some embodiments, $X^2$ peptide sequences designed to be cleaved by membrane-anchored MMPs are utilized because their activity remains localized to the outer surface of the expressing cell.

Calpain-Cleavable Linkers

In some embodiments, $X^2$ linkers are susceptible to cleavage by enzymes associated with areas of necrosis. Such an $X^2$ linker includes one that is susceptible to cleavage by calpains (e.g. calpain-1 or calpain-2) or other proteases that may be released from necrotic cells. Such cleavage of $X^2$ by calpains would release portion A from portion Z, allowing portion A to interact with the membranes of diseased cells and neighboring cells in the vicinity of necrotic cells or tissues.

For example, in some embodiments, $X^2$ is an enzymatically-cleavable peptide having the amino acid sequence PLFAEP (SEQ ID NO: 25), which is cleaved by the enzyme calpain-1. In areas where calpain-1 is present (such as necrotic areas), $X^2$ is cleaved, releasing portion A from portion Z and allowing portion A to interact with cell membranes in the vicinity.

In some embodiments, $X^2$ is an enzymatically-cleavable peptide having the amino acid sequence GLGSEP (SEQ ID NO: 26), which is cleaved by the enzyme calpain-2. In areas where calpain-2 is present (e.g., necrotic areas), $X^2$ is cleaved, releasing portion A from portion Z and allowing portion A to interact with cell membranes in the vicinity.

In some embodiments, $X^2$ is an enzymatically-cleavable peptide having the amino acid sequence VGVF (SEQ ID NO: 27), which is cleaved by the enzyme calpain-3.

Other Enzymatically-Cleavable Linkers

In some embodiments, $X^2$ is an enzymatically-cleavable linker having the amino acid sequence SSLY (SEQ ID NO: 40), which is cleaved by Prostate Specific Antigen (KLK3). In some embodiments, $X^2$ is an enzymatically-cleavable linker having the amino acid sequence ASN, which is cleaved by the enzyme Legumain. In some embodiments, $X^2$ is an enzymatically-cleavable linker having the amino acid sequence RR, which is cleaved by the enzyme Cathepsin B. In some embodiments, $X^2$ is an enzymatically-cleavable linker having the amino acid sequence SSR, which is cleaved by Urokinase-type plasminogen activator. In some embodiments, $X^2$ is an enzymatically-cleavable linker having the amino acid sequence LLRSLIG (SEQ ID NO: 30), which is cleaved by the enzyme TMPRSS2. In some embodiments, $X^2$ is an enzymatically-cleavable linker having the amino acid sequence DDDDK (SEQ ID NO: 41), which is cleaved by the enzyme enteropeptidase. In some embodiments, $X^2$ is an enzymatically-cleavable linker having the amino acid sequence KKLK (SEQ ID NO: 42), which is cleaved by the enzyme Cruzain. In some embodiments, $X^2$ is an enzymatically-cleavable linker having the amino acid sequence QRQR (SEQ ID NO: 43), which is cleaved by the enzyme Complement Clr. In some embodiments, $X^2$ is an enzymatically-cleavable linker having the amino acid sequence NISH (SEQ ID NO: 44), which is cleaved by the enzyme C5a peptidase. In some embodiments, $X^2$ is an enzymatically-cleavable linker having the amino acid sequence VELLYLV (SEQ ID NO: 31), which is cleaved by the enzyme Aspartyl peptidase. In some embodiments, $X^2$ is an enzymatically-cleavable linker having the amino acid sequence PLG, which is cleaved by the enzyme Cathepsin L. In some embodiments, $X^2$ is an enzymatically-cleavable linker having the amino acid sequence RSKR (SEQ ID NO: 45), which is cleaved by the enzyme Protein Convertase 5. A summary of the above-listed enzymes, their cleavage sequences, and their associated conditions is provided in Table 3.

Linkers Susceptible to Cleavage Under Reducing Conditions $X^2$ linkers that are susceptible to cleavage under reducing conditions provide for cleavage of promolecules of the present disclosure in regions having reduced oxygen concentration, such as regions surrounding cancer cells and cancerous tissues, infarct regions, and other hypoxic regions. Examples of cleavable linkers susceptible to cleavage under hypoxic conditions include those containing a disulfide bond. In a hypoxic environment, free thiols and other reducing agents become available extracellularly, while the oxygen that normally maintains the extracellular environment in an oxidizing state is depleted. This shift in the redox balance promotes reduction and cleavage of a disulfide bond within an $X^2$ linker. In addition to disulfide linkages that take advantage of thiol-disulfide equilibria, linkages including quinones that are cleaved when reduced to hydroquinones may be used in an $X^2$ linker designed for cleavage in reducing environments.

pH-Sensitive Linkers

In some embodiments, $X^2$ linkers are designed to be cleaved in acidic environments, such as sites near damaged or hypoxic tissue. $X^2$ linkers that are cleaved in acidic environments can be utilized to target activation of the promolecules of the present disclosure to acidic regions. Such targeting could be achieved with an acid-labile $X^2$ linker (e.g., by including in $X^2$ an acetal or vinyl ether linkage, or another linkage that is cleaved under acidic conditions).

Combinations of Multiple Linkers

In some embodiments, $X^2$ comprises an amino acid sequence that provides two or more sites susceptible to cleavage (e.g., by an enzyme). Where a molecule having features of the present disclosure includes an $X^2$ linker comprising multiple cleavage sites, separation of portion A from portion Z may require cleavage of multiple bonds within the $X^2$ linker, which may take place either simultaneously or sequentially. Such $X^2$ linkers may include bonds having different chemical properties or cleavage specificities, so that separation of portion A from portion Z requires that more than one condition or environment ("extracellular signals") be encountered by the molecule before activation takes place. The cleavage sites may be the same or different, and where different may be referred to herein as a "chimeric" linker. Cleavage of chimeric $X^2$ linkers thus serves as a detector of combinations of such extracellular signals.

Chimeric $X^2$ linkers may be used to further modulate the targeting of portion A to desired cells, tissue or regions. Boolean combinations of extracellular signals can be used to broaden or narrow the conditions under which cleavage of $X^2$ occurs. Where chimeric $X^2$ linkers are used to link portion A to portion Z, the different chemical bonds within the chimeric linker can be arranged in parallel or in series. When arranged in parallel, the cleavage conditions are narrowed, since each bond must be cleaved before portion A may separate from portion Z. When the chemical bonds within the chimeric linker are arranged in series, the cleavage conditions are broadened, since cleavage of any one of the chemical bonds will result in separation of portion A from portion Z.

For example, in order to detect either a protease or hypoxia (i.e., to cleave $X^2$ in the presence of either a protease or hypoxia), a chimeric $X^2$ linker is designed with the protease-sensitive and reduction-sensitive chemical bonds in series, so that cleavage of either bond would suffice to allow separation of portion A from portion Z.

Alternatively, in order to detect the presence of both a protease and hypoxia (i.e., to cleave $X^2$ in the presence of both a protease and hypoxia but not in the presence of only one of these conditions alone), a dual $X^2$ linker could be designed, e.g., a chimeric linker, to place the protease sensitive bond between at least one pair of cysteines that are disulfide-bonded to each other (i.e., the chemical bonds in the chimeric $X^2$ linker are arranged in parallel). In this case, both protease cleavage and disulfide reduction are required in order to allow separation of portions A and Z.

In certain embodiments, promolecules of the present disclosure may have the following formula (I), wherein portion $X^2$ comprises a dual linker, which may be a chimeric linker, and has a cyclic structure.

(I)

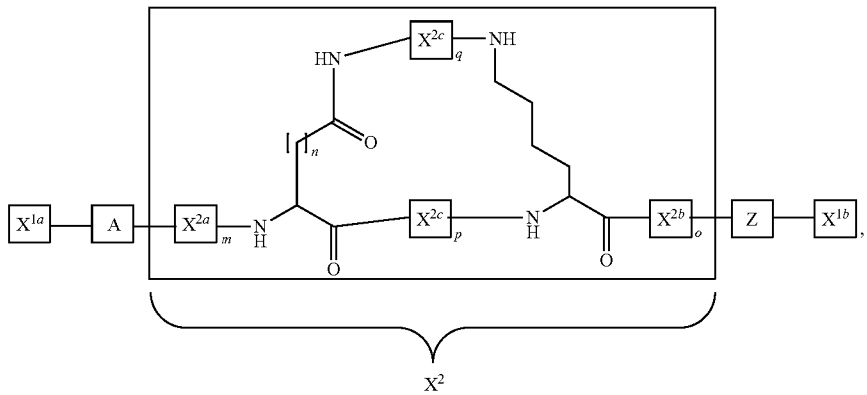

wherein $X^{1a}$, A, Z, and $X^{1b}$ are as described herein. In formula (I) above, $X^{2a}$ and $X^{2b}$ are amino acids of $X^2$, wherein $X^{2a}$ and $X^{2b}$ may be independently selected from any amino acid; $X^{2c}$ and $X^{2d}$ comprise amino acids which provide a cleavable linker (e.g., an enzymatically cleavable linker); n is one or two; m and o are at least one, and may be independently selected from an integer ranging from 1 to 30; p and q are each at least two, and may be independently selected from an integer ranging from two to thirty, wherein the cleavage sites provided by $X^{2c}$ and $X^{2d}$ may the same or different, may be susceptible to cleavage by the same or different conditions (e.g., the same or different enzymes), and may be, for example, independently selected from any of the cleavable linkers described herein. Where $X^{2c}$ and $X^{2d}$ define cleavable linkers that are each susceptible to cleavage under different conditions (e.g., different enzymes), the molecule can be described as comprising a chimeric linker. Such combinations may include enzymes of the same or different class. For example, pairing cleavage sequences of thrombin with that of activated protein C may find utility in discriminating the driving forces between clot formation and its dissolution. For example, pairing the cleavage sequence of MMP-1 with an acid cleavable linker may find utility in targeting the probe to the hypoxic core of cancerous tumors.

Synthesis of a molecule of formula (I) can be performed with standard peptide coupling chemistry. For example, as a precursor to compounds of formula (I), standard peptide coupling chemistry can be used to make a compound of the formula (II) below, wherein $X^2$ comprises an aspartic acid or glutamic acid and lysine residues.

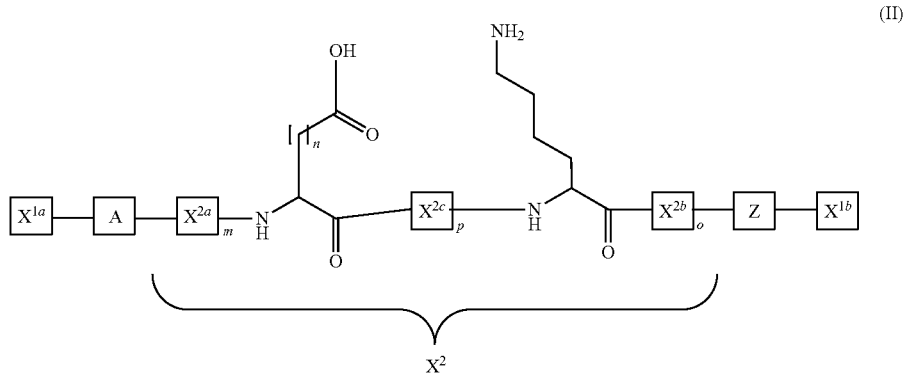

(II)

A peptide coupling reaction typically employs a conventional peptide coupling reagent and is conducted under conventional coupling reaction conditions, typically in the presence of a trialkylamine, such as ethyldiisopropylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), O-(7-azabenzotriazol-1-yl)-N,N,N,N-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF.

During any of the processes for preparation of the compounds, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known in the art. For example, the aspartic acid, glutamic acid, and lysine residues can be protected with various protecting groups during the synthetic process. Depending on the type of protecting group used, selectivity in deprotection can be used advantageously during the synthetic process. One of ordinary skill in the art would be able to select the type of protecting group that is appropriate for the synthetic scheme.

The dual linker described above having a cyclic structure can be synthesized by using the carboxyl side chain of aspartic acid or glutamic acid as the carboxyl handle of a peptide backbone and amino side chain of lysine as the amino handle of a peptide backbone. Synthesis of formula (I) can be performed using standard peptide coupling chemistry. Peptide coupling reactions typically employ a conventional peptide coupling reagent and are conducted under conventional coupling reaction conditions as discussed above.

Portions $X^{1A}$ and $X^{1B}$

Promolecules of the present disclosure may include optional portions $X^{1a}$ and $X^{1b}$ that, when present, comprise a nucleophilic moiety and facilitate the attachment of one or more cargo moieties to the promolecule. The nucleophilic moiety of portions $X^{1a}$ and $X^{1b}$ generally comprises a nucleophilic reactive group comprising at least one pair of free electrons that is capable of reacting with an electrophile. Examples of nucleophilic moieties include sulfur nucleophiles, such as thiols, thiolate anions, anions of thiolcarboxylate, anions of dithiocarbonates, and anions of dithiocarbamates; oxygen nucleophiles, such as hydroxide anion, alcohols, alkoxide anions, and carboxylate anions; nitrogen nucleophiles, such as amines, azides, and nitrates; and carbon nucleophiles, such as alkyl metal halides and enols.

Cargo moieties may be, e.g., detectable moieties that can facilitate detection of a promolecule through various imaging modalities, or may be, e.g., therapeutic agents that can facilitate treatment of a disease or condition.

Non-limiting examples of detectable moieties include fluorescent dyes and radioisotopes. In some embodiments, two or more cargo moieties may be attached to the same promolecule (e.g., a fluorescent dye and a radioisotope attached to the same promolecule). Differing cargo moieties may be paired for simultaneous detection using multiple modalities. For example, non-invasive detection using nuclear imaging agents could be coupled with fluorescence to enable follow on studies for enhanced yet invasive (e.g., surgical) detection.

In some embodiments, a detectable moiety may comprise a fluorescent dye. Non-limiting examples of fluorescent dyes that may be conjugated to promolecules of the present disclosure include cyanine dyes, such as fluorescein, tetramethoxyrhodamine, Cy2, Cy3, Cy3B, Cy3.5, Cy5, Cy5.5, or Cy7, IRdye 800cw, or ATTO-TEC™ dyes, such as ATTO 680. Suitable cargo moieties also include fluorescent dyes having longer wavelengths in the near-infrared region. Such dyes are known in the art and can be readily incorporated into the compounds of the present disclosure.

In some embodiments, a detectable moiety may comprise a radioisotope, e.g., a radioisotope chelated through a metal binding moiety. Non-limiting examples of radioisotopes include Calcium-47, Carbon-11, Carbon-14, Chromium-51, Cobalt-57, Cobalt-58, Erbium-169, Fluorine-18, Gallium-67, Gallium-68, Hydrogen-3, Indium-111, Iodine-123, Iodine-125, Iodine-131, Iron-59, Krypton-81m, Nitrogen-13, Oxygen-15, Phosphorus-32, Samarium-153, Selenium-75, Sodium-22, Sodium-24, Strontium-89, Technetium-99m, Thallium-201, Xenon-133, or Yttrium-90.

In some embodiments, a single promolecule having features of the present disclosure may include more than one cargo moiety so that portion A may be linked to multiple detectable moieties, or to both a detectable moiety and a therapeutic agent, or to multiple therapeutic agents. Such multiple detectable moieties may include different types of markers, and may allow, for example, attachment of both a radioisotope and a contrast agent or fluorescent dye, allowing imaging by different modalities.

Promolecules comprising a detectable moiety conjugated through portion $X^{1a}$ or $X^{1b}$ may have use in visualization or identification of cells having a certain condition or cells in a region exhibiting a particular condition. For example, thrombosis (clot formation) may be visualized by designing an $X^2$ linker to be cleaved by any of the many proteases in the blood clot formation cascade, such as thrombin, so that a cleavage product comprising portion A interacts with cell membranes in the vicinity of the clotting activity. Similarly, complement activation may be visualized by designing an $X^2$ linker to be cleaved by any one or more of the proteases in the complement activation cascades for delivery of a fluorescent dye or other marker to the region. Thus, fluorescent moieties are one example of a cargo moiety that may be delivered to target cell membranes or phospholipid bilayer structures in specific regions upon cleavage of $X^2$.

Non-limiting examples of therapeutic agents that can be conjugated to the promolecules of the present disclosure include radioisotopes such as Calcium-47, Carbon-11, Carbon-14, Chromium-51, Cobalt-57, Cobalt-58, Erbium-169, Fluorine-18, Gallium-67, Gallium-68, Hydrogen-3, Indium-111, Iodine-123, Iodine-125, Iodine-131, Iron-59, Krypton-81m, Nitrogen-13, Oxygen-15, Phosphorus-32, Samarium-153, Selenium-75, Sodium-22, Sodium-24, Strontium-89, Technetium-99m, Thallium-201, Xenon-133, or Yttrium-90.

In some embodiments, a particular moiety may function as both a detectable moiety and as a therapeutic agent.

Methods of Making

Promolecules of the present disclosure can be made by any suitable method, including but not limited to recombinant and non-recombinant (e.g., chemical synthesis) methods. Cargo moieties may be conjugated to promolecules by any suitable method, including but not limited to nucleophilic addition reactions.

Production of Promolecules

The promolecules of the present disclosure can be produced by any suitable method, including recombinant and non-recombinant methods (e.g., chemical synthesis).

Where a polypeptide is chemically synthesized, the synthesis may proceed via liquid-phase or solid-phase. Solid-phase synthesis (SPPS) allows the incorporation of unnatural amino acids, peptide/protein backbone modification. Various forms of SPPS, such as Fmoc and Boc, are available for synthesizing peptides of the present disclosure. Details of the chemical synthesis are known in the art (e.g., Ganesan A. 2006 Mini Rev. Med Chem. 6:3-10 and Camarero J A et al. 2005 Protein Pept Lett. 12:723-8). Briefly, small insoluble, porous beads are treated with functional units on which peptide chains are built. After repeated cycling of coupling/deprotection, the free N-terminal amine of a solid-phase attached peptide or amino acid is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Where the polypeptide is produced using recombinant techniques, the proteins may be produced as an intracellular protein or as a secreted protein, using any suitable construct and any suitable host cell, which can be a prokaryotic or eukaryotic cell, such as a bacterial (e.g. *E. coli*) or a yeast host cell, respectively.

Other examples of eukaryotic cells that may be used as host cells include insect cells, mammalian cells, and/or plant cells. Where mammalian host cells are used, the cells may include one or more of the following: human cells (e.g. HeLa, 293, H9 and Jurkat cells); mouse cells (e.g., X3, NIH3T3, pancreatic ductal adenocarcinoma 2.1, L cells, and C127 cells); primate cells (e.g. Cos 1, Cos 7 and CV1) and hamster cells (e.g., Chinese hamster ovary (CHO) cells).

A wide range of host-vector systems suitable for the expression of the subject polypeptide may be employed according to standard procedures known in the art. See, e.g., Sambrook et al. 1989 Current Protocols in Molecular Biology Cold Spring Harbor Press, New York and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are available commercially.

Vectors can provide for extrachromosomal maintenance in a host cell or can provide for integration into the host cell genome. The expression vector provides transcriptional and translational regulatory sequences, and may provide for inducible or constitutive expression, where the coding region is operably linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like). Expression constructs generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selectable genes are well known in the art and will vary with the host cell used.

Isolation and purification of a protein and/or antibody can be accomplished according to methods known in the art. For example, a protein can be isolated from a lysate of cells genetically modified to express the protein constitutively and/or upon induction, or from a synthetic reaction mixture, by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. Protein of the present disclosure may contain modifications to facilitate isolation.

The subject polypeptides may be prepared in substantially pure or isolated form (e.g., free from other polypeptides). The protein can be present in a composition that is enriched for the polypeptide relative to other components that may be present (e.g., other polypeptides or other host cell components). Purified protein may be provided such that the protein is present in a composition that is substantially free of other expressed proteins, e.g., less than 98%, less than 95%, less than 90%, less than 80%, less than 60%, or less than 50%, of the composition is made up of other expressed proteins.

Conjugation of Cargo Moieties to Polypeptides

Cargo moieties may be conjugated to promolecules of the present disclosure using any suitable technique, including but not limited to nucleophilic addition reactions that utilize nucleophilic moieties. Non-limiting examples of such reactions include reactions of sulfur nucleophiles, oxygen nucleophiles, carbon nucleophiles, or nitrogen nucleophiles with a suitable electrophile to form a covalent bond.

Optional Modifications

Promolecules of the present disclosure may be further modified to generally provide, e.g., longer circulating half-life, restriction of the promolecules to certain anatomical compartments (e.g., restriction to the cardiovascular system), protection against non-specific degradation, and/or enhanced sensitivity to certain imaging modalities.

In some embodiments, two or more promolecules may be linked to a central molecule, e.g., a polyethylene glycol (PEG) molecule, to form a dendrimer using techniques that are known in the art. Suitable PEG molecules may have a molecular weight of up to about 1,000, up to about 5,000, up to about 10,000, up to about 20,000, up to about 30,000, or up to about 40,000 Daltons. Conjugation of two or more promolecules to a central PEG molecule can be accomplished by, e.g., activating a PEG molecule with a functional group at one or more termini and then reacting the activated PEG molecule with one or more promolecules of the present disclosure. The choice of functional groups depends on the available reactive groups on the promolecule, such as the N-terminal amine, the C-terminal carboxylic acid, or residues such as lysine, aspartic acid, cysteine, glutamic acid, serine, threonine, or other specific reactive sites. Linear, single-arm PEG structures, as well as branched PEG structures may be created using such techniques.

In some embodiments, a linear, single-arm PEG structure is formed having the general formula: $X^{1a}\text{-}A\text{-}X^2\text{---}Z\text{---}X^3$, where $X^3$ is a PEG molecule and $X^{1a}$, A, $X^2$, and Z are as described above. In other embodiments, a branched PEG dendrimer is formed using techniques known in the art, wherein two or more promolecules of the present disclosure are conjugated to the branched PEG dendrimer to form a polyvalent PEG structure.

Formulations

Promolecules of the present disclosure can be formulated in a variety of pharmaceutical compositions suitable for administration to a subject (e.g., by a desired route). A composition comprising a promolecule of the present disclosure may comprise a pharmaceutically acceptable excipient, a variety of which are known in the art and need not be discussed in detail herein.

In some embodiments, promolecules of the present disclosure are formulated for parenteral administration to a subject, e.g., intravenous administration. Pharmaceutically acceptable excipients have been amply described in a variety of publications, including, for example, "Remington: The Science and Practice of Pharmacy", 19th Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

In some cases, a subject pharmaceutical composition will be suitable for injection into a subject, e.g., will be sterile. For example, in some embodiments, a subject pharmaceutical composition will be suitable for injection into a human subject, e.g., where the composition is sterile and is free of detectable pyrogens and/or other toxins.

A subject pharmaceutical composition may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH-adjusting and buffering agents, tonicity-adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

Promolecules of the present disclosure may be formulated into unit dosage forms that contain a predetermined amount of the promolecules disclosed herein. Unit dosage forms suitable for injection or intravenous administration may comprise promolecules of the present disclosure in a composition as a solution in sterile water, normal saline, or another pharmaceutically acceptable carrier.

The term "unit dosage form," as used herein, refers to physically discrete units suitable as unitary dosages for human and animal subjects, each unit containing a predetermined quantity of promolecules of the present disclosure calculated in an amount sufficient to produce the desired effect in association with a pharmaceutically acceptable diluent, carrier or vehicle. The specifications for the unit dosage forms of the present disclosure depend on the particular promolecule employed and the effect to be achieved, and the pharmacodynamics associated with each promolecule in the subject.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Promolecules of the present disclosure may also be formulated for oral administration to a patient. For oral preparations, promolecules can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The promolecules of the present disclosure may be utilized in aerosol formulations to be administered via inhalation, or may be formulated into acceptable pressurized propellants, such as dichlorodifluoromethane, propane, nitrogen, and the like.

Furthermore, promolecules of the present disclosure can be made into suppositories by mixing with a variety of bases such as emulsifying bases or water-soluble bases. The promolecules of the present invention can be administered rectally via a suppository. The suppository can include vehicles such as cocoa butter, carbowaxes, and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the promolecules of the present disclosure. Similarly, unit dosage forms for injection or intravenous administration may comprise one or more promolecules in a composition as a solution in sterile water, normal saline or another pharmaceutically acceptable carrier.

In some embodiments, promolecules of the present disclosure are formulated for local administration to a subject, e.g., at or near a site of desired action. In some embodiments, promolecules of the present disclosure are formulated in a sustained release dosage form that is designed to release promolecules at a predetermined rate for a specific period of time.

Promolecules of the present disclosure may also be formulated with agents that influence the pharmacokinetic profile of the promolecule when administered to a subject. Such agents include verapamil or other equivalents.

Routes of Administration

In practicing the methods of the present disclosure, routes of administration may be selected according to any of a variety of factors, such as properties of the promolecule to be delivered, the type of condition being diagnosed, detected, or treated (e.g., detection of clotting), and the like. Promolecules of the present disclosure may be delivered by a route of administration that provides delivery of the promolecule to the bloodstream (e.g., by parenteral administration, such as intravenous administration, intramuscular administration, and/or subcutaneous administration) or to a specific tissue or organ (e.g., muscle tissue, cardiac tissue, vascular tissue, and the like). Injection can be used to accomplish parenteral administration. In some embodiments, promolecules are delivered by a route of administration that provides for delivery of the promolecule directly into affected tissue, e.g., by direct injection into the target tissue or organ.

Promolecules of the present disclosure may be administered through the respiratory tract. Such dosage forms may be smoking devices, dry powder inhalers, pressurized metered dose inhalers, nebulizers, vaporizers, or the like.

Promolecules of the present disclosure may be administered orally by having the subject swallow a suitable dosage form, such as tablets, powders, granules, capsules, elixirs, syrups, or the like. Promolecules of the present disclosure may also be administered rectally in the form of suppositories.

Promolecules of the present disclosure may be administered by direct injection into a target tissue or into the blood stream, including intradermal, subcutaneous, intravenous, intracardiac, intramuscular, intraosseous, or intraperitoneal injection. Promolecules of the present disclosure can be administered by intracavernous or intravitreal delivery to organs or tissues, or administered by intracerebral, intrathecal, or epidural delivery to tissues of the central nervous system.

Promolecules of the present disclosure may be administered locally or topically. Such administration may be accomplished by topically applying a suitable formulation directly to a target tissue. The previously-described routes of administration, formulations and dosage forms are merely exemplary and are in no way limiting.

Dosages

In the methods of the present disclosure, an amount of a promolecule that is effective to achieve the desired diagnosis, detection, or treatment is administered to a subject.

The amount administered varies depending upon the goal of the administration, the health and physical condition of the individual to be treated, age, the degree of resolution desired, the formulation of a subject composition, the activity of the subject composition employed, the treating clinician's assessment of the medical situation, the condition of the subject, the body weight of the subject, as well as the severity of the disease, disorder, or condition being diagnosed, detected, and/or treated, and other relevant factors. The size of the dose will also be determined by the existence, nature, and extent of any adverse side-effects that might accompany the administration of a particular composition.

It is expected that the amount will fall in a relatively broad range that can be determined through routine trials. For example, the amount of a promolecule of the present disclosure employed to detect active clotting in a subject is not more than about the amount that could otherwise be irreversibly toxic to the subject (i.e., maximum tolerated dose). In other cases, the amount is around or even well below the toxic threshold, but still in an effective concentration range, or even as low as a threshold dose. In some embodiments, a dose of 100 micrograms is administered to a subject to detect blood clots in deep vein thrombosis.

Methods of Use

The present disclosure provides methods of using activatable and detectable membrane-interacting peptides for the diagnosis and/or treatment of diseases or conditions generally involving localized biological processes, such as proteolysis. For example, in certain cases, the promolecules of the present disclosure find use as a diagnostic tool in guiding and/or monitoring therapy. Such methods generally involve detection of biological processes, such as proteolysis, which may be associated with a particular disease or condition. The promolecules of the present disclosure also find use in treating particular diseases or conditions, and in methods that involve delivery of therapeutic agents to a particular site or location within a patient.

In general, the methods of the present disclosure involve selecting a promolecule that contains a cleavable linker $X^2$ that is cleaved under conditions associated with a disease or condition to be diagnosed, detected, or treated, and administering the promolecule to a subject in an amount that is sufficient to facilitate detection of the cleavage-promoting condition(s) or to facilitate treatment of a disease/condition associated with the cleavage-promoting condition(s). Administering can be by any suitable route, and the promolecule can be selected according to the disease or condition to be diagnosed or treated. For example, in the case of detection of active clotting within a subject, administration can be intravenous.

When the promolecule encounters cleavage-promoting conditions within the subject, the promolecule is cleaved and the cleavage product containing the membrane-interacting peptide inserts into membranes in the vicinity of the cleavage-promoting environment. In diagnostic uses and methods, identification of the region within the subject where cleavage promoting conditions exist facilitates diagnosis of a disease or condition, and may then provide guidance for administering and/or monitoring an appropriate therapy. In therapeutic uses and methods, delivery of a therapeutic agent to a targeted site within the patient facilitates treatment of a disease or condition.

Diagnostic Uses and Methods

The methods of the present disclosure generally relate to diagnosis and detection of diseases or conditions that involve localized biological processes, such as proteolysis. In some embodiments, the methods of the present disclosure relate to detecting proteolysis resulting from the activity of one or more enzymes that are associated with a particular condition. Such enzymes may be, e.g., bound to or associated with cells located in particular tissues or organs, and the identification of such cells may be useful in guiding and/or monitoring therapy. For example, the enzyme thrombin is associated with sites of active clotting, and the identification of such sites may be useful in diagnosing conditions such as a ruptured arterial plaque. Other enzymes, such as, e.g., matrix metalloproteinase-2 (MMP-2) are known to be associated with malignancies, and their identification may be useful in diagnosing cancer and monitoring tumor growth. In other embodiments, the methods of the present disclosure involve diagnosing infection by detecting proteolysis caused by enzymes associated with infectious organisms, e.g., bacteria or fungi. In such embodiments, the methods of the present disclosure involve detection of proteolysis caused by proteases secreted by an infectious organism, which facilitates diagnosis of the infection.

In other embodiments, the methods of the present disclosure relate to diagnosing conditions that give rise to particular extracellular environments, such as, e.g., inflammation. For example, conditions that give rise to acidic extracellular environments may be detected using promolecules of the present disclosure that contain acid-labile linkers. Similarly, conditions that give rise to reducing extracellular environments may be detected using promolecules of the present disclosure containing linkers that are cleavable under reducing conditions, e.g., disulfide linkers, which may facilitate guidance and monitoring of therapy for such conditions. Non-limiting example methods of the present disclosure are provided below.

The methods of the present disclosure can be adapted to provide for methods of monitoring therapy. For example, a promolecule of the present disclosure can be administered to a subject prior to, during (e.g., between doses), and/or after therapy, and the signal associated with the promolecule can be detected to facilitate the effect of therapy upon the condition being treated.

Detection of Active Clotting

In some embodiments, promolecules are administered to a subject to diagnose active clotting. For example, a promolecule having a thrombin-cleavable $X^2$ linker and having a fluorescent cargo moiety conjugated thereto is administered intravenously to a subject suspected of having a condition involving active clotting, e.g., internal bleeding, or a ruptured arterial plaque. When the promolecule comes into contact with thrombin at a site of active clotting in the subject, $X^2$ is cleaved, forming cleavage products containing portions A and Z. The membrane-interacting peptide of portion A then undergoes a conformational change to form an alpha-helical structure that inserts into cell membranes in the area of the active clotting. The fluorescent cargo moiety attached to portion A can then be detected using fluorescence microscopy to identify the tissues in the subject in which active clotting is taking place. Once these tissues have been identified, an appropriate therapy can be administered to the subject.

In some embodiments, the cargo moiety attached to the promolecule is a radioisotope. Once the cleavage product containing portion A has inserted into the plasma membranes of cells in the area of active clotting, as described above, the radioisotope is detected using an appropriate imaging modality, e.g., fluoroscopy, X-rays, single photon emission computed tomography (SPECT), magnetic resonance (MR) or positron emission tomography (PET) to identify tissues in the subject in which active clotting is taking place.

In some embodiments, promolecules of the present disclosure are administered to a subject during or after therapy in order to monitor the progress of the therapy. For example, after angioplasty has been performed on a subject to treat a ruptured arterial plaque, promolecules of the present disclosure are administered to the subject in order to determine whether any active clotting is still taking place. As described above, a promolecule having a cleavable $X^2$ linker that is cleaved by thrombin and having a fluorescent cargo moiety or a radioisotope cargo moiety conjugated thereto is administered intravenously to the subject. If there are still areas of active clotting within the treated plaque, the promolecule will be cleaved by thrombin at the site, portion A will undergo a conformational change to form an alpha-helical structure and insert into cell membranes in the vicinity, and the active clotting activity can be detected by visualizing the fluorescent moiety or radioisotope. If the clotting activity has decreased, then a diminished signal will be detected at the site of treatment. This information can then be used by the treating physician to monitor the progress of the therapeutic efforts.

Detection of Cancerous Tissues

In some embodiments, the promolecules of the present disclosure are administered to a subject to identify cancerous tissues, e.g., tumors, so that appropriate therapeutic measures can be taken. For example, in some embodiments, a promolecule having a cleavable $X^2$ linker that is cleaved by an enzyme that is over-expressed in cancer cells (e.g., matriptase) is administered to a subject. When the promolecule comes into contact with cancerous cells that over-express a target enzyme, $X^2$ is cleaved, forming cleavage products containing portions A and Z. The membrane-interacting peptide of portion A then undergoes a conformational change to form an alpha-helical structure that inserts into cell membranes in the area of the cancerous cells. The fluorescent cargo moiety attached to portion A can then be detected using fluorescence microscopy to identify the cancerous cells in the subject. Once the cancerous cells have been identified, an appropriate therapy can be administered to the subject, e.g., surgical removal of the tumor.

In some embodiments, a promolecule having a cleavable $X^2$ linker that is cleaved under reducing conditions (e.g. a thiol $X^2$ linker), as may be encountered in hypoxic environments surrounding cancerous tumors, is administered intravenously to a subject. When the promolecule comes into contact with reducing conditions, $X^2$ is cleaved, forming cleavage products containing portions A and Z. The membrane-interacting peptide of portion A then undergoes a conformational change to form an alpha-helical structure that inserts into cell membranes in the area of the cancerous tumors. The fluorescent cargo moiety attached to portion A can then be detected using fluorescence microscopy to identify the cancerous tissues in the subject. Once the cancerous tissues have been identified, an appropriate therapy can be administered to the subject, e.g., surgical removal of the tissues.

Conditions Amenable to Diagnosis

Any condition generally associated with a localized biological process (e.g., enhanced enzymatic activity) or environment (e.g., hypoxia) is amenable to diagnosis using the promolecules and methods disclosed herein. In general, a promolecule is selected to include an $X^2$ linker portion having a structure that is cleavable under the conditions associated with the condition to be diagnosed. Non-limiting examples of conditions amenable to diagnosis using the promolecules and methods of the present disclosure are provided below in Table 4.

TABLE 4

List of conditions amenable to diagnosis using enzymatically-cleavable promolecules of the present disclosure.

| Condition | Enzyme Associated with Condition | Enzyme Cleavage Sequence |
|---|---|---|
| Conditions Involving Clotting | | |
| Heart attack (e.g. due to ruptured plaque); | Thrombin | PR |
| | Factor IXa | LVVR (SEQ ID NO: 33) |
| Stroke; Thrombosis associated with surgical intervention; Left atrial appendage thrombus; Deep vein thrombosis; Thrombosis-associated with cancer; Trauma; | Activated Protein C | LVKR (SEQ ID NO: 36) |
| | Factor VIIa | QLTR (SEQ ID NO: 37) |
| | Factor Xa | LEGR (SEQ ID NO: 32) |
| Cancer | | |
| Cancer (all types) | MMP-2 | PLGLAG (SEQ ID NO: 24) |
| Breast cancer | Prostate specific antigen (KLK3) | SSLY (SEQ ID NO: 40) |
| | Legumain | ASN |
| | Cathepsin B | RR |
| | Stromelysin 3 (MMP-11) | AAA |
| | Urokinase-type plasminogen activator | SSR |
| | Matriptase | KSRAEDE (SEQ ID NO: 28) |

TABLE 4-continued

List of conditions amenable to diagnosis using enzymatically-cleavable promolecules of the present disclosure.

| Condition | Enzyme Associated with Condition | Enzyme Cleavage Sequence |
|---|---|---|
| Prostate cancer | TMPRSS2 | LLRSLIG (SEQ ID NO: 30) |
| Necrosis | | |
| | Calpain-1 | PLFAEP (SEQ ID NO: 25) |
| | Calpain-2 | GLGSEP (SEQ ID NO: 26) |
| Inflammation | | |
| Arthritis | MMP-8 | GPSG (SEQ ID NO: 38) |
| Pancreatitis | Enteropeptidase | DDDDK (SEQ ID NO: 41) |
| Infection | | |
| Parasitic infection | Cruzain | KKLK (SEQ ID NO: 42) |
| Bacterial infection | Complement C1r | QRQR (SEQ ID NO: 43) |
| | C5a peptidase | NISH (SEQ ID NO: 44) |
| Fungal infection | Aspartyl protease | VELLYLV (SEQ ID NO: 31) |
| Neurodegenerative disease | Cathepsin L | PLG |
| | Proprotein Convertase 5 | RSKR (SEQ ID NO: 45) |
| Nephropathy (e.g. diabetic) | MMP-9 | GPAG (SEQ ID NO: 39) |
| Muscular degenerative diseases | Calpain-3 | VGVF (SEQ ID NO: 27) |

Methods of Detecting Cleavage Products A and Z in Diagnostic Applications

Cleavage products A and Z may be detected through a variety of imaging and detection modalities, including by not limited to fluorescence microscopy, X-rays, fluoroscopy, angiography, positron emission tomography (PET), and the like. Detection can be accomplished by directly imaging the cells or tissues in which the cleavage product is located, or by contacting the cells or tissues in which the cleavage product is located with a secondary molecule or reagent, such as an antibody, followed by imaging or detecting the secondary molecule or reagent.

In some embodiments, one or more of the cleavage products is conjugated to a cargo moiety that facilitates detection. In some embodiments, the cargo moiety is a fluorescent dye. In such embodiments, the cargo moiety may be detected directly using fluorescence microscopy, wherein cells, tissues, or entire subjects are placed in the field of a fluorescence microscope and visualized directly.

In some embodiments, the cargo moiety is a radioisotope. In such embodiments, the cargo moiety may be detected using X-rays, fluoroscopy, angiography, positron emission tomography (PET), or single positron emission computed tomography (SPECT) wherein cells, tissues, or entire subjects are placed in the field of the imaging modality and visualized.

In some embodiments, cleavage products are detected using a secondary molecule or reagent, e.g., an antibody, which specifically binds to or interacts with the cleavage products, e.g., an antibody that specifically binds to amino acid sequences in the cleavage products. In such embodiments, cells or tissues containing a cleavage product are contacted with a secondary molecule or reagent, followed by imaging or detecting the secondary molecule or reagent.

Therapeutic Uses and Methods

The methods of the present disclosure generally relate to treatment of diseases or conditions that involve localized biological processes, such as proteolysis. In general, treatment is accomplished by administering a promolecule having an attached therapeutic agent, e.g., a radioisotope, by a route that facilitates delivery of the therapeutic agent to target cells and tissues within a patient. The following are provided as non-limiting exemplary therapeutic uses and methods.

Treatment of Cancerous Tissues

In some embodiments, promolecules of the present disclosure find use in the treatment of cancer by delivering therapeutic agents, e.g., radioisotopes, to cancerous tissues within a patient. Selection of a promolecule for use in treatment is based on expression or over-expression of particular enzymes by cancer cells. For example, the enzyme MMP-2 (cleavage sequence PLGLAG (SEQ ID NO: 24)) is generally expressed by all cancer cells. Breast cancer cells are known to express prostate specific antigen KLK3 (cleavage sequence SSLY (SEQ ID NO: 40)), legumain (cleavage sequence ASN), cathepsin B (cleavage sequence RR), stromelysin 3 (also known as MMP-11) (cleavage sequence AAA), urokinase-type plasminogen activator (cleavage sequence SSR), and matriptase (cleavage sequence KSRAEDE (SEQ ID NO: 28)). Prostate cancer cells are known to express TMPRSS2 (cleavage sequence LLRSLIG (SEQ ID NO: 30)). Alternatively or in addition, cancerous tissues may also be associated with hypoxia or other generally localized conditions.

Cancers amenable to treatment are generally those surrounded by a tissue environment in which an enzyme is present at a localized concentration relative to normal, non-cancerous tissue and/or in which a localized environment (e.g., a hypoxic environment) is present relative to normal, non-cancerous tissue. Such cancers can include solid and semi-solid tumors. Promolecules having a therapeutic agent attached as portion $X^{1\alpha}$ and a cleavable $X^2$ linker that is cleaved by one or more enzymes or conditions associated with a particular type of cancer may be used to facilitate delivery of a therapeutic agent, e.g., a radioisotope, to the cancerous tissues within a patient. After administration of a promolecule to the patient, the cleavable $X^2$ linker is cleaved at or near the site of desired action by an enzyme or condition associated with the cancerous tissue, and the cleavage product comprising portion A inserts into cell membranes and delivers the therapeutic agent to the cancer cells. Delivery of the therapeutic agent to the cancer cells treats the patient by, e.g., killing the cancerous cells, and/or slowing the growth of the cancerous cells.

Screening Methods

The promolecules of the present disclosure generally find use in screening methods, e.g., in vitro or in vivo screening of candidate agents for a desired activity. In some embodiments, the present disclosure relates to methods for screening cells in vitro, e.g., to assess activity of an enzyme expressed by the cells, or to screen for candidate agents that modulate enzymatic activity in the cells. In other embodiments, the present disclosure relates to in vivo screening methods that can be used, e.g., to screen candidate agents for a desired activity in transgenic animal models of disease.

In some embodiments, the screening methods of the present disclosure involve contacting cells in vitro with promolecules having $X^2$ linkers designed to be cleaved by an enzyme of interest. At the surface of cells that express the enzyme of interest, the promolecules are cleaved and the cleavage product containing the membrane-interacting peptide undergoes a conformational change, typically forming an alpha-helical structure that interacts with the plasma membrane of the cell, thereby labeling the cells that express the enzyme of interest. A detectable moiety conjugated to the cleavage product comprising the membrane-interacting peptide can then be detected, which facilitates screening for cells that express the enzyme of interest. The amount of cleavage product that accumulates at a given location or position can therefore be used to screen for a desired enzymatic activity.

In some embodiments, the present disclosure relates to methods for screening cells in vitro that create a particular extracellular environment. In certain embodiments, promolecules are designed so that $X^2$ is cleaved under certain extracellular conditions, e.g., acidic conditions and/or hypoxic conditions. Cultured cells are contacted with such promolecules, and the promolecules are activated by cells that create acidic and/or hypoxic extracellular environments. After cleavage of $X^2$, the cleavage product containing the membrane-interacting peptide undergoes a conformational change to form an alpha-helical structure that inserts into the plasma membrane of the cells, thereby labeling the cells that produce acidic and/or hypoxic extracellular conditions. The detectable moiety conjugated to the cleavage product comprising the membrane-interacting peptide can then be detected, which facilitates screening for cells that produce acidic and/or hypoxic conditions.

The methods of the present disclosure also relate to screening methods that can be used to identify candidate agents or test compounds having a desired activity, e.g., candidate agents that modulate enzymatic activity. In some embodiments, a screening method involves culturing cells in vitro and contacting the cells with a candidate agent or test compound. The cultured cells are then contacted with promolecules of the present disclosure comprising a cleavable linker that is cleaved by an enzyme of interest. Candidate agents or test compounds that elicit a desired activity in the cultured cells facilitate the production of cleavage-promoting conditions that result in cleavage of $X^2$. After cleavage of $X^2$, the cleavage product comprising the membrane-interacting peptide undergoes a conformational change to form an alpha-helical structure that inserts into the plasma membrane of the cells, thereby labeling the cells. An increase in the level of cellular labeling in the presence of the candidate agent or test compound as compared to the level of cellular labeling in the absence of the candidate agent or test compound indicates that the candidate agent or test compound has a desired activity.

The methods of the present disclosure also relate to methods of screening cells in vivo, e.g., to identify candidate agents or test compounds having a desired activity, e.g., candidate agents that modulate enzymatic activity. For example, the screening methods discussed above may be conducted in vivo in animal models, e.g., transgenic animal models of disease, to identify cells or tissues of interest that express (or fail to express) a particular enzyme of interest, or to identify cells or tissues of interest that create a particular extracellular environment, e.g., an acidic and/or hypoxic extracellular environment in response to the candidate agent or test compound.

Kits

Also provided by the present disclosure are kits for using the promolecules disclosed herein and for practicing the methods, as described above. The kits may be provided for administration of promolecules to a subject in which a disease or condition are to be diagnosed. The kit can include one or more of the promolecules and/or cargo moieties as disclosed herein, which may be provided in a sterile container, and can be provided in formulation with a suitable pharmaceutically acceptable excipient for administration to a subject. The promolecules can be provided in a formulation that is ready to be used as it is or can be reconstituted to have the desired concentrations. Where the promolecules are provided to be reconstituted by a user, the kit may also provide buffers, pharmaceutically acceptable excipients, and the like, packaged separately from the subject promolecules.

In addition to the above-mentioned components, the kits can further include instructions for using the components of the kit to practice the methods of the present disclosure. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Materials and Methods

The following materials and methods were used in the examples provided below.

Peptide Synthesis

Oligopeptides were created using the solid phase synthesis techniques of Merrifield. In this approach, oligopeptides were built from repeated cycles of coupling, washing, de-protection and then washing again. At each cycle, the free N-terminal amine of a solid-phase attached peptide was coupled to a single N-protected amino acid unit whose subsequent de-protection revealed a new N-terminal amine to which a further amino acid was attached. Peptide synthesis was used to create promolecules of the $X^{1a}$-A-$X^2$—Z—$X^{1b}$ structure or various portions thereof, e.g., $X^{1a}$-A-$X^2$. Conjugation at $X^{1a}$ or $X^{1b}$ to attach an imaging agent was either (1) performed during the synthesis through the attachment of a lysine unit whose amine was previously coupled to the detection agent or (2) attached to a cysteine on the N-terminus of the peptide using thiol chemistry following synthesis and initial peptide purification. In the latter case, imaging agents such as the fluorescent dye Cy3, Cy5, or ATTO 680 were added using their maleimide forms, which readily react with free thiols present on cysteine side chains to create a covalent linkage. Peptides were synthesized by a commercial supplier and provided as lyophilized samples that were reconstituted in water with or without an organic solvent as necessary to solubilize the compound. In each case, the supplier provided reverse phase high-pressure liquid chromatograms and mass spectra to validate the material.

Analysis by Reverse Phase HPLC

Thrombin-mediated proteolysis of promolecules was performed by incubating the enzyme at concentrations ranging from 0.1 to 2 nM with a 20 to 100 µM solution of the promolecule at 37° C. for up to three or a full twenty-four hours to ensure completeness. The extent of proteolysis was assessed by reverse phase high-pressure liquid chromatography. Samples were run over a $C_{18}$ column using an acetonitrile gradient of 20% to 80% over a period of 30 minutes. Complete hydrolysis was evident by the absence of the initial peak corresponding to the promolecule, and was further validated using mass spectrometry.

Analysis by Intrinsic Fluorescence

Intrinsic fluorescence was used to characterize promolecules containing one or more tryptophan residues in portion A. As the spectral properties of tryptophan are dependent upon its local environment, this provides unequivocal definition of its partitioning into phospholipid membranes. In aqueous conditions, tryptophan typically emits light near 355 nm when excited with 285 nm light. In contrast, the emitted light is red-shifted or lowered when the tryptophan of the peptide is present in an apolar environment, such as the interior of a phospholipid membrane, and produces a maximum emission wavelength typically in the range of 325 to 345 nm. Both the magnitude and wavelength of light emitted under this fluorescence assay are influenced by the properties of the peptide and the composition of the phospholipid membrane. For example, negatively charged groups present in the membrane may reduce the intensity of the emitted signal and weakly interacting peptides may undergo only a slight decrease in maximum emission wavelength. A typical assay employed an 8 µM solution of promolecules and liposomes of defined size (100 nm in diameter, 0.5 mM) composed of phosphatidylserine or phosphatidylcholine or a combination thereof to test the influence of negatively charged or zwitterionic surfaces. Alternatively, detergent micelles of sodium dodecylsulphate (10 mM) or dodecylphosphocholine (5 mM) were used in place of liposomes, as they were easier to prepare and provided similar results. Time-dependent measurement of the fluorescence emission spectra was used to characterize the activation of the promolecules by thrombin (2 nM) or by other proteases (10 nM or higher).

Analysis by Förster Resonance Energy Transfer

Förster resonance energy transfer (FRET) relies upon the ability of light to be exchanged from one fluorescent moiety to another, which becomes possible only when the moieties are in close proximity to one another, typically less than about 30 Angstroms. Liposomes having similar composition to that used in the intrinsic fluorescence assays were prepared with 1% DiO, a lipid-soluble fluorescent compound whose fluorescence emission characteristics match the excitation wavelength of the promolecule when conjugated to Cy5. DiO-containing liposomes (1 µM) were mixed with Cy5 containing promolecules or activated peptide portions (20 nM), and the spectral characteristics of the mixture were determined. Cy3 was excited with 545 nm light, and the emission of Cy5 was measured over 650 to 700 nm. The activated peptide portions, but not the promolecules, enabled fluorescence energy transfer, which confirmed the observations made using intrinsic fluorescence.

Analysis by Circular Dichroism Spectroscopy

Circular dichroism (CD) spectroscopy relies upon the features of the entire peptide and, in particular, its ability to adopt a more compact and regular structure that differentially absorbs polarized light. When a molecule adopts an alpha-helical structure, a stronger differential signal results, particularly over the range of 215 to 400 nanometers. All CD spectra were recorded using a JASCO J710 spectropolarimeter at 25° C., with a cell of 1 mm path length. The CD spectra were obtained using a measurement range from 260 to 190 nm, a 1 nm bandwidth, and 100 nm/min scanning speed. CD spectra of peptides in a concentration ranging from 0.02 to 0.1 mM in phosphate buffered saline in the presence or absence of SDS (20 mM) were obtained. Similar to the results obtained with techniques using fluorescence, the activated peptide portions, but not the promolecules, underwent a more prominent conformational change in the presence of sodium dodecylsulphate micelles.

Characterization of Interaction with Eukaryotic Cells in Suspension

Interaction of the promolecule and its activated peptide form with eukaryotic cell membranes was performed using Jurkat cells that naturally grow in suspension (approximately 100,000 cells in a volume of 100 µL) by incubating the cells with peptides for 2 hours at 37° C. Dulbecco's modified Eagle medium containing 1% fetal bovine serum was used as the cell growth medium. Cell viability was assessed using Trypan blue dye exclusion. Limited toxicity was observed even under high concentrations of the promolecule.

To assess selective activation, the assays were repeated with the exogenous addition of thrombin (5 nM), plasmin (200 nM), and coagulation factor Xa (200 nM). Despite their presence in 40-fold higher abundance, neither plasmin nor factor Xa activated the promolecules (50 µM) with sufficient efficiency to mediate cell death based on trypan blue dye exclusion. In contrast, thrombin efficiently converted the promolecules into the activated peptide form, which mediated cell death in a manner similar to that observed by direct addition of the activated form of the promolecule.

Characterization of Interaction with Eukaryotic Cells on Plasticware

To examine the interaction of the promolecule and its activated form with cell membranes rather than artificial membranes, the promolecules were incubated with cells of the breast cancer cell line MDA-MB-231 (approximately 100,000 cells in a volume of 100 pt) for 1 hour at 37° C. in Dulbecco's modified Eagle medium containing 1% fetal bovine serum, and cell viability was assessed using Trypan blue dye exclusion. Limited toxicity was observed even under high concentrations of the promolecule.

Analysis Using DRAQ7 Exclusion

DRAQ7 is a far-red fluorescent DNA dye that stains the nuclei of dead and permeabilized cells. Unlike trypan blue, it can be combined with other commonly used fluorophores, such as Oregon Green 488 and Cy5. Healthy cells exclude the dye, and no increase in fluorescence is observed. Dead or damaged cells do not exclude the dye, and the dye enters the cells, binds to DNA, and becomes fluorescent. When complexed with double stranded DNA, the dye has a maximum excitation wavelength of 643 nm and a maximum emission wavelength of 694 nm. Cells incubated with the promolecule or the activated peptide form of the promolecule in the presence or absence of thrombin (5 nM) were exposed to DRAQ7 (3 µM) for at least 10 minutes and then imaged using two different approaches. In the first approach, the cells were mouse pancreatic duct adenocarcinoma cells, the incubation buffer contained wheat germ agglutinin conjugated with Oregon Green 488, and the cells were visualized with a Nikon Eclipse Ti-E bearing the appropriate filters. In the second approach, mouse X3 fibroblast cells bearing a modified Histone 2A gene fused to green fluorescent protein (GFP) were imaged using an Acumen Ex3—a commercially available confocal microscopy instrument specifically designed for high throughput, content rich and highly multiplexed data applicable to a wide range of biological assays.

Analysis of Blood Clots Formed on Glass Slides

Whole bovine blood was mixed at a ratio of 5:1 with a 10 nM solution of promolecules bearing the fluorescent dye Cy5. The mixture was then added to 1 uL of activated coagulation factor Xa (10 nM) and calcium chloride (10 mM) to initiate clot formation on the surface of a conventional microscopy slide. The mixture was then stirred with the tip of a plastic pipette for four minutes until a clot was formed. The clot was then pulled gently across the slide with the goal of flattening out the clot for better imaging. A coverslip was then placed on top of the slide and held in place by dabbing the corners with adhesive. The slide was then imaged within a few hours using an epifluorescence microscope (Nikon Eclipse Ti-E) bearing the appropriate filters for detection of the Cy5 dye.

Analysis in Animal Models

Fox N1 nude mice were used for imaging studies when the dye ATTO 680 was conjugated to the promolecule. Unlike Cy5, the ATTO 680 dye enables detection using longer wavelengths that have less auto-fluorescence from the animal, and is therefore more suitable for imaging studies using animal models. Preliminary estimates indicated that the probe bearing the imaging agent was cleared rapidly, having a circulating half-life of ten minutes or less. This short circulating half-life is extremely beneficial for imaging, as the background signal dissipates rapidly. Two different models of in vivo clot formation were investigated. In both models, a solution of the promolecule (0.5 nmol) was injected into the tail vein or inferior vena cava of the mouse as a first step in the procedure.

In the first model, thromboplastin was subsequently administered directly into the inferior vena cava at two different doses. The first dose was fatal to mice within a few minutes of administration. The second dose was five-fold lower than the first dose, and was not fatal to mice within the time frame of the experiment. The thromboplastin model was performed according to Weiss E J, Hamilton J R, Lease K E, Coughlin S R. (2002) *Protection against thrombosis in mice 15 lacking PAR3*, Blood 100(9):3240-4. This approach induces systemic blood clot formation and results in blockage of thinner vasculature in the lungs, and aims to be more reflective of the pulmonary emboli present in a clinical population. The promolecule clearly identified lungs bearing a higher burden of clots despite the blocked vasculature and hence limited ability of the promolecule to accumulate over time.

In the second model, a 28-gauge needle was used to wound the animal in the hind leg, and the progress of clot formation was measured over time. In this approach, the clot formed is generated over a period of time and is more substantial in magnitude. Clot formation was readily detected within minutes, and the intensity of the signal reached a plateau within thirty minutes.

Example 1: Promolecules Containing Temporin-L for the Detection of Blood Clots

Three or four polypeptide modules were combined to form various promolecules capable of controllable cell membrane interaction. A schematic diagram of a promolecule containing four polypeptide modules is shown in FIG. 1. The naturally-occurring sequence of Temporin-L (FVQWFSKFLGRIL (SEQ ID NO: 2)) was modified to restrict non-specific activation by other trypsin-like proteases. The modified sequence (FVQWFSKFLGKLL (SEQ ID NO: 3)) was used as portion A of the promolecule. In order to form the cleavable linker $X^2$, the amino acid sequence PR was added to the C-terminus of portion A.

The naturally-occurring thrombin substrate PAR-1 (SFLLRNPNDKYEPFW (SEQ ID NO: 18)) was modified to reduce its positive charge and add more negative charge. The modifications resulted in the amino acid sequence SFLLQDPNDQYEPFW (SEQ ID NO: 19), which was used to form portion Z of the promolecule. The amino acid sequence of the promolecule containing portions A, $X^2$, and Z, but not optional portion $X^{1a}$ or $X^{1b}$, was therefore: FVQWFSKFLGKLLPRSFLLQDPNDQYEPFW (SEQ ID NO: 47). Promolecules containing optional portion $X^{1a}$ were also formed. These promolecules were formed by adding the amino acid cysteine to the N-terminus of portion A and then conjugating an imaging agent to the cysteine residue. Imaging agents used included Cy5 fluorescent dye and ATTO 680 fluorescent dye.

Once all versions of the promolecule had been synthesized, they were characterized in a number of ways. Intrinsic fluorescence analysis, FRET analysts, and circular dichroism spectroscopy, as described above, were used to analyze the inactive promolecule and the active form of the promolecule. In the presence of phospholipid liposomes or detergent micelles, the active form of the promolecule demonstrated a decrease in maximum emission wavelength using intrinsic tryptophan fluorescence (FIG. 5). The activate form, but not the inactive promolecule form, was capable of FRET to appropriately fluorescent liposomes when the peptide was conjugated to the Cy5 fluorescent dye (FIG. 6). The activate form also demonstrated an increase in alpha-helical content via circular dichroism spectroscopy (FIG. 7). In contrast, the inactive promolecule form showed no binding to liposomes and limited interaction with detergents, indicating that activation had successfully changed the characteristics and properties of the promolecule.

Selective activation of the promolecule by thrombin was confirmed both in vitro and in vivo by incubating the promolecule with eukaryotic cells and examining trypan blue and/or DRAQ7 dye exclusion, as described above, in the presence or absence of exogenous proteases and their inhibitors. At nanomolar concentrations, thrombin activated the promolecule, while several other proteases did not (FIG. 8). Even at much higher concentrations, other proteases did not activate the promolecule, illustrating the high selectivity of the PAR-1 sequence used for protease recognition (FIG. 9). Blocking the activity of thrombin with the known inhibitor hirudin confirmed that thrombin mediated the observed results.

Toxicity was determined by incubating eukaryotic cells with various concentrations of the promolecule or the activated peptide form and analyzing trypan blue and/or DRAQ7 dye exclusion, as described above. After prolonged incubation at peptide-to-cell ratios greater than $10^9$ to one, which occur at high micromolar concentrations of the promolecule that are well above the intended diagnostic range, the incubated cells did not exclude trypan blue dye or DRAQ7 fluorescent dye, indicating that the cell membranes had been destabilized and the cells were no longer viable (FIGS. 10 and 11). Selective activation by thrombin was observed using a DRAQ7-based assay, described above, wherein 5 nM of thrombin and 100 μM of the promolecule were incubated with the cells for up to 60 minutes. The results showed that the cells gradually lost the ability to exclude the DRAQ7 dye over the time frame of the experiment, indicating that the promolecule was activated by thrombin and associated with the cell membranes (FIG. 12).

Analysis of blood clots formed on glass slides, as described above, was used to test localization of the promolecule to sites of thrombin activity. Briefly, clots were formed on glass slides with or without initiation by coagulation factor $X^a$ and calcium chloride in the presence of a promolecule containing Cy5 conjugated via the thiol of the cysteine amino acid added to the N terminus of portion A. Actively clotting platelets were clearly associated with intense accumulation of the activated peptide form of the promolecule (FIG. 13). Without activation, the promolecule did not accumulate on red blood cells. These results indicate that the promolecule could be activated by initiated blood clots, and that the activated form of the promolecule could then localize to the site of an initiated blood clot.

To test activity in vivo, promolecules were injected into mice using two models of thrombosis, described above. In the first model, 500 picomoles of a promolecule wherein $X^1$ was ATTO 680 conjugated via a cysteine residue was injected into the inferior vena cava of a mouse. Subsequently, a fatal or non-fatal dose of thromboplastin was administered to the mouse. A fatal dose was defined as a dose that resulted in animal death within 20 minutes of injection. Following administration of the fatal or non-fatal dose of thromboplastin, the lungs of the animal were surgically removed, visually inspected, and imaged using fluorescence microscopy (FIG. 14). By visual inspection, emboli and damaged lung tissue were evident based on a white appearance of the lungs. Analysis of the fluorescence signal resulting from the ATTO 680 showed that the activated from of the promolecule accumulated at sites of emboli deposition in the lungs.

In a second in vivo model, a 28-gauge needle was used to create a small wound in the hind leg of nude mice after injection of 500 picomoles of the same promolecule described above. The resulting wound was nearly invisible to the naked eye, yet readily accumulated the fluorescent signal within minutes (FIG. 15). Signal intensity was monitored in real-time, producing a progress curve that plateaued within twenty minutes (FIG. 16). These results demonstrated that the promolecule is capable of imaging blood clots in vivo that are less than 1 mm$^3$ with a high signal-to-noise ratio as well as quantifying the magnitude of their formation. Using a standard curve of the fluorescent signal, the local concentration was calculated to be 0.5 µM, or $10^{12}$ molecules, of the activated form of the promolecule in the blood clot that was formed. In the absence of wounding, the activated form of the promolecule accumulated in the duodenum at sites of digestion and was cleared rapidly (FIG. 17).

Example 2: Promolecules Containing Protonectin for the Detection of Blood Clots Protonectin is an antimicrobial peptide that is found in the venom of the neotropical wasp *Agelaia pallipes*. The naturally-occurring sequence of protonectin (ILGTILGLLKGL (SEQ ID NO: 4)) was used to form portion A of a promolecule. Portion $X^2$ was formed from amino acid residues PR, and the modified PAR-1 exosite recognition sequence as described in Example 1 (SFLLQDPNDQYEPFW (SEQ ID NO: 19)) was used to form portion Z. A lysine residue was added to the N-terminus of portion A, and Cy3 fluorescent dye was conjugated to the lysine residue. The combination of these modules resulted in a promolecule having the sequence (Cy3-K)ILGTILGLLKGL-PRSFLLRNPNDKYEPFW (SEQ ID NO: 48).

The promolecule was digested with 0.1 nanomoles of thrombin, followed by analysis with reverse phase HPLC to verify digestion (FIG. 18). Digestion was approximated by the Michaelis-Menten kinetic parameters $k_{cat}/K_M$=8 µM$^{-1}$ sec$^{-1}$ and $K_M$ 200 nM (data/calculations not shown). Portion A of this promolecule lacked a tryptophan residue, and therefore it could not be analyzed using intrinsic fluorescence. FRET analysis, as described above, revealed that membrane-interacting peptides comprising protonectin interact with negatively charged phospholipid membranes, such as phosphatidylserine (FIG. 19). Blood clot formation on glass slides was used to test localization of the activated form of the promolecule to sites of thrombin activity. Blood clots were formed on glass slides with or without initiation by coagulation factor Xa and calcium chloride in the presence of the promolecule. Actively clotting platelets were clearly associated with intense accumulation of the active form of the promolecule as evidenced by visualization of Cy3 via fluorescence microscopy (FIG. 20). Without activation, the promolecule did not accumulate on red blood cells. These results indicated that a promolecule containing protonectin as portion A could be activated by initiated blood clots, and that the active form of the promolecule could then localize to the site of an initiated blood clot.

Example 3: Promolecules Containing Temporin-L for the Detection of Matriptase Activity in Cancer Many proteases have been suggested as potential biomarkers or drug targets for breast cancer, yet they remain underutilized because of the difficulty of detecting proteolysis in vivo. Restricted interaction peptides could therefore be used to diagnose such cancers in addition to being useful as reagents to understand the biology underlying these processes (FIG. 21). Examples of proteases involved with breast cancer include prostate specific antigen, cathepsin B, stromelysin 3, matrix metalloproteinase 2, urokinase-type plasminogen activator, and matriptase, among others.

A promolecule was created whose $X^2$ linker could be cleaved by matriptase, a multidomain membrane-bound serine protease also known as MTSP-1, commonly overexpressed in infiltrating breast carcinomas. The modified Temporin-L peptide sequence described in Example 1 (FVQWFSKFLGKLL (SEQ ID NO: 3)) was used to form portion A, and the matriptase cleavage sequence KSR was used to form cleavable linker $X^2$. A peptide sequence derived from the naturally-occurring substrate vascular endothelial growth factor receptor 2 (VEGFR2) with three additional negative charges to lower the overall pI of the promolecule was used to form portion Z (AEDEGLYDDD (SEQ ID NO: 21)). The combination of these modules resulted in a promolecule having the sequence: (Cy5) FVQWFSKFLGKLLKSRAEDEGLYDDD (SEQ ID NO: 49).

Intrinsic fluorescence analysis, as described above, showed that the promolecule formed from these three portions (A-$X^2$—Z) exhibited moderate restricted interaction with phospholipid membranes and exhibited low toxicity towards MDA-MB-231 cells (FIGS. 22 and 23). Exogeneous addition of different proteases showed that this promolecule was selectively activated by matriptase, as indicated by diminished trypan blue dye exclusion (FIG. 24). Cy5 fluorescent dye was conjugated to this promolecule via an N-terminal thiol (module $X^{1a}$) to create a promolecule having the structure $X^{1a}$-A-$X^2$—Z, and its interaction with HT29 cells was analyzed using fluorescence microscopy. In this experiment, cells were grown to confluence on glass bottom microwell dishes and the peptide (10 uM) incubated with the cells for between one to three hours and then washed for staining with fluorescently-labeled wheat germ agglutinin. After such staining the cells were covered in typical cell culture media and allowed to grow overnight for another round of imaging. Results showed that the activated form of the promolecule accumulated on the surface of the HT29 cells, which are known to express matriptase. Washing the cells to remove unbound molecules, followed by further incubation, revealed that the activated form of the promolecule was internalized into the cells with the natural process of membrane recycling (FIG. 25).

Example 4: Promolecules Containing Temporin-L for the Detection of TMPRSS2 Activity in Cancer A promolecule is synthesized having a portion A sequence of FVQWFSKFLGKLL (SEQ ID NO: 3) derived from Temporin-L, a cleavable linker portion $X^2$ having the sequence RSLIG (SEQ ID NO: 91), which, when contiguously linked to the modified Temporin-L sequence of portion A forms the sequence LLRSLIG (SEQ ID NO: 30), which is recognized and cleaved by the enzyme TMPRSS2, which is known to be associated with metastatic cancer, a portion Z sequence of KVDGTSHVTGDDD (SEQ ID NO: 20), which is known as a protease activated receptor-2 (PAR-2) that specifically interacts with the TMPRSS2 enzyme, and Cy5 fluorescent dye as the detectable moiety on portion $X^{1a}$. The combination of these modules results in a promolecule having the sequence: (Cy5)FVQWFSKFLGKLLRS-LIGKVDGTSHVTGDDD (SEQ ID NO: 50).

This promolecule is administered to a subject suspected of having prostate cancer. Once administered to the subject, the promolecule comes into contact with TMPRSS2 enzymes located on the apical membranes of prostate epithelial cells. Upon contacting the TMPRSS2 enzymes, portion is $X^2$ is cleaved, causing the cleavage product containing portion A to separate from portion Z and undergo a conformational change, forming an alpha-helical structure and inserting into cell membranes in the vicinity of the cleavage. Subsequently, prostate epithelial cells are imaged using fluorescence microscopy to detect the Cy5 fluorescent dye. Detection of the Cy5 dye facilitates diagnosis of prostate cancer in the subject.

Example 5: Promolecules Containing Temporin-L for the Detection of the Secreted Aspartyl Proteases of Pathogenic Fungi A promolecule is synthesized having a portion A sequence of FVQWFSKFLGKLL (SEQ ID NO: 3) derived from Temporin-L, a cleavable linker portion $X^2$ having the sequence VELLYLV (SEQ ID NO: 31) (cleaved by the enzyme Secreted Aspartyl Peptidase (SAP)), a portion Z sequence of DD, and Cy5 fluorescent dye as the detectable moiety on portion $X^{1a}$. The combination of these modules results in a promolecule having the sequence: (Cy5)FVQWFSKFLGKLLVELLYLVDD (SEQ ID NO: 51).

This promolecule may be administered to a subject and used to detect the presence of pathogens that utilize extracellular proteases as virulence factors. Secreted aspartyl peptidases (SAPs), which are known to be secreted by Aspergillus and Candida fungi, cleave the $X^2$ linker having the sequence VELLYLV (SEQ ID NO: 31), causing the cleavage product containing portion A to undergo a conformational change, forming an alpha-helical structure and inserting into cell membranes in the vicinity of the cleavage. Subsequently, areas of the subject suspected of being infected with pathogenic organisms are imaged using fluorescence microscopy to detect the Cy5 fluorescent dye. Detection of the Cy5 dye facilitates diagnosis of an infection.

Example 6: Design of a Compound for Increased Circulating Half-Life

A promolecule having the same structure as that described above in Example 1, with a cysteine residue attached to the N-terminus of portion A and a molecule of Cy5 fluorescent dye conjugated through portion $X^{1a}$ is synthesized (the overall structure being Cy5-CFVQWFSKFLGKLL-PRSFLLQDPNDQYEPFW (SEQ ID NO: 52)). In order to extend the circulating half-life of the promolecule, it is covalently linked to a molecule of polyethylene glycol (PEG) having a moleculer weight of 1,000 Daltons. The PEG-modified promolecule is administered to a subject and the circulating half-life is measured. The PEG-modified form of the promolecule has a longer circulating half-life than the non-PEG-modified form of the promolecule.

Example 7: Promolecule Requiring One of Two Possible Events for Activation

A promolecule having the overall structure $X^{1a}$-A-$X^{2a}$—$X^{2b}$—Z is synthesized, wherein portion A has the sequence FFWLSKIF (SEQ ID NO: 11), portion Z has the sequence DD, and portion $X^{1a}$ comprises a cysteine residue, which is attached to the N-terminus of portion A and conjugated to a molecule of Cy5 fluorescent dye. Portion $X^{2a}$ has the sequence PR, which is cleaved by the enzyme thrombin. Portion $X^{2b}$ has the sequence DDDDK (SEQ ID NO: 41), which is cleaved by the enzyme enteropeptidase. The combination of these modules results in a promolecule having the sequence: (Cy5)CFFWLSKIFPRDDDDKDD (SEQ ID NO: 53).

In order to activate this promolecule, either $X^{2a}$ or $X^{2b}$ must be cleaved, so that this promolecule is activated by either thrombin or enteropeptidase activity. The molecule is administered to a subject, and is cleaved in areas having enteropeptidase or thrombin activity, causing portion A to separate from portion Z and interact with membranes in the vicinity. Areas of a subject suspected of having enteropeptidase or thrombin activity are examined using fluorescence microscopy, and the Cy5 dye is detected in areas having enteropeptidase or thrombin activity.

Example 8: Design of a Promolecule Requiring Two Events for Activation

A promolecule having the overall structure:

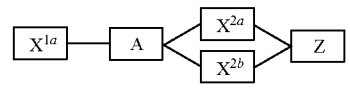

is synthesized, wherein portion A has the sequence FFWLSKIF (SEQ ID NO: 11), portion Z has the sequence DD, and portion $X^{1a}$ comprises a cysteine residue attached to the N-terminus of portion A conjugated to a molecule of Cy5 fluorescent dye. Portion $X^{2a}$ has the sequence PR, which is cleaved by the enzyme thrombin. Portion $X^{2b}$ has the sequence DDDDK (SEQ ID NO: 41), which is cleaved by the enzyme enteropeptidase.

In order to activate this promolecule, both $X^{2'}$ and $X^{2b}$ must be cleaved, so that this promolecule is activated in areas where both thrombin and enteropeptidase are expressed. The molecule is administered to a subject, and is cleaved in areas having both enteropeptidase and thrombin activity, causing portion A to separate from portion Z and interact with membranes in the vicinity. Areas of the subject suspected of having enteropeptidase and thrombin activity are examined using fluorescence microscopy, and Cy5 dye is detected in areas having both enteropeptidase and thrombin activity.

Example 9: Promolecules Containing Temporin-SHF for the

Detection of Blood Clots Via the Activity of Coagulation Factor IXa

A promolecule is synthesized having a portion A sequence of *FFWLSKIF (SEQ ID NO: 11) (which is derived from Temporin-SHf), a cleavable linker portion $X^2$ having the sequence NGRI (SEQ ID NO: 46) and a portion Z having the sequence HNQS(X)SDD, wherein X is either Y, H or Q (SEQ ID NO: 22), which are cleavage sequences of the coagulation factor IXa, and a portion $X^{1a}$ whose N-terminus is derivatized with the fluorescent moiety fluorescein. The combination of these modules results in a promolecule having the sequence: *FFWLSKIFNGRIHNQS(X)SDD, wherein X is either Y, H or Q (SEQ ID NO: 54). * indicates the fluorescent moiety fluorescein.

This promolecule is administered to a subject suspected of having active clotting involving coagulation factor IXa. Once administered to the subject, the promolecule comes into contact with coagulation factor IXa in active clots. Upon contacting the coagulation factor IXa, portion $X^2$ is cleaved, causing the cleavage product containing portion A to undergo a conformational change, forming an alpha-helical structure and inserting into cell membranes in the vicinity of the cleavage. Subsequently, areas of the subject suspected of having clotting activity involving coagulation factor IXa are imaged using fluorescence microscopy to detect the fluorescein dye. Detection of fluorescein facilitates diagnosis of active clotting in the subject.

Example 10: Design of Promolecules Bearing a Different Order of Modules

A promolecule is synthesized having the following formula: $X^{1b}$—Z—$X^2$-A. Amino acid sequences of promolecules having this general formula are listed below in Table 5 (below).

TABLE 5

Promolecules haying a different order of peptide modules. * indicates the presence of a detectable moiety at the N-terminus, the C-terminus, or both of the peptide.

| Target Protease | Z-$X^2$-A | SEQ ID NO: |
|---|---|---|
| Thrombin | *-DDD-LVPRS-FFWLSKIF | SEQ ID NO: 55 |
| aPC | *-DDD-LVKRS-FFWLSKIF | SEQ ID NO: 56 |
| Intermediate 1 | *-DDD-LVGRS-FFWLSKIF | SEQ ID NO: 57 |
| Factor Xa | *-DDD-LEGRS-FFWLSKIF | SEQ ID NO: 58 |
| Intermediate 2 | *-DDD-LVVRS-FFWLSKIF | SEQ ID NO: 59 |
| Factor IXa | *-DDD-LVVRL-FFWLSKIF | SEQ ID NO: 60 |
| Thrombin | DDD-LVPRS-FFWLSKIF-* | SEQ ID NO: 55 |
| aPC | DDD-LVKRS-FFWLSKIF-* | SEQ ID NO: 56 |
| Intermediate 1 | DDD-LVGRS-FFWLSKIF-* | SEQ ID NO: 57 |
| Factor Xa | DDD-LEGRS-FFWLSKIF-* | SEQ ID NO: 58 |
| Intermediate 2 | DDD-LVVRS-FFWLSKIF-* | SEQ ID NO: 59 |
| Factor IXa | DDD-LVVRL-FFWLSKIF-* | SEQ ID NO: 60 |
| Thrombin | *-DDD-LVPRS-FFWLSKIF-* | SEQ ID NO: 55 |
| aPC | *-DDD-LVKRS-FFWLSKIF-* | SEQ ID NO: 56 |
| Intermediate 1 | *-DDD-LVGRS-FFWLSKIF-* | SEQ ID NO: 57 |
| Factor Xa | *-DDD-LEGRS-FFWLSKIF-* | SEQ ID NO: 58 |
| Intermediate 2 | *-DDD-LVVRS-FFWLSKIF-* | SEQ ID NO: 59 |
| Factor IXa | *-DDD-LVVRL-FFWLSKIF-* | SEQ ID NO: 60 |

This promolecule is administered to a subject suspected of having active clotting involving any of the target proteases listed in Table 5. Once administered to the subject, the promolecule comes into contact with the target protease in active clots. Upon contacting the target protease, portion $X^2$ is cleaved, causing the cleavage product containing portion A to undergo a conformational change, forming an alpha-helical structure and inserting into cell membranes in the vicinity of the cleavage. Subsequently, areas of the subject suspected of having clotting activity involving the target protease are imaged to detect the detectable moiety. Detection of the detectable moiety facilitates diagnosis of active clotting in the subject.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A molecule comprising the structure, from N-terminal to C-terminal or C-terminal to N-terminal,

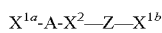

$X^{1a}$-A-$X^2$—Z—$X^{1b}$ wherein:
$X^{1a}$ and/or $X^{1b}$ may be present or absent, and when present comprise a nucleophilic moiety;
A is a membrane-interacting polypeptide portion comprising the amino acid sequence FVQWFSKFLGRIL (SEQ ID NO: 2) or FVQWFSKFLGKLL (SEQ ID NO: 3);
Z is a polypeptide comprising the amino acid sequence SFLLQDPNDQYEPFW (SEQ ID NO:19); and
$X^2$ is an enzymatically cleavable linker, wherein $X^2$ joins portion A to portion Z, and wherein $X^2$ can be cleaved under physiological conditions,
wherein the Z polypeptide inhibits the A membrane-interacting polypeptide portion from interacting with a phospholipid bilayer when the A membrane-interacting polypeptide portion is linked to the Z polypeptide through the $X^2$ enzymatically cleavable linker.

2. The molecule of claim 1, wherein A comprises the amino acid sequence FVQWFSKFLGRIL (SEQ ID NO: 2).

3. The molecule of claim 1, wherein A comprises the amino acid sequence FVQWFSKFLGKLL (SEQ ID NO: 3).

4. The molecule of claim 1, wherein portion Z comprises a covalently linked water-soluble polymer.

5. The molecule of claim 1, wherein one or more of $X^{1a}$, $X^{1b}$, A, or Z comprises a D-amino acid.

6. The molecule of claim 1, wherein $X^{1a}$ is present and comprises a nucleophilic moiety.

7. The molecule of claim 1, wherein $X^{1b}$ is present and comprises a nucleophilic moiety.

8. The molecule of claim 6, wherein the nucleophilic moiety of $X^{1a}$ or $X^{1b}$ comprises a thiol functional group.

9. The molecule of claim 6, wherein $X^{1a}$ or $X^{1b}$ comprises an amino acid residue comprising the nucleophilic moiety.

10. The molecule of claim 9, wherein the amino acid residue is a cysteine residue.

11. The molecule of claim 9, wherein the amino acid residue is a lysine residue.

12. The molecule of claim 6, wherein $X^{1a}$ or $X^{1b}$ comprises a cargo moiety covalently attached to the nucleophilic moiety.

13. The molecule of claim 12, wherein the cargo moiety is a detectable moiety.

14. The molecule of claim 13, wherein the detectable moiety comprises a fluorescent moiety.

15. The molecule of claim 13, wherein the detectable moiety comprises a radioisotope.

16. A composition comprising:
   the molecule of claim 1; and
   a pharmaceutically acceptable carrier.

17. A method of detectably labeling a cell, the method comprising:
   contacting a cell with the molecule of claim 13;
   wherein when said contacting is under conditions suitable for cleavage of the cleavable linker, the molecule is cleaved to release the membrane interacting polypeptide portion for interaction with a phospholipid bilayer of the cell and detectably labels the cell.

18. The method of claim 17, wherein the cell is in vivo.

19. A method of making a molecule useful in delivery of a cargo moiety to a phospholipid bilayer, the method comprising:
   synthesizing the molecule of claim 1, wherein $X^{1a}$ is present; and
   attaching a cargo moiety to the nucleophilic moiety of $X^{1a}$;
   wherein a molecule useful in delivery of a cargo moiety to a phospholipid bilayer is produced.

20. The method of claim 19, wherein said synthesizing comprises culturing a recombinant host cell comprising an expression construct encoding the molecule.

21. The method of claim 19, wherein said synthesizing is by chemical synthesis.

22. The molecule of claim 14, wherein the fluorescent moiety is a water soluble fluorescent dye.

23. The molecule of claim 22, wherein the water soluble fluorescent dye is a cyanine dye.

24. The molecule of claim 23, wherein the cyanine dye is Cy7.

25. The molecule of claim 14, wherein the detectable moiety is a metal chelating moiety.

26. The molecule of claim 25, wherein the metal chelating moiety is 1,4,7,10-tetraazacyclododecane-1,4,7,10-tetraacetic acid (DOTA) or diethylenetriaminepentaacetic acid (DTPA).

27. The molecule of claim 26, wherein the metal chelating moiety is bound to a radioisotope, wherein the radioisotope is Gallium-68 or Technetirum-99m.

28. The molecule of claim 13, wherein the detectable moiety is detectable by positron emission tomography (PET).

29. The molecule of claim 15, wherein the radioisotope is Calcium-47, Carbon-11, Carbon-14, Chromium-51, Cobalt-57, Cobalt-58, Erbium-169, Fluorine-18, Gallium-67, Gallium-68, Hydrogen-3, Indium-111, Iodine-123, Iodine-125, Iodine-131, Iron-59, Krypton-81m, Nitrogen-13, Oxygen-15, Phosphorus-32, Samarium-153, Selenium-75, Sodium-22, Sodium-24, Strontium-89, Technetium-99m, Thallium-201, Xenon-133, or Yttrium-9.

30. The molecule of claim 29, wherein the radioisotope is Gallium-67.

* * * * *

SEQUENCE LISTING

```
<160> NUMBER OF SEQ ID NOS: 95

<210> SEQ ID NO 1
<211> LENGTH: 13
<212> TYPE: PRT
<213> ORGANISM: Artificial sequence
<220> FEATURE:
<223> OTHER INFORMATION: Synthetic amino acid sequence
<220> FEATURE:
```

```
<221> NAME/KEY: MISC_FEATURE
<222> LOCATION: (4)..(4)
<223> OTHER INFORMATION: The amino acid at this position can be I or L
<220> FEATURE:
<221> NAME/KEY: MISC_FEATURE
<222> LOCATION: (10)..(10)
<223> OTHER INFORMATION: The amino acid at this position can be S or G

<400> SEQUENCE: 1

Phe Leu Pro Xaa Ile Ala Ser Leu Leu Xaa Lys Leu Leu
1               5                  10

<210> SEQ ID NO 2
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 2

Phe Val Gln Trp Phe Ser Lys Phe Leu Gly Arg Ile Leu
1               5                  10

<210> SEQ ID NO 3
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 3

Phe Val Gln Trp Phe Ser Lys Phe Leu Gly Lys Leu Leu
1               5                  10

<210> SEQ ID NO 4
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 4

Ile Leu Gly Thr Ile Leu Gly Leu Leu Lys Gly Leu
1               5                  10

<210> SEQ ID NO 5
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 5

Phe Phe Pro Ile Gly Val Phe Cys Lys Ile Phe Lys Thr Cys
1               5                  10

<210> SEQ ID NO 6
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 6

Arg Arg Trp Trp Arg Phe
1               5
```

```
<210> SEQ ID NO 7
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 7

Phe Arg Trp Trp His Arg
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 8

Pro Phe Lys Leu Ser Leu His Leu
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 9

Thr Pro Phe Lys Leu Ser Leu His Leu
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 10

Phe Phe Phe Leu Ser Arg Ile Phe
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 11

Phe Phe Trp Leu Ser Lys Ile Phe
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 12

Lys Val Phe Leu Gly Leu Lys
1               5

<210> SEQ ID NO 13
```

```
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 13

Gly Ile His Asp Ile Leu Lys Tyr Gly Lys Pro Ser
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 14

Ile Leu Gly Lys Ile Trp Glu Gly Ile Lys Ser Leu Phe
1               5                   10

<210> SEQ ID NO 15
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 15

Leu Lys Leu Lys Ser Ile Val Ser Trp Ala Lys Lys Val Leu
1               5                   10

<210> SEQ ID NO 16
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 16

Lys Lys Lys Lys Pro Leu Phe Gly Leu Phe Phe Gly Leu Phe
1               5                   10

<210> SEQ ID NO 17
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 17

Ile Asn Trp Leu Lys Leu Gly Lys Ala Ile Ile Asp Ala Leu
1               5                   10

<210> SEQ ID NO 18
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 18

Ser Phe Leu Leu Arg Asn Pro Asn Asp Lys Tyr Glu Pro Phe Trp
1               5                   10                  15

<210> SEQ ID NO 19
<211> LENGTH: 15
```

```
<212> TYPE: PRT
<213> ORGANISM: Artificial sequence
<220> FEATURE:
<223> OTHER INFORMATION: Synthetic amino acid sequence

<400> SEQUENCE: 19

Ser Phe Leu Leu Gln Asp Pro Asn Asp Gln Tyr Glu Pro Phe Trp
1               5                   10                  15

<210> SEQ ID NO 20
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 20

Lys Val Asp Gly Thr Ser His Val Thr Gly Asp Asp Asp
1               5                   10

<210> SEQ ID NO 21
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 21

Ala Glu Asp Glu Gly Leu Tyr Asp Asp Asp
1               5                   10

<210> SEQ ID NO 22
<211> LENGTH: 8
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (5)..(5)
<223> OTHER INFORMATION: The amino acid at this position can be Y, H or
      Q

<400> SEQUENCE: 22

His Asn Gln Ser Xaa Ser Asp Asp
1               5

<210> SEQ ID NO 23
<211> LENGTH: 15
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (5)..(5)
<223> OTHER INFORMATION: The amino acid at this position can be R or Q

<400> SEQUENCE: 23

Ser Phe Leu Leu Xaa Asn Pro Asn Asp Lys Tyr Glu Pro Phe Trp
1               5                   10                  15

<210> SEQ ID NO 24
<211> LENGTH: 6
<212> TYPE: PRT
<213> ORGANISM: Artificial sequence
<220> FEATURE:
<223> OTHER INFORMATION: Synthetic amino acid sequence
```

```
<400> SEQUENCE: 24

Pro Leu Gly Leu Ala Gly
1               5

<210> SEQ ID NO 25
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 25

Pro Leu Phe Ala Glu Pro
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 26

Gly Leu Gly Ser Glu Pro
1               5

<210> SEQ ID NO 27
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 27

Val Gly Val Phe
1

<210> SEQ ID NO 28
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 28

Lys Ser Arg Ala Glu Asp Glu
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 29

Leu Gln Arg Ala Leu Glu
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 30
```

Leu Leu Arg Ser Leu Ile Gly
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 31

Val Glu Leu Leu Tyr Leu Val
1               5

<210> SEQ ID NO 32
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 32

Leu Glu Gly Arg
1

<210> SEQ ID NO 33
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 33

Leu Val Val Arg
1

<210> SEQ ID NO 34
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 34

Leu Val Gly Arg
1

<210> SEQ ID NO 35
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 35

Leu Val Val Arg Ser
1               5

<210> SEQ ID NO 36
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 36

Leu Val Lys Arg
1

<210> SEQ ID NO 37
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 37

Gln Leu Thr Arg
1

<210> SEQ ID NO 38
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 38

Gly Pro Ser Gly
1

<210> SEQ ID NO 39
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 39

Gly Pro Ala Gly
1

<210> SEQ ID NO 40
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 40

Ser Ser Leu Tyr
1

<210> SEQ ID NO 41
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 41

Asp Asp Asp Asp Lys
1               5

<210> SEQ ID NO 42
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 42

Lys Lys Leu Lys

```
<210> SEQ ID NO 43
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 43

Gln Arg Gln Arg
1

<210> SEQ ID NO 44
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 44

Asn Ile Ser His
1

<210> SEQ ID NO 45
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 45

Arg Ser Lys Arg
1

<210> SEQ ID NO 46
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 46

Asn Gly Arg Ile
1

<210> SEQ ID NO 47
<211> LENGTH: 30
<212> TYPE: PRT
<213> ORGANISM: Artificial sequence
<220> FEATURE:
<223> OTHER INFORMATION: Synthetic amino acid sequence

<400> SEQUENCE: 47

Phe Val Gln Trp Phe Ser Lys Phe Leu Gly Lys Leu Leu Pro Arg Ser
1               5                   10                  15

Phe Leu Leu Gln Asp Pro Asn Asp Gln Tyr Glu Pro Phe Trp
            20                  25                  30

<210> SEQ ID NO 48
<211> LENGTH: 30
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
```

```
<222> LOCATION: (1)..(1)
<223> OTHER INFORMATION: The N-terminal amino acid is conjugated to
      Cyanine3

<400> SEQUENCE: 48

Lys Ile Leu Gly Thr Ile Leu Gly Leu Leu Lys Gly Leu Pro Arg Ser
1               5                   10                  15

Phe Leu Leu Arg Asn Pro Asn Asp Lys Tyr Glu Pro Phe Trp
            20                  25                  30

<210> SEQ ID NO 49
<211> LENGTH: 26
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The N-terminal amino acid is conjugated to
      Cyanine5

<400> SEQUENCE: 49

Phe Val Gln Trp Phe Ser Lys Phe Leu Gly Lys Leu Leu Lys Ser Arg
1               5                   10                  15

Ala Glu Asp Glu Gly Leu Tyr Asp Asp Asp
            20                  25

<210> SEQ ID NO 50
<211> LENGTH: 31
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The N-terminal amino acid is conjugated to
      Cyanine5

<400> SEQUENCE: 50

Phe Val Gln Trp Phe Ser Lys Phe Leu Gly Lys Leu Leu Arg Ser Leu
1               5                   10                  15

Ile Gly Lys Val Asp Gly Thr Ser His Val Thr Gly Asp Asp Asp
            20                  25                  30

<210> SEQ ID NO 51
<211> LENGTH: 22
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The N-terminal amino acid is conjugated to
      Cyanine5

<400> SEQUENCE: 51

Phe Val Gln Trp Phe Ser Lys Phe Leu Gly Lys Leu Leu Val Glu Leu
1               5                   10                  15

Leu Tyr Leu Val Asp Asp
            20

<210> SEQ ID NO 52
<211> LENGTH: 31
<212> TYPE: PRT
```

```
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The N-terminal amino acid is conjugated to
      Cyanine5

<400> SEQUENCE: 52

Cys Phe Val Gln Trp Phe Ser Lys Phe Leu Gly Lys Leu Leu Pro Arg
1               5                   10                  15

Ser Phe Leu Leu Gln Asp Pro Asn Asp Gln Tyr Glu Pro Phe Trp
            20                  25                  30

<210> SEQ ID NO 53
<211> LENGTH: 18
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The N-terminal amino acid is conjugated to
      Cyanine5

<400> SEQUENCE: 53

Cys Phe Phe Trp Leu Ser Lys Ile Phe Pro Arg Asp Asp Asp Lys
1               5                   10                  15

Asp Asp

<210> SEQ ID NO 54
<211> LENGTH: 20
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The N-terminal amino acid is conjugated to
      fluorescein
<220> FEATURE:
<221> NAME/KEY: MISC_FEATURE
<222> LOCATION: (17)..(17)
<223> OTHER INFORMATION: The amino acid at this position can be Y, H or
      Q

<400> SEQUENCE: 54

Phe Phe Trp Leu Ser Lys Ile Phe Asn Gly Arg Ile His Asn Gln Ser
1               5                   10                  15

Xaa Ser Asp Asp
            20

<210> SEQ ID NO 55
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 55

Asp Asp Asp Leu Val Pro Arg Ser Phe Phe Trp Leu Ser Lys Ile Phe
1               5                   10                  15

<210> SEQ ID NO 56
<211> LENGTH: 16
```

<212> TYPE: PRT
<213> ORGANISM: Artificial sequence
<220> FEATURE:
<223> OTHER INFORMATION: Synthetic amino acid sequence

<400> SEQUENCE: 56

Asp Asp Asp Leu Val Lys Arg Ser Phe Phe Trp Leu Ser Lys Ile Phe
1               5                   10                  15

<210> SEQ ID NO 57
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 57

Asp Asp Asp Leu Val Gly Arg Ser Phe Phe Trp Leu Ser Lys Ile Phe
1               5                   10                  15

<210> SEQ ID NO 58
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 58

Asp Asp Asp Leu Glu Gly Arg Ser Phe Phe Trp Leu Ser Lys Ile Phe
1               5                   10                  15

<210> SEQ ID NO 59
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 59

Asp Asp Asp Leu Val Val Arg Ser Phe Phe Trp Leu Ser Lys Ile Phe
1               5                   10                  15

<210> SEQ ID NO 60
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 60

Asp Asp Asp Leu Val Val Arg Leu Phe Phe Trp Leu Ser Lys Ile Phe
1               5                   10                  15

<210> SEQ ID NO 61
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 61

Phe Leu Pro Leu Ile Gly Arg Val Leu Ser Gly Ile Leu
1               5                   10

<210> SEQ ID NO 62
<211> LENGTH: 13
<212> TYPE: PRT

```
<213> ORGANISM: Artificial sequence
<220> FEATURE:
<223> OTHER INFORMATION: Synthetic amino acid sequence

<400> SEQUENCE: 62

Leu Leu Pro Ile Val Gly Asn Leu Leu Lys Ser Leu Leu
1               5                   10

<210> SEQ ID NO 63
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 63

Leu Leu Pro Ile Leu Gly Asn Leu Leu Asn Gly Leu Leu
1               5                   10

<210> SEQ ID NO 64
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 64

Leu Leu Pro Ile Val Gly Asn Leu Leu Asn Ser Leu Leu
1               5                   10

<210> SEQ ID NO 65
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 65

Val Leu Pro Ile Ile Gly Asn Leu Leu Asn Ser Leu Leu
1               5                   10

<210> SEQ ID NO 66
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 66

Phe Leu Pro Leu Ile Gly Lys Val Leu Ser Gly Ile Leu
1               5                   10

<210> SEQ ID NO 67
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 67

Phe Phe Pro Val Ile Gly Arg Ile Leu Asn Gly Ile Leu
1               5                   10

<210> SEQ ID NO 68
<211> LENGTH: 10
<212> TYPE: PRT
<213> ORGANISM: Artificial sequence
```

```
<220> FEATURE:
<223> OTHER INFORMATION: Synthetic amino acid sequence

<400> SEQUENCE: 68

Leu Ser Pro Asn Leu Leu Lys Ser Leu Leu
1               5                   10

<210> SEQ ID NO 69
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 69

Leu Leu Pro Asn Leu Leu Lys Ser Leu Leu
1               5                   10

<210> SEQ ID NO 70
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 70

Phe Val Gln Trp Phe Ser Lys Phe Leu Gly Arg Ile Leu
1               5                   10

<210> SEQ ID NO 71
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 71

Phe Leu Pro Phe Leu Ala Lys Ile Leu Thr Gly Val Leu
1               5                   10

<210> SEQ ID NO 72
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 72

Phe Leu Pro Leu Phe Ala Ser Leu Ile Gly Lys Leu Leu
1               5                   10

<210> SEQ ID NO 73
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 73

Phe Leu Pro Phe Leu Ala Ser Leu Leu Thr Lys Val Leu
1               5                   10

<210> SEQ ID NO 74
<211> LENGTH: 13
<212> TYPE: PRT
<213> ORGANISM: Artificial sequence
<220> FEATURE:
```

<223> OTHER INFORMATION: Synthetic amino acid sequence

<400> SEQUENCE: 74

Phe Leu Pro Phe Leu Ala Ser Leu Leu Ser Lys Val Leu
1               5                   10

<210> SEQ ID NO 75
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 75

Phe Leu Pro Phe Leu Ala Thr Leu Leu Ser Lys Val Leu
1               5                   10

<210> SEQ ID NO 76
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 76

Ser Ile Leu Pro Thr Ile Val Ser Phe Leu Ser Lys Val Phe
1               5                   10

<210> SEQ ID NO 77
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 77

Ser Ile Leu Pro Thr Ile Val Ser Phe Leu Ser Lys Phe Leu
1               5                   10

<210> SEQ ID NO 78
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 78

Ser Ile Leu Pro Thr Ile Val Ser Phe Leu Thr Lys Phe Leu
1               5                   10

<210> SEQ ID NO 79
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 79

Phe Ile Leu Pro Leu Ile Ala Ser Phe Leu Ser Lys Phe Leu
1               5                   10

<210> SEQ ID NO 80
<211> LENGTH: 13
<212> TYPE: PRT
<213> ORGANISM: Artificial sequence
<220> FEATURE:
<223> OTHER INFORMATION: Synthetic amino acid sequence

```
<400> SEQUENCE: 80

Val Leu Pro Leu Ile Ser Met Ala Leu Gly Lys Leu Leu
1               5                   10

<210> SEQ ID NO 81
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 81

Asn Phe Leu Gly Thr Leu Ile Asn Leu Ala Lys Lys Ile Met
1               5                   10

<210> SEQ ID NO 82
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 82

Phe Leu Pro Ile Leu Ile Asn Leu Ile His Lys Gly Leu Leu
1               5                   10

<210> SEQ ID NO 83
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 83

Phe Leu Pro Ile Val Gly Lys Leu Leu Ser Gly Leu Leu
1               5                   10

<210> SEQ ID NO 84
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 84

Phe Leu Pro Ile Ala Ser Leu Leu Gly Lys Tyr Leu
1               5                   10

<210> SEQ ID NO 85
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 85

Phe Ile Ser Ala Ile Ala Ser Met Leu Gly Lys Phe Leu
1               5                   10

<210> SEQ ID NO 86
<211> LENGTH: 13
<212> TYPE: PRT
<213> ORGANISM: Artificial sequence
<220> FEATURE:
<223> OTHER INFORMATION: Synthetic amino acid sequence
```

<400> SEQUENCE: 86

Phe Leu Ser Ala Ile Ala Ser Met Leu Gly Lys Phe Leu
1               5                   10

<210> SEQ ID NO 87
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 87

Phe Ile Ser Ala Ile Ala Ser Phe Leu Gly Lys Phe Leu
1               5                   10

<210> SEQ ID NO 88
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 88

Phe Leu Phe Pro Leu Ile Thr Ser Phe Leu Ser Lys Val Leu
1               5                   10

<210> SEQ ID NO 89
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 89

Phe Leu Pro Ala Ile Ala Gly Ile Leu Ser Gln Leu Phe
1               5                   10

<210> SEQ ID NO 90
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 90

Phe Leu Pro Leu Ile Ala Gly Leu Leu Gly Lys Leu Phe
1               5                   10

<210> SEQ ID NO 91
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 91

Arg Ser Leu Ile Gly
1               5

<210> SEQ ID NO 92
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 92

```
Phe Phe Pro Leu Ala Leu Leu Cys Lys Val Phe Lys Lys Cys
1               5                   10

<210> SEQ ID NO 93
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 93

Phe Leu Leu Phe Pro Leu Met Cys Lys Ile Gln Gly Lys Cys
1               5                   10

<210> SEQ ID NO 94
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 94

Phe Val Leu Pro Leu Val Met Cys Lys Ile Leu Arg Lys Cys
1               5                   10

<210> SEQ ID NO 95
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 95

Phe Gly Leu Pro Met Leu Ser Ile Leu Pro Lys Ala Leu Cys Ile Leu
1               5                   10                  15

Leu Lys Arg Lys Cys
            20
```